(12) United States Patent
Nojoomi et al.

(10) Patent No.: US 12,070,257 B2
(45) Date of Patent: Aug. 27, 2024

(54) SYSTEMS, DEVICES, AND METHODS FOR ABLATION AND DEFUNCTIONALIZATION OF A GALLBLADDER

(71) Applicant: Ictero Medical, Inc., Houston, TX (US)

(72) Inventors: Matthew Nojoomi, Houston, TX (US); David Waters, Houston, TX (US); Aedan Mangan, Cleveland, OH (US); Eric Ryba, Durango, CO (US); Michael Mulanix, Lakewood, CO (US)

(73) Assignee: Ictero Medical, Inc., Houston, TX (US)

( * ) Notice: Subject to any disclaimer, the term of this patent is extended or adjusted under 35 U.S.C. 154(b) by 0 days.

(21) Appl. No.: 18/108,831

(22) Filed: Feb. 13, 2023

(65) Prior Publication Data
US 2023/0218332 A1    Jul. 13, 2023

Related U.S. Application Data

(63) Continuation of application No. PCT/US2021/045987, filed on Aug. 13, 2021.
(Continued)

(51) Int. Cl.
*A61B 17/00*    (2006.01)
*A61B 18/00*    (2006.01)
*A61B 18/02*    (2006.01)

(52) U.S. Cl.
CPC ............... *A61B 18/0218* (2013.01); *A61B 2017/00336* (2013.01); *A61B 2018/0016* (2013.01);
(Continued)

(58) Field of Classification Search
CPC ................................ A61M 2202/03
See application file for complete search history.

(56) References Cited

U.S. PATENT DOCUMENTS

| 4,696,668 | A | 9/1987 | Wilcox |
| 4,781,677 | A | 11/1988 | Wilcox |

(Continued)

FOREIGN PATENT DOCUMENTS

| CN | 101309651 A | 11/2008 |
| CN | 201743767 U | 2/2011 |

(Continued)

OTHER PUBLICATIONS

Extended European Search Report for European Application No. 19750455.8, mailed Nov. 18, 2021, 9 pages.
(Continued)

*Primary Examiner* — Linda C Dvorak
*Assistant Examiner* — Nicholas S Borsch
(74) *Attorney, Agent, or Firm* — COOLEY LLP

(57) ABSTRACT

Provided herein are catheter devices, systems, and methods to ablate a tissue location. The devises, systems, and methods disclosed herein include ablation systems including a catheter system with inner and outer shafts that deliver an ablation medium (e.g., a cryogenic ablation medium) to a body lumen and evacuate the ablation medium from the body lumen. In some embodiments, devices, systems, and methods disclose herein include expandable structures that facilitate in positioning of nozzles and/or evacuation of ablation medium from a body lumen.

28 Claims, 47 Drawing Sheets

Related U.S. Application Data

(60) Provisional application No. 63/066,005, filed on Aug. 14, 2020.

(52) U.S. Cl.
CPC .............. *A61B 2018/00214* (2013.01); *A61B 2018/00535* (2013.01); *A61B 2018/00577* (2013.01); *A61B 2018/00642* (2013.01); *A61B 2018/00791* (2013.01); *A61B 2018/0212* (2013.01)

(56) References Cited

U.S. PATENT DOCUMENTS

| | | | |
|---|---|---|---|
| 4,979,948 A | 12/1990 | Geddes et al. | |
| 5,045,056 A | 9/1991 | Behl | |
| 5,100,388 A | 3/1992 | Behl et al. | |
| 5,159,925 A | 11/1992 | Neuwirth et al. | |
| 5,183,464 A | 2/1993 | Dubrul et al. | |
| 5,188,602 A | 2/1993 | Nichols | |
| 5,213,571 A | 5/1993 | Fujio et al. | |
| 5,452,582 A | 9/1995 | Longsworth | |
| 5,501,681 A | 3/1996 | Neuwirth et al. | |
| 5,891,134 A | 4/1999 | Goble et al. | |
| 6,077,261 A | 6/2000 | Behl et al. | |
| 6,245,064 B1* | 6/2001 | Lesh ................ | A61M 25/1002 606/34 |
| 6,283,959 B1 | 9/2001 | Lalonde et al. | |
| 6,383,181 B1 | 5/2002 | Johnston et al. | |
| 6,494,844 B1 | 12/2002 | Van et al. | |
| 6,517,533 B1 | 2/2003 | Swaminathan | |
| 6,575,966 B2 | 6/2003 | Lane et al. | |
| 6,599,299 B2 | 7/2003 | Schultz | |
| 6,623,479 B1 | 9/2003 | Nun | |
| 7,025,762 B2 | 4/2006 | Johnston et al. | |
| 8,048,101 B2 | 11/2011 | Lee-Sepsick et al. | |
| 8,062,282 B2 | 11/2011 | Kolb | |
| 8,327,852 B2 | 12/2012 | Nikolchev et al. | |
| 8,382,746 B2 | 2/2013 | Williams et al. | |
| 8,663,211 B2 | 3/2014 | Fourkas et al. | |
| 9,144,449 B2 | 9/2015 | Burr et al. | |
| 9,168,081 B2 | 10/2015 | Williams et al. | |
| 9,282,968 B2 | 3/2016 | Van et al. | |
| 9,301,796 B2 | 4/2016 | Burr et al. | |
| 9,326,757 B2 | 5/2016 | Ravikumar et al. | |
| 9,486,219 B2 | 11/2016 | Van et al. | |
| 9,757,535 B2 | 9/2017 | Rajagopalan et al. | |
| 9,820,797 B2 | 11/2017 | Burr et al. | |
| 9,844,641 B2 | 12/2017 | Rajagopalan et al. | |
| 9,931,152 B2 | 4/2018 | Wittenberger et al. | |
| 10,004,550 B2 | 6/2018 | Ryba et al. | |
| 10,383,676 B2 | 8/2019 | Williams et al. | |
| 10,610,663 B2* | 4/2020 | Rajagopalan ......... | A61M 25/00 |
| 10,980,590 B2 | 4/2021 | Rajagopalan et al. | |
| 10,993,827 B2 | 5/2021 | Kim | |
| 11,026,738 B2 | 6/2021 | Saadat et al. | |
| 11,033,319 B2 | 6/2021 | Kochavi | |
| 11,185,360 B2 | 11/2021 | Mulcahey | |
| 11,207,117 B2 | 12/2021 | McDermott et al. | |
| 11,259,857 B2 | 3/2022 | Lalonde | |
| 11,259,858 B1 | 3/2022 | Rahimzadeh et al. | |
| 11,364,065 B2 | 6/2022 | Downey et al. | |
| 2002/0022832 A1 | 2/2002 | Mikus et al. | |
| 2003/0130650 A1* | 7/2003 | Yaron ................... | A61B 18/02 606/21 |
| 2004/0024392 A1 | 2/2004 | Lewis et al. | |
| 2004/0215180 A1 | 10/2004 | Starkebaum et al. | |
| 2005/0107736 A1 | 5/2005 | Landman et al. | |
| 2005/0251121 A1* | 11/2005 | Swanson ............... | A61B 18/02 606/21 |
| 2006/0122590 A1 | 6/2006 | Bliweis et al. | |
| 2008/0255550 A1 | 10/2008 | Bell | |
| 2009/0036823 A1 | 2/2009 | LePivert | |
| 2009/0143759 A1 | 6/2009 | Van Dam et al. | |
| 2009/0143760 A1 | 6/2009 | Van Dam et al. | |
| 2009/0157002 A1 | 6/2009 | Dumot et al. | |
| 2009/0192505 A1 | 7/2009 | Askew et al. | |
| 2010/0094270 A1 | 4/2010 | Sharma | |
| 2010/0179526 A1 | 7/2010 | Lawrence | |
| 2011/0071350 A1 | 3/2011 | Van Dam et al. | |
| 2011/0125143 A1 | 5/2011 | Gross et al. | |
| 2012/0089047 A1 | 4/2012 | Ryba et al. | |
| 2012/0109119 A1 | 5/2012 | Lalonde | |
| 2012/0136343 A1 | 5/2012 | Burnett | |
| 2012/0143298 A1* | 6/2012 | Just ..................... | A61B 5/287 607/122 |
| 2012/0289880 A1 | 11/2012 | Van Dam et al. | |
| 2013/0012938 A1* | 1/2013 | Asirvatham ............ | A61B 5/24 606/41 |
| 2013/0030410 A1 | 1/2013 | Drasler et al. | |
| 2013/0103020 A1 | 4/2013 | Levin | |
| 2013/0144322 A1 | 6/2013 | Callaghan et al. | |
| 2013/0218149 A1 | 8/2013 | Braun et al. | |
| 2014/0180248 A1 | 6/2014 | Salik | |
| 2014/0243780 A1 | 8/2014 | Leschinsky et al. | |
| 2014/0277428 A1 | 9/2014 | Skemp et al. | |
| 2015/0018808 A1* | 1/2015 | Mihalik ................ | A61B 18/02 606/21 |
| 2015/0148738 A1 | 5/2015 | Caplan et al. | |
| 2015/0164571 A1 | 6/2015 | Saadat | |
| 2015/0272666 A1 | 10/2015 | Wang | |
| 2015/0342669 A1* | 12/2015 | Flanagan ........... | A61B 18/1482 606/41 |
| 2016/0008050 A1* | 1/2016 | Rajagopalan ...... | A61N 1/36007 606/34 |
| 2016/0022346 A1 | 1/2016 | Shadduck | |
| 2016/0038212 A1 | 2/2016 | Ryba et al. | |
| 2016/0067465 A1* | 3/2016 | Gerrans ................ | A61B 17/24 606/196 |
| 2016/0302762 A1 | 10/2016 | Stigall et al. | |
| 2017/0072173 A1 | 3/2017 | Van Dam et al. | |
| 2017/0265924 A1 | 9/2017 | Kochavi | |
| 2018/0014868 A1 | 1/2018 | O'Connor et al. | |
| 2018/0028250 A1 | 2/2018 | O'Connor | |
| 2018/0036058 A1 | 2/2018 | Fan et al. | |
| 2019/0328437 A1 | 10/2019 | Perron et al. | |
| 2020/0275968 A1 | 9/2020 | McGregor et al. | |
| 2020/0297403 A1 | 9/2020 | Kochavi | |
| 2020/0360670 A1* | 11/2020 | Legum ................. | A61B 18/04 |
| 2021/0169545 A1 | 6/2021 | Hareland | |
| 2022/0401145 A1 | 12/2022 | Nojoomi et al. | |
| 2023/0090573 A1 | 3/2023 | Legum et al. | |
| 2023/0135845 A1 | 5/2023 | Coulombe | |

FOREIGN PATENT DOCUMENTS

| | | |
|---|---|---|
| CN | 103221089 A | 7/2013 |
| CN | 105283141 A | 1/2016 |
| CN | 109091176 A | 12/2018 |
| EP | 2252228 B1 | 11/2016 |
| GB | 2064082 A | 6/1981 |
| JP | H03126446 A | 5/1991 |
| JP | H049150 A | 1/1992 |
| JP | H04501821 A | 4/1992 |
| JP | H07500513 A | 1/1995 |
| JP | 2007500545 A | 1/2007 |
| JP | 2010531178 A | 9/2010 |
| JP | 2020503097 A | 1/2020 |
| JP | 2020518305 A | 6/2020 |
| WO | WO-1993008753 | 5/1993 |
| WO | WO-2007001981 A2 | 1/2007 |
| WO | WO-2011142909 A1 | 11/2011 |
| WO | WO-2012071031 A1 | 5/2012 |
| WO | WO-2018044985 A1 | 3/2018 |
| WO | WO-2018106688 A2 | 6/2018 |
| WO | WO-2018142411 | 8/2018 |
| WO | WO-2019055800 A1 | 3/2019 |
| WO | WO-2019157221 A1 | 8/2019 |
| WO | WO-2021026467 A1 | 2/2021 |
| WO | WO-2022036250 A1 | 2/2022 |

(56) References Cited

FOREIGN PATENT DOCUMENTS

WO  WO-2022066873 A1  3/2022
WO  WO-2023154886 A1  8/2023

OTHER PUBLICATIONS

First Office Action for Chinese Application No. 201980023912.1, mailed Apr. 24, 2022, 20 pages.
International Search Report and Written Opinion for International Application No. PCT/US2019/017112, mailed Jun. 14, 2019, 11 pages.
International Search Report and Written Opinion for International Application No. PCT/US2020/045436, mailed Jan. 21, 2021, 15 pages.
International Search Report and Written Opinion for International Application No. PCT/US2021/045987, mailed Nov. 29, 2021, 12 pages.
Invitation to Pay Additional Fees, Communication Relating to the Results of the Partial International Search and Provisional Opinion for International Application No. PCT/US2020/045436, mailed Nov. 5, 2020, 10 pages.
Office Action for Japanese Application No. JP20200542754, dated Nov. 11, 2022, 8 pages.
Office Action for U.S. Appl. No. 16/988,028, mailed Apr. 6, 2021, 19 pages.
Office Action for U.S. Appl. No. 16/988,028, mailed Dec. 15, 2020, 21 pages.
Office Action for U.S. Appl. No. 16/988,028, mailed Jan. 24, 2022, 23 pages.
Non Final Office Action for U.S. Appl. No. 17/865,469 dated Mar. 24, 2023, 30 pages.
International Search Report and Written Opinion for International Application No. PCT/US2023/062419 dated Jul. 28, 2023, 18 pages.
Invitation to Pay Additional Fees, Communication Relating to the Results of the Partial International Search and Provisional Opinion for International Application No. PCT/US2023/062419, mailed Jun. 7, 2023, 13 pages.
Notice of Reasons for Rejection for Japanese Application No. 2020-542754 dated May 31, 2023, 4 pages.
Office Action for Australian Application No. 2019218889 dated Nov. 17, 2023, 3 pages.
Office Action for Japanese Application No. 2020-542754 dated Nov. 20, 2023, 4 pages.
Office Action for Mexican Application No. MX/a/2020/008362 dated Feb. 6, 2024, 9 pages.
Office Action for U.S. Appl. No. 17/865,469 dated Dec. 29, 2023, 26 pages.
Notice of Reasons for Refusal for Japanese Application No. 2022-506913 mailed Mar. 29, 2024, 14 pages.

\* cited by examiner

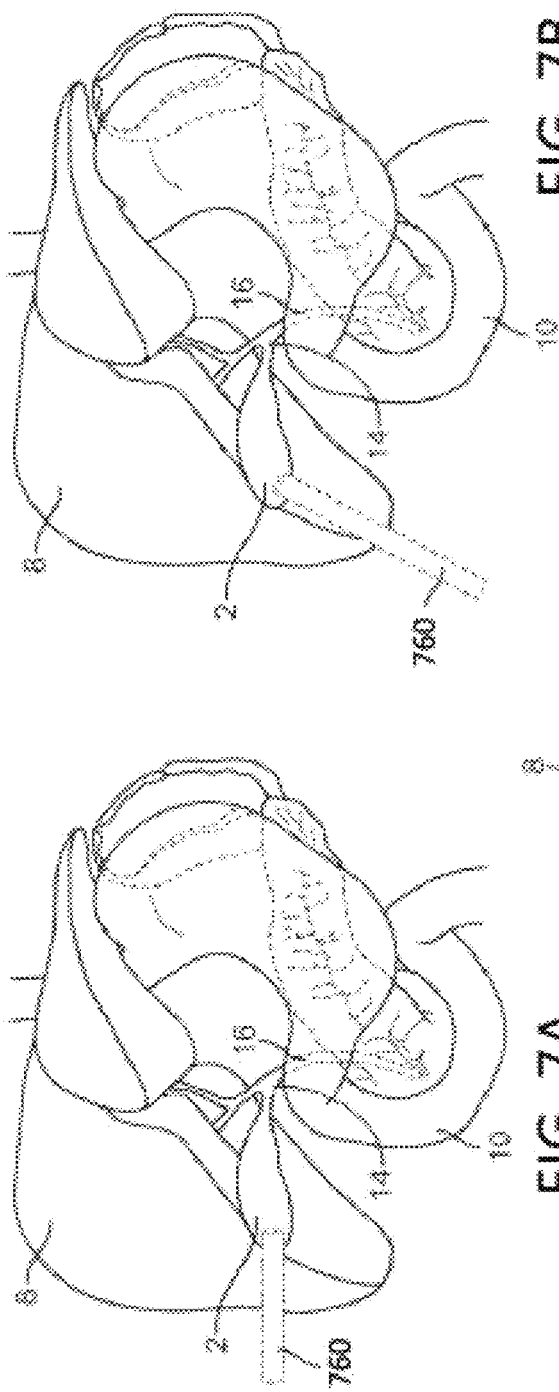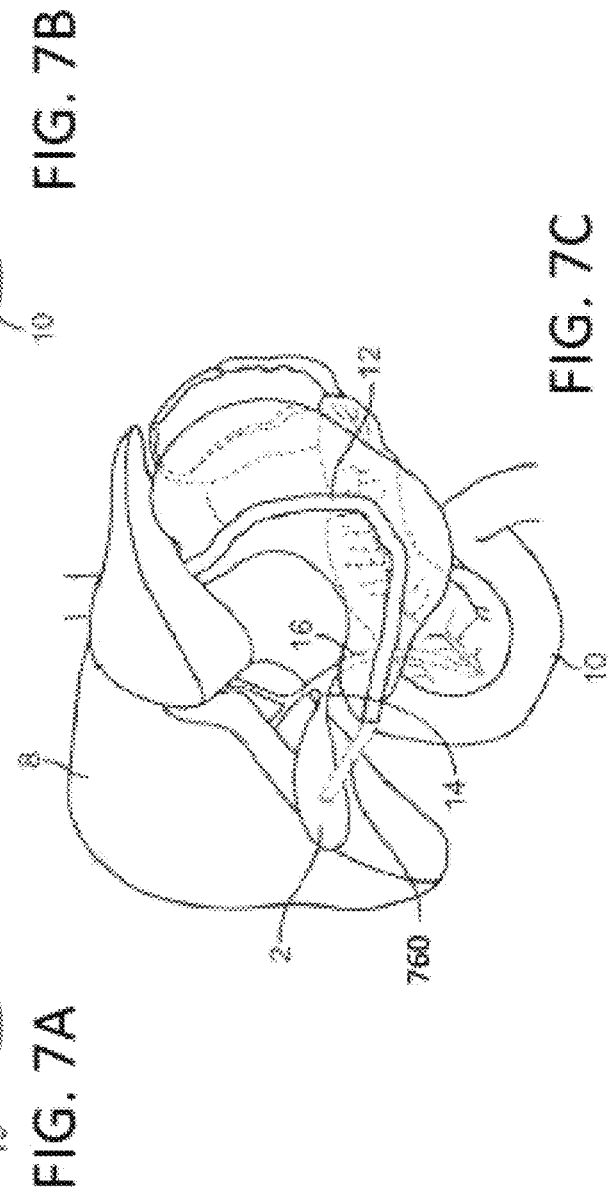

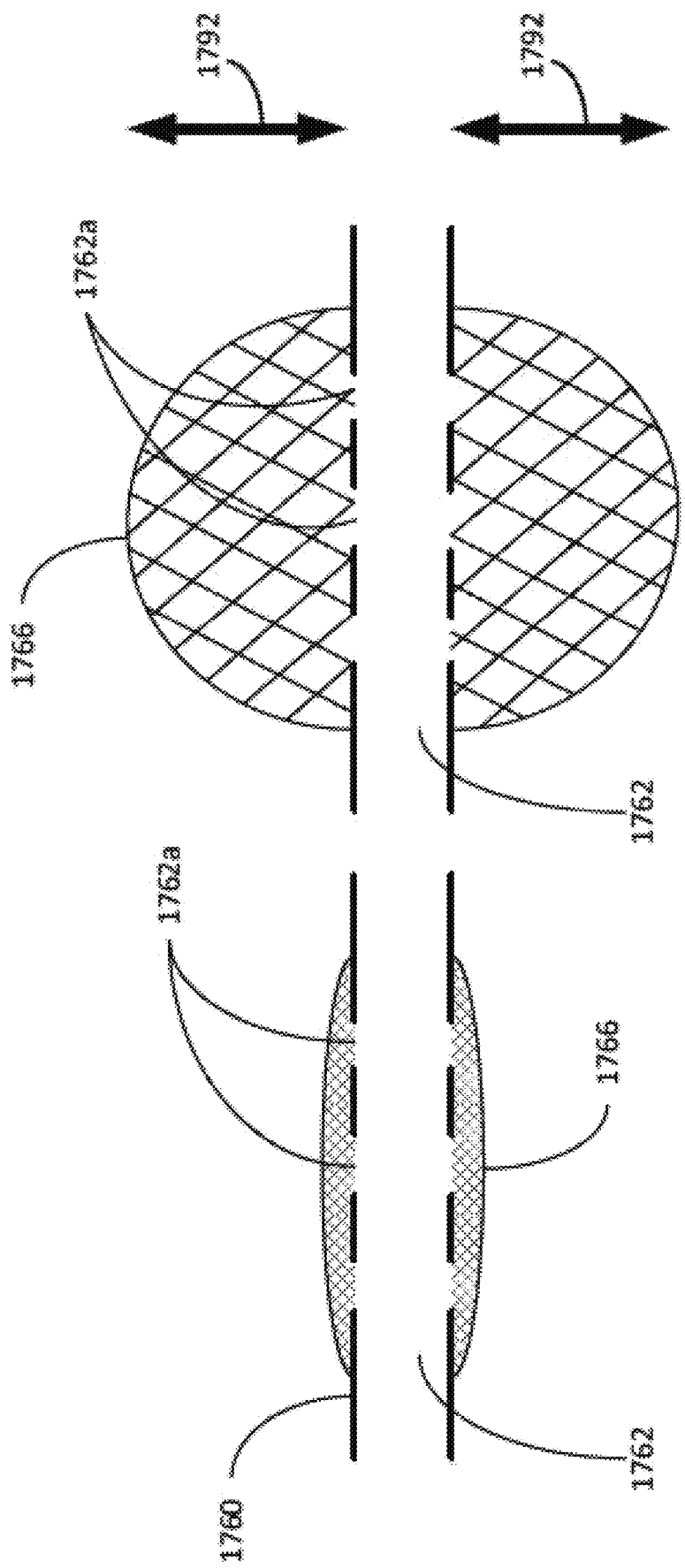

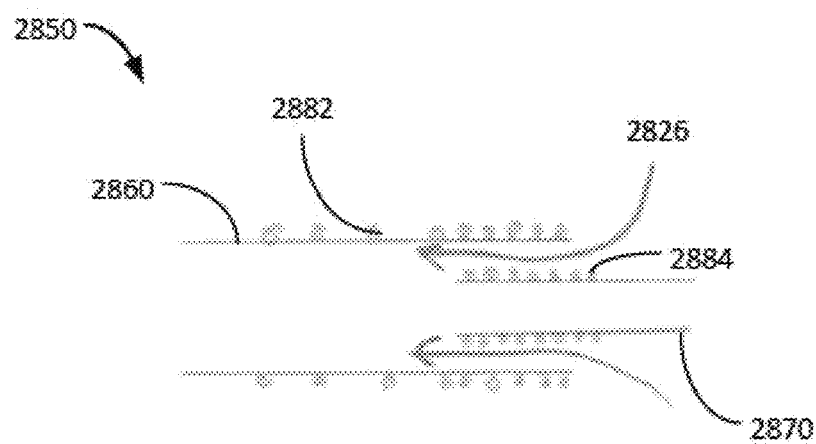
FIG. 28
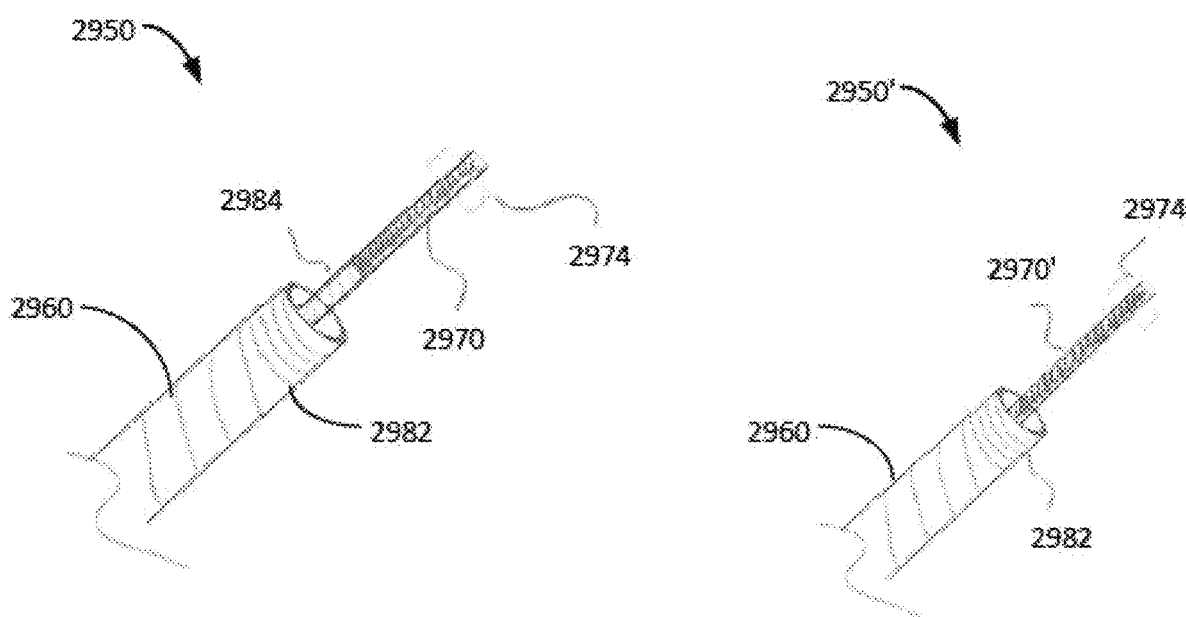
FIG. 29A
FIG. 29B

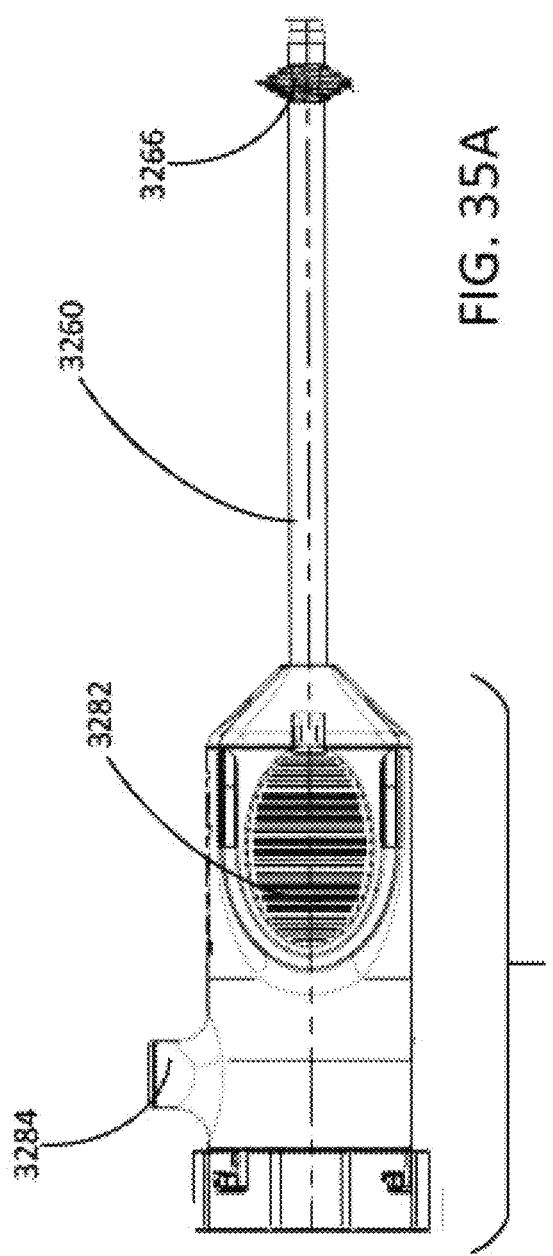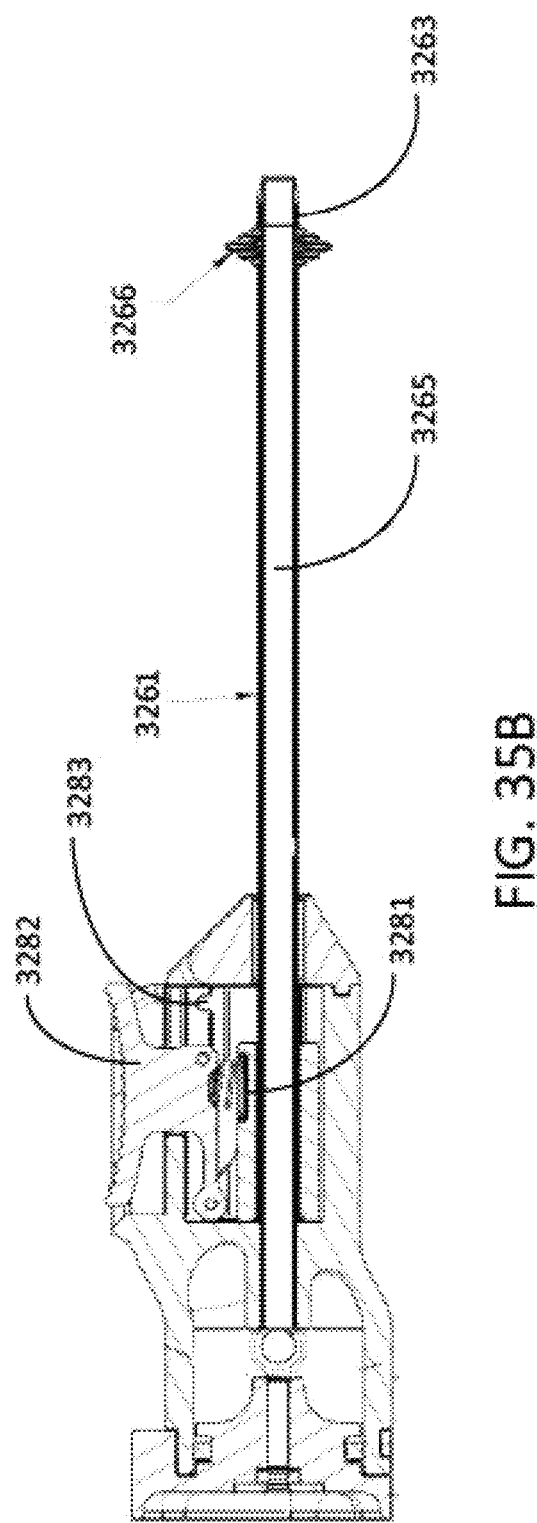

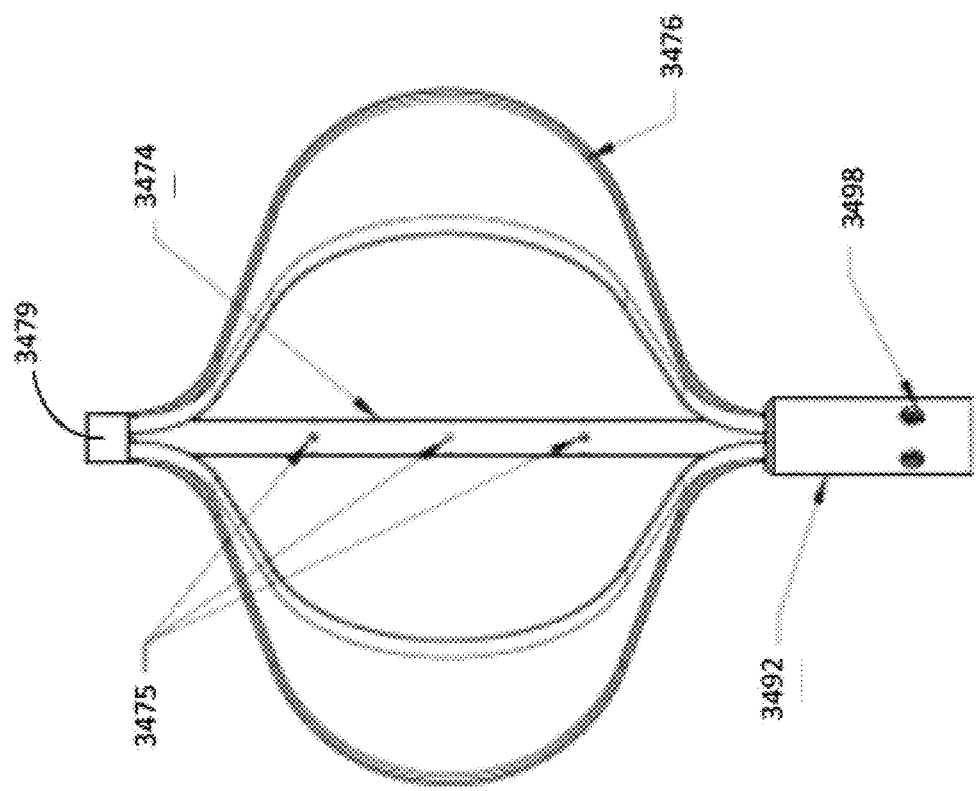
FIG. 37B

SYSTEMS, DEVICES, AND METHODS FOR ABLATION AND DEFUNCTIONALIZATION OF A GALLBLADDER

CROSS-REFERENCE TO RELATED APPLICATIONS

This application is a continuation of International Patent Application No. PCT/US2021/045987, entitled "SYSTEMS, DEVICES, AND METHODS FOR ABLATION AND DEFUNCTIONALIZATION OF A GALLBLADDER," filed Aug. 13, 2021 which claims the priority to and the benefit of U.S. Provisional Application No. 63/066,005, entitled "SYSTEMS, DEVICES, AND METHODS FOR ABLATION AND DEFUNCTIONALIZATION OF A GALLBLADDER," and filed on Aug. 14, 2020, the disclosure of each of which is hereby incorporated by reference in its entirety.

TECHNICAL FIELD

This present disclosure relates to devices and methods for ablation and defunctionalization of a gallbladder.

BACKGROUND

Medical ablation technologies, such as those used in cardiology, oncology, general surgery, gastroenterology, dermatology, and interventional radiology, focus on local tissue targets and, while providing a great degree of ablation depth control, may not be effective or practical for large, high-surface area (HSA) tissue ablation targets within a body. Cryoablation technologies leverage a generic cryogen spray to provide a platform for HSA tissue ablation, but have certain drawbacks associated with safely and effectively delivering energy within closed lumens, such as the gallbladder. For example, ice build-up or other complications during an ablation procedure can lead to injury and/or ineffective ablation. Accordingly, it is desirable to have systems, devices, and methods to address the drawbacks of existing ablation systems.

SUMMARY OF THE DISCLOSURE

The present disclosure relates to devices and methods for ablation and defunctionalization of a gallbladder. In some embodiments, an apparatus includes a shaft defining a lumen and having a distal portion disposable in a body lumen of a subject, the shaft including: a nozzle disposed on the distal portion, the nozzle defining a plurality of openings in fluid communication with the lumen, the nozzle configured to deliver an ablation medium into the body lumen; and an expandable structure disposed around the nozzle, the expandable structure configured to transition into an expanded state within the body lumen, the expandable structure including a plurality of elongate members that are configured, when the expandable structure is in the expanded state, to (1) position the nozzle from tissue within the body lumen by at least a predetermined distance and (2) allow the ablation medium to pass through the expandable structure to contact and ablate the tissue within the body lumen.

In some embodiments, an apparatus includes an outer shaft having a distal end disposable in a body lumen of a subject, the outer shaft defining a first lumen and a plurality of evacuation openings in fluid communication with the first lumen, the plurality of evacuation openings and the first lumen collectively configured to evacuate an ablation medium from the body lumen, the outer shaft including an expandable structure (1) disposed on the distal end of the outer shaft and (2) configured to transition into an expanded state to surround the plurality of evacuation openings and prevent debris from clogging the plurality of evacuation openings; and an inner shaft disposable within the first lumen and having a nozzle extendable distal to the outer shaft, the inner shaft defining a second lumen in fluid communication with the nozzle, the second lumen configured to deliver the ablation medium to the nozzle such that the nozzle can distribute the ablation medium throughout the body lumen to contact and ablate tissue within the body lumen.

In some embodiments, a method includes transitioning a first expandable structure disposed on a distal end of an outer shaft of an ablation catheter into an expanded state to retain the access sheath within a body lumen of a subject, the distal end of the outer shaft disposed within the body lumen, the outer shaft defining a first lumen; advancing a distal end of an inner shaft into the body lumen via the first lumen, the inner shaft defining a second lumen and including a nozzle and a second expandable structure disposed on the distal end of the inner shaft; transitioning the second expandable structure into an expanded state to position the nozzle at least a predetermined distance from tissue within the body lumen; conveying, via the second lumen, an ablation fluid to the nozzle; and dispensing the ablation fluid from the nozzle such that the ablation fluid transitions into an ablation gas that contacts and ablates the tissue within the body lumen.

BRIEF DESCRIPTION OF THE DRAWINGS

FIGS. 7A-7C are illustrations of different percutaneous and endoscopic access approaches for ablation systems, according to an embodiment.

FIGS. 17A-17B are illustrations of an outer shaft of an ablation catheter with evacuation openings, according to an embodiment.

FIG. 28 is a cross-sectional view of an ablation catheter with a catheter heating system, according to an embodiment.

FIGS. 29A-29B are illustrations of an ablation catheter with a catheter heating system, according to an embodiment.

FIGS. 35A-35B are an illustration of a sheath of an ablation catheter, according to an embodiment.

FIGS. 37A-37B are illustrations of a nozzle assembly, according to an embodiment.

DETAILED DESCRIPTION

Figure 1:
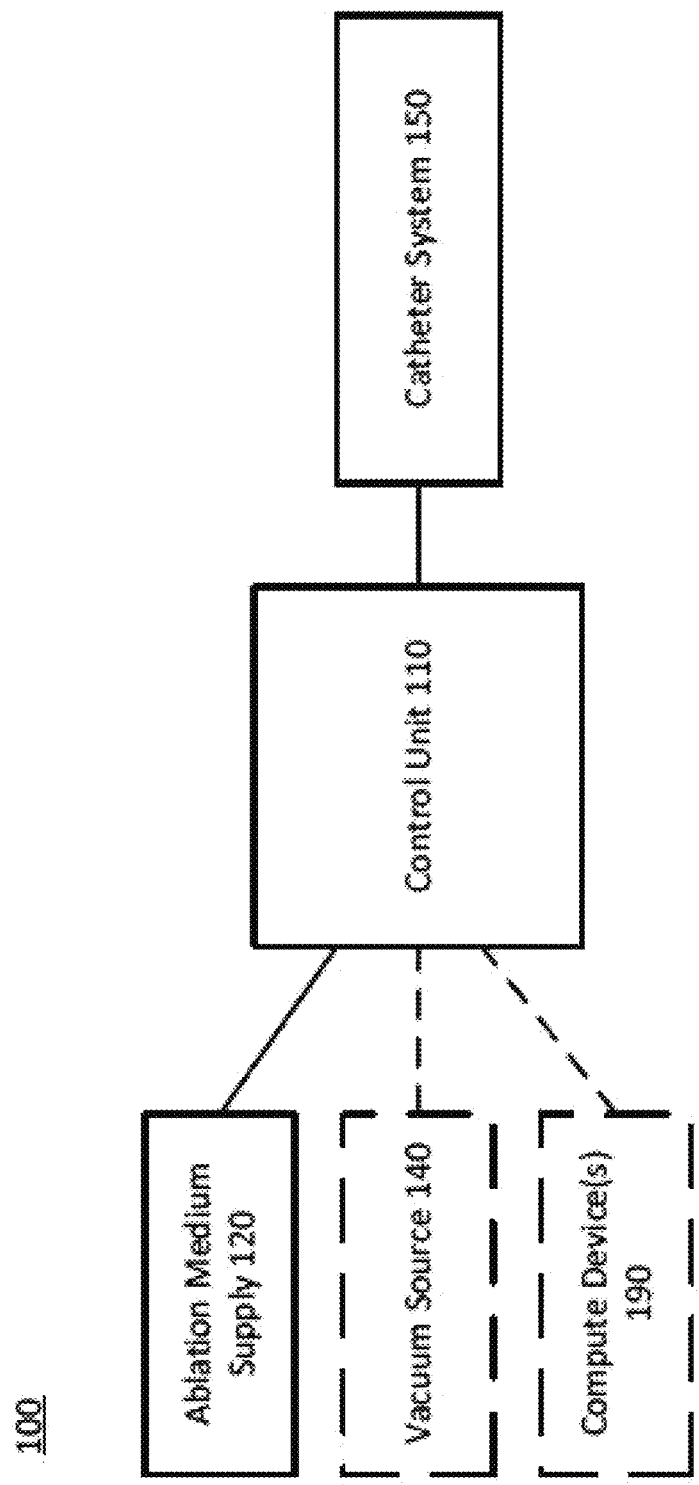
FIG. 1 is a schematic illustration of an ablation system (e.g., cryoablation device), according to an embodiment.

The present disclosure relates to ablation systems, devices, and methods for ablating a body lumen, such as, for example, a gallbladder lumen. In some embodiments, systems, devices, and methods described herein relate to cryoablation devices for tissue ablation. In some embodiments, systems, devices, and methods described herein relate to ablation medium release valves, e.g., for catheter-based cryoablation devices, that are designed to safely, effectively, and uniformly disperse an ablation medium (e.g., a cryogenic ablation medium) onto an area of interest (e.g., tissue lining a gallbladder lumen). In some embodiments, systems, devices, and methods described herein relate to controlling an operation of an ablation system based on sensor data, e.g., pressure and/or temperature data. In some embodiments, systems, devices, and methods described herein include sensors and/or can be used with sensors (e.g., of one or more probes) to track properties or conditions of a body lumen (e.g., a gallbladder lumen) and/or an ablation medium being delivered into the body lumen. Examples of suitable components of ablation systems, including cryoablation devices, are described in International Patent Application No. PCT/US2019/017112, entitled "GALLBLADDER DEFUNCTIONALIZATION DEVICES AND METHODS," filed on Feb. 7, 2019, and International Patent Application No. PCT/US2020/045436, entitled "SYSTEMS, DEVICES, AND METHODS FOR ABLATION AND DEFUNCTIONALIZATION OF A GALLBLADDER," filed on Aug. 7, 2020, each of which is incorporated by reference in its entirety.

Gallstones are one of the most common gastrointestinal disorders amongst Americans. Gallstones form when bile, a fluid secreted by the liver and stored in the gallbladder, becomes supersaturated. While they do not cause a problem for many people, gallstones occasionally block the cystic duct, i.e., an outlet of the gallbladder, preventing the gallbladder from emptying. In some instances, the obstruction results in pain, inflammation, and infection. In otherwise healthy patients, the gallstone disease is treated by surgical removal of the gallbladder. However, the risks associated with surgical treatment are considerably higher in certain patient populations. For example, one in five Medicare patients have been shown to suffer an adverse outcome. Non-surgical treatment options for these patients are limited and focus on relieving acute symptoms, without addressing the underlying cause of the disease. In some instances, the disease is likely to recur, resulting in additional clinical risk and significant cost. There currently is no long-term solution for gallbladder disease in high-risk patients.

As depicted in FIGS. 7A-7C, the gallbladder 2 is a small hollow organ in the gastrointestinal system. A blind-ended tubular outpouching of the biliary tree, the gallbladder 2 is a pear-shaped organ with a storage capacity of 30 milliliters (mL)-50 mL. The gallbladder is typically 2-3 centimeters (cm) in breadth and 7-10 cm in axial length. The gallbladder is typically divided into three parts: the fundus, body, and neck. The neck contains a mucosal fold, known as Hartmann's Pouch, which is a common location for gallstones to become lodged, resulting in cholecystitis. As shown in FIGS. 7A-7C, the gallbladder 2 opens into a cystic duct 14 and connects to the liver 8 by the common hepatic duct 18 which bifurcates into the right hepatic duct and the left hepatic duct. The gallbladder 2 is connected to the small intestine 10 by the common bile duct 16.

Histologically, the gallbladder has 4 layers, including the serosa (the outermost layer), a muscular layer, lamina propria, and the innermost mucosa layer. The mucosal layer of the gallbladder is the innermost layer of the gallbladder wall and concentrates the bile. The serosa is derived from the visceral peritoneum and covers the anterior fundus, body, and neck of the gallbladder. Inside the serosa, a single muscular layer envelopes the lamina propria. The mucosa that lines the inner lumen of the gallbladder is composed of columnar epithelial cells which secrete mucin and dehydrate bile via the action of multiple ion channels. Occasionally, outpouchings (known as Rokitansky-Aschoff nodules) of the mucosa extend into deeper layers of the gallbladder wall.

The gallbladder stores and concentrates the bile produced by the liver and releases the stored bile into the small intestine, where the bile helps in the digestion of fats in food. Bile is made by hepatocytes in the liver and subsequently secreted into hepatic ductules which coalesce into intrahepatic ducts. These ducts converge to form the right and left hepatic ducts which then combine into the common bile duct. The common bile duct joins with the pancreatic duct just proximal to the ampulla of Vater in the duodenal wall. Bile produced by hepatocytes flows through the biliary system and into the duodenal lumen to aid in digestion.

Flow into the duodenal lumen is regulated at the level of the ampulla of Vater by the sphincter of Oddi. During an unfed state, when bile is not needed for digestion, the sphincter is closed, resulting in routing of bile to the gallbladder for storage. During storage, bile becomes supersaturated, providing a nidus for the formation of gallstones and sludge (very small gallstones). The majority of gallstones are "brown stones," that are mainly comprised of cholesterol (typically >80%). These stones tend to be brittle and are readily crushed. A minority of stones are predominantly bilirubin ("black stones"; <20% cholesterol) and are often much harder. Mixed stones contain a variable amount of bilirubin and cholesterol.

Mobile gallstones that remain in the lumen of the gallbladder have the potential to cause various pathologies. In some instances, the gallstones become lodged at the neck of the gallbladder, occluding the cystic duct. The lodged gallstones cause gallbladder distension and intermittent right upper quadrant discomfort (likely from intramural muscle spasm at the organ attempts to empty against an increased pressure gradient), a condition known as symptomatic cholelithiasis. In some instances, the gallstones become lodged more permanently at the gallbladder outlet, resulting in inflammation and infection. This is a condition known as cholecystitis, which requires urgent intervention as it can progress to systemic infection.

Alternatively or in combination, gallstones or sludge passes through the cystic duct, becoming lodged in the common bile duct, blocking the flow of bile, resulting in a potentially life threatening condition known as ascending cholangitis. In some embodiments, the debris becomes lodged at the confluence of the pancreatic and common bile ducts, causing stagnation of pancreatic secretions, resulting in pancreatitis (inflammation of the pancreas).

In cholelithiasis, supersaturation of bile in gallbladder leads to the formation of gallstones. In some instances, impacted gallstones leads to inflammation, pain and infection of the gallbladder. When the gallbladder is inflamed, the mucosal layer of the gallbladder becomes more prominent. In some instances, the gallstone disease is diagnosed by ultrasounds or other imaging methods. Provided herein are methods and devices configured to definitively treat benign gallbladder disease in a minimally invasive manner in patients with symptomatic gallstones in order to reduce health care costs and patient morbidity.

Laparoscopic cholecystectomy is a treatment for gallstone disease and is a commonly performed general surgery procedure. During laparoscopic cholecystectomy, small incisions are made in the abdomen, facilitating the removal of the gallbladder with a camera and small instruments. The procedure is safe in otherwise healthy patients, and often does not require hospital admission. In uncomplicated cases, patients are often back to work within two weeks.

In a number of patient populations, the surgical risk associated with laparoscopic cholecystectomy is considerably higher. In some instances, these populations include critically ill patients, patients with intra-abdominal scarring from chronic disease and previous surgery, and elderly patients who tend to have a higher incidence of medical comorbidities. One such population is the Medicare population, which comprises approximately 200,000 laparoscopic cholecystectomies per year in the US. Twenty one percent of these surgeries result in an adverse outcome, including prolonged length of stay and readmission and other perioperative complications. In addition to the direct costs associated with these complications, many elderly patients are at risk of not returning to their baseline level of health, resulting in additional healthcare costs.

There are non-surgical options to treat gallstone disease. These include the administration of antibiotics, or placement of a cholecystectomy tube to drain the gallbladder contents, or a combination of the two. However, the non-surgical options do not provide a long-term solution. These options are effective temporizing measures, and they do not treat the cause of the disease. During a percutaneous cholecystectomy, a cholecystectomy tube is placed through the rib cage into the gallbladder. The percutaneous cholecystectomy can take place in an interventional radiology (IR) suite or at the patient's bedside but does not provide a definite treatment of the gallstone disease. Often times, the non-surgical options lead to recurrence and additional hospitalization costs.

For patients with cholecystitis who have a high risk of surgical complications, the treatment is percutaneous decompression of the gallbladder (via a percutaneously inserted cholecystectomy tube) in conjunction with antibiotics. This treatment provides a temporizing measure to allow the patient to recover from the systemic effects of the ongoing infection (sepsis) and return to their baseline state of health (commonly referred to as "cooling off" by healthcare professionals). The cholecystectomy tube remains in place until the patient has recovered. About 6-8 weeks following placement, a cholangiography by injection of radiopaque contrast through the tube under fluoroscopy is performed to determine if the cystic duct is patent (open). The cholecystectomy tube is removed if the cystic duct is patent. The treatment is interval cholecystectomy as it reduces the rate of recurrence of the gallstone disease. If there is no communication between the cystic duct and the common bile duct, the tube remains in place until cholecystectomy is performed, or patency is demonstrated on subsequent cholangiography. There is no definitive treatment available for high risk patients, placing them at risk for disease recurrence and exposure to the associated clinical risks and healthcare costs.

Ablation technologies have been used to treat other diseases. For example, ablation has been used in treatment of esophageal metaplasia and endometrial hyperplasia. However, ablation technologies are not readily available for treating gallstone disease. Ablation technologies often are applied to a small targeted area, such as a nerve, and are not typically used for applying to a diffuse area or a tissue or organ. Systems, devices, and methods described herein relate to ablating and defunctionalizing a gallbladder, and are specifically designed to safely and efficiently ablate the gallbladder.

FIG. 1 is a schematic illustration of an example ablation system 100, according to an embodiment. The ablation system 100 includes a control unit 110, a catheter system or ablation catheter 150, and an ablation medium supply 120. The control unit 110 can control the operation of one or more components of the ablation system 100.

The control unit 110 can be operatively coupled to the ablation medium supply 120, which provides a supply of an ablation medium. For example, the control unit 110 can be configured to control delivery of the ablation medium into a body lumen (e.g., gallbladder lumen). In some embodiments, the ablation medium is a cryogenic ablation medium. In some embodiments, the cryogenic ablation medium is a liquid. In some embodiments, the cryogenic ablation medium is a gas. In some embodiments, the cryogenic ablation medium undergoes a liquid-to-gas phase transition when being delivered using the systems and devices disclosed herein. In some embodiments, cryoablation is achieved via the refrigerant property due to the liquid to gas phase change from an ablation medium, such as liquid nitrous oxide, carbon dioxide, and argon. In some embodiments, the cryogenic ablation medium is one or more of nitrous oxide, nitrogen, carbon dioxide, or argon. In some embodiments, the cryogenic ablation medium can transition from a first state (e.g., a liquid) to a second state (e.g., a gas) and increase up to about 600 times an original volume of the cryogenic medium during the transition. In some embodiments, the control unit 110 can control one or more of a temperature, a pressure, etc. of the ablation medium. In some embodiments, an ablation medium such as a cryogenic ablation medium ranges from about −120 degrees Celsius to about 0 degrees Celsius, including all values and subranges in between, when the cryogenic ablation medium is used with the systems and devices disclosed herein. In some embodiments, the ablation medium supply 120 can be a cryogen cartridge.

The control unit 110 can optionally be coupled to a vacuum source 140 (e.g., a vacuum or suction pump, an aspirator, etc.). In some embodiments, the control unit 110 can control the vacuum source 140 to apply a vacuum to a channel or lumen of the catheter system 150, e.g., to remove or evacuate an ablation medium from within a body lumen (e.g., gallbladder lumen). For example, the control unit 110 can activate the vacuum source 140 to apply negative pressure within a lumen of the catheter system 150 to evacuate a portion of an ablation medium, such as a cryogenic ablation medium, that has been delivered to the body lumen. Alternatively, in some embodiments, the ablation system 100 does not include a vacuum source 140, and ablation medium can be evacuated from a body lumen via passive evacuation driven by a pressure differential between an interior of the body lumen and an exterior environment. For example, when an ablation medium such as a cryogenic ablation medium is delivered into a body lumen, the ablation medium can increase pressure within the body lumen relative to an environment exterior to the body lumen (e.g., an exterior atmosphere), and that pressure differential can drive evacuation of a portion of the ablation medium out of the body lumen, e.g., via a lumen defined by the catheter system 150.

In some embodiments, the control unit 110 can include or be operatively coupled to one or more sensors (e.g., pressure sensors, temperature sensors), and can operate or control one or more components of the ablation system 100 based on data collected by the one or more sensors. For example, the control unit 110 can be coupled to a pressure sensor and, based on measurements from the pressure sensor, control delivery of the ablation medium (e.g., from ablation medium supply 120) and evacuation of the ablation medium (e.g., using vacuum source 140) to maintain pressure within a body lumen within a predetermined range of pressures. Stated differently, the control unit 110 can be configured to control insufflation of a body lumen such that pressure within the lumen is maintained within a predetermined range of pressures. In some embodiments, the predetermined pressure range is less than 50 mmHg, or less than 100 mmHg. In some embodiments, the predetermined pressure range is about 0 mmHg to about 40 mmHg, or about 30 mm Hg to about 40 mm Hg. In some embodiments, the control unit 110 can be operatively coupled to one or more valves, which the control unit 110 can control to allow and/or terminate delivery or evacuation of an ablation medium. Examples of suitable valves are described in International Patent Application No. PCT/US2020/045436, incorporated herein by reference.

In some embodiments, the control unit 110 and/or other components of the ablation system 100 can optionally be coupled to one or more additional compute devices 190. Compute device(s) 190 can be can be any suitable processing device configured to run and/or execute certain functions. The one or more compute device(s) 190 can include, for example, a computer, a laptop, a portable device, a mobile device, or other suitable compute device including a processor, a memory, and/or an input/output device. For example, the control unit 110 can be coupled to a remote compute device, such as a workstation, through which a user (e.g., physician, administrator, etc.) can control one or more operational parameters of the ablation system 100. The control unit 110 and the one or more compute device(s) 190 can be configured to send data and/or receive data from one or more other compute device(s) 190, e.g., via a network. For example, the control unit 110 can send alerts and/or other information to a remote device (e.g., a display, a mobile device) such that the remote device can present that information to a user (e.g., a physician). In some embodiments, the control unit 110 can send data such as patient information, operational status of one or more components of the ablation system 100, etc.

In some embodiments, the control unit 110, ablation medium supply 120, and/or other components of the ablation system 100 can be integrated into a handheld device that is attached to a proximal end of the catheter system 150. The handheld device can include on or more input and/or output devices (e.g. buttons, switches, keyboards, touchscreens, display, etc.) through which an operator of the ablation system 100 can control the operation of the ablation system 100 to perform an ablation procedure. In some embodiments, the control unit 110 can be remote from the catheter system 150, and a remote operator can control one or more components of the ablation system 100 to perform an ablation procedure.

The catheter system 150 can be percutaneously inserted into a body lumen (e.g., a gallbladder lumen) to scar down and defunctionalize portions of anatomy (e.g., the gallbladder) without the need for surgical removal of the anatomy. The catheter system 150 can be used in the interventional radiology (IR) suite and with local anesthesia, eliminating the risks associated with general anesthesia in high risk surgical patients. Placement of the device leverages existing IR workflows and can be deployed in a manner similar to existing devices. For example, for placement in the gallbladder lumen, such placement can be similar to a cholecystectomy tube or percutaneous gallbladder drainage tube.

Figure 2:
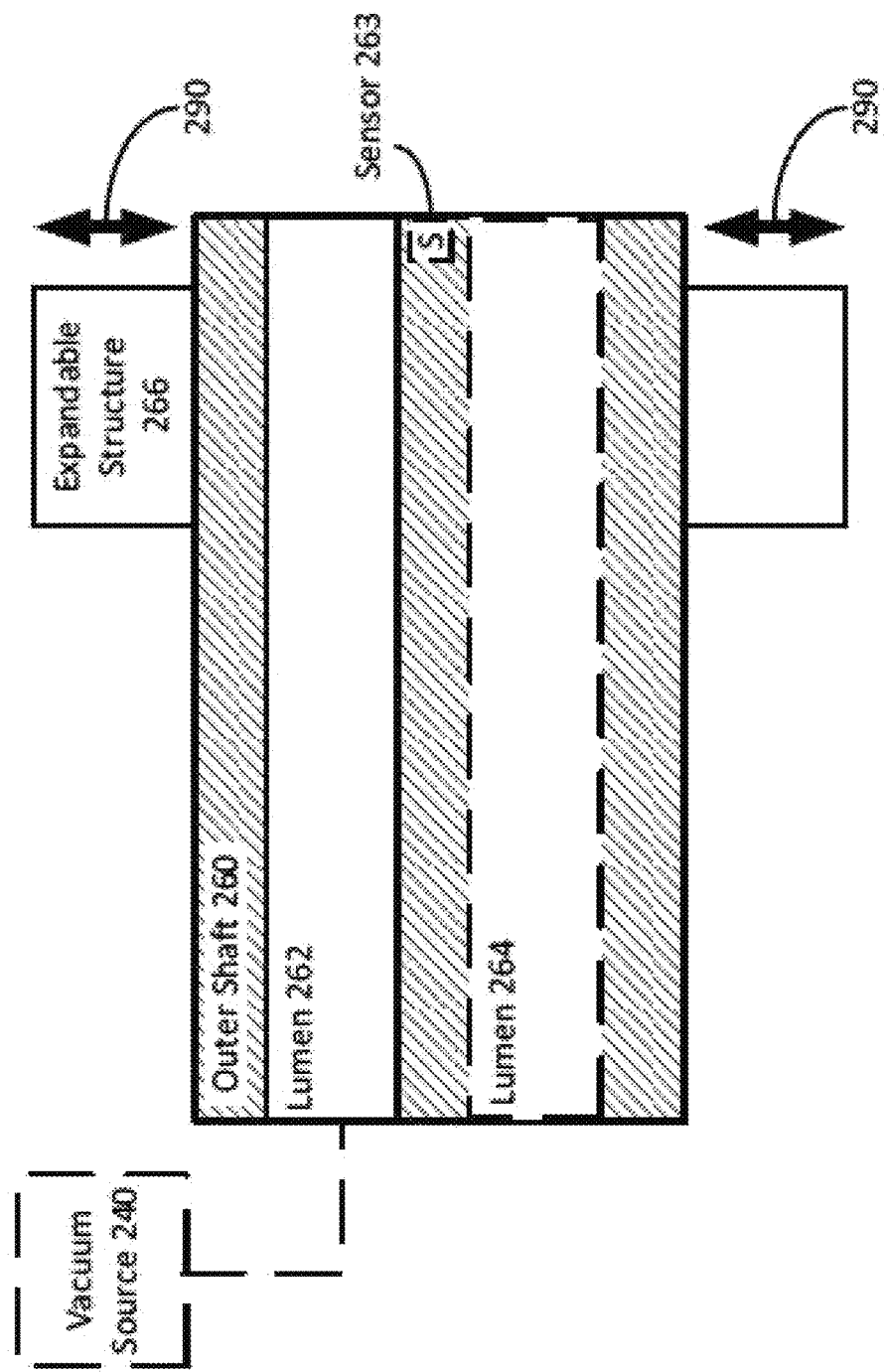
FIG. 2 is a schematic illustration of an outer shaft of a catheter system, according to an embodiment.
Figure 3:
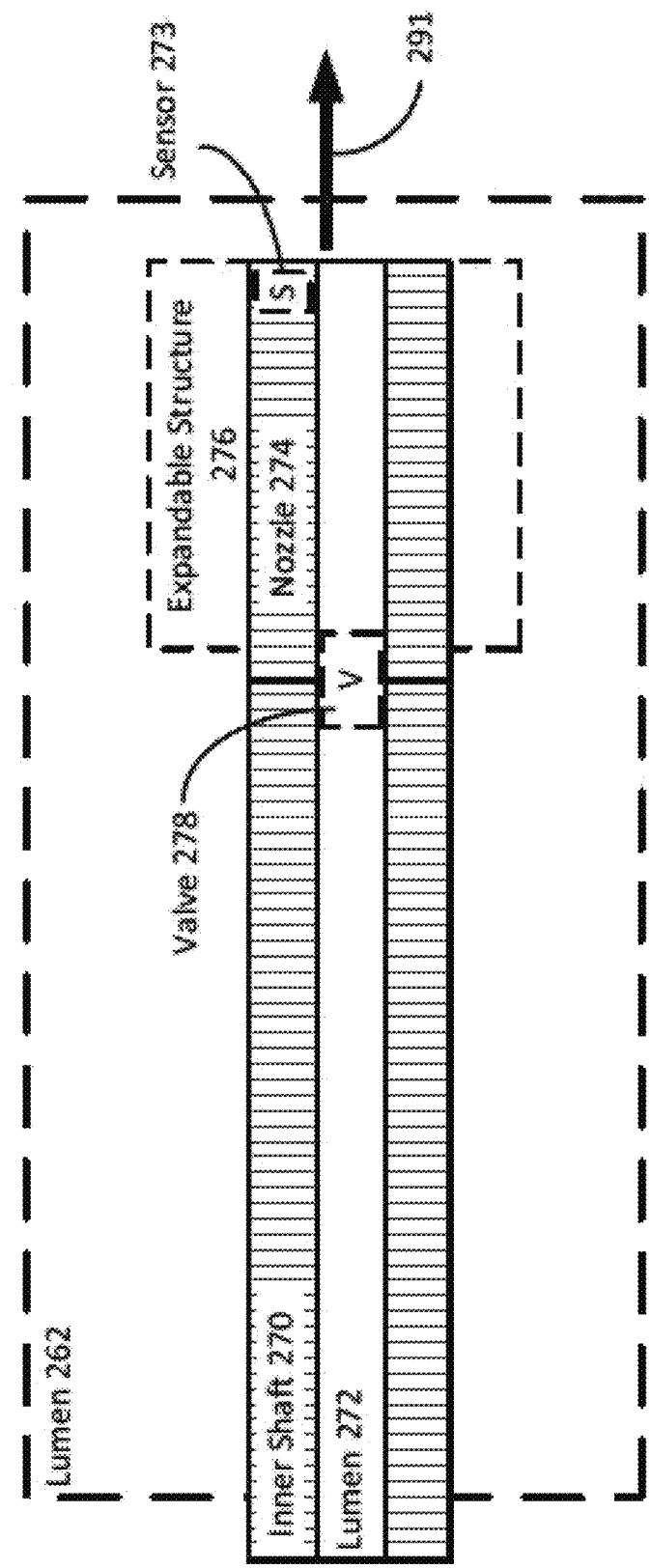
FIG. 3 is a schematic illustration of an inner shaft of a catheter system, according to an embodiment.
Figure 4:
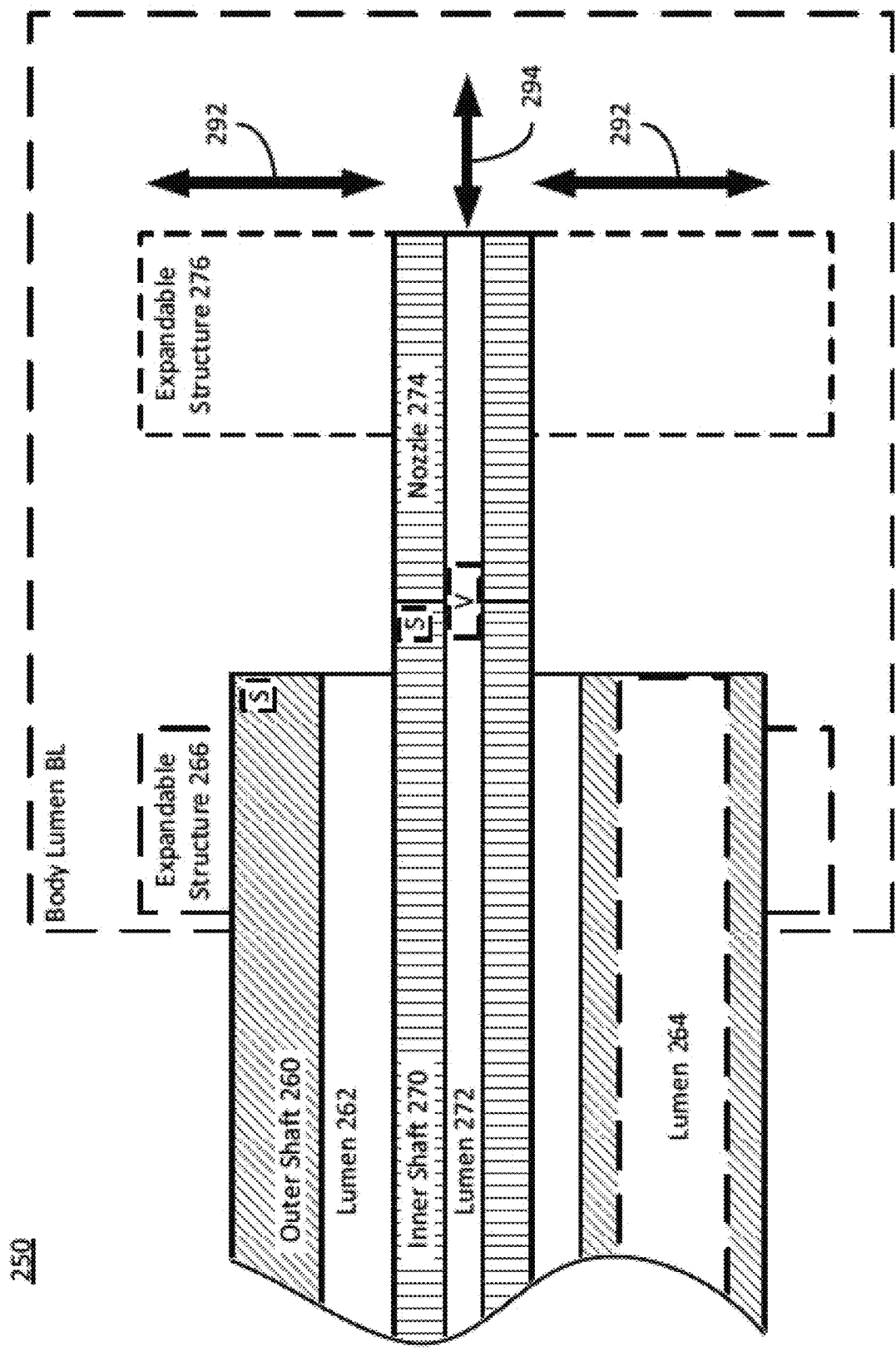
FIG. 4 is a schematic illustration of a catheter system, according to an embodiment.

FIGS. 2-4 provide schematic views of portions of an example catheter system 250, according to some embodiments. Catheter system 250 can be structurally and/or functionally similar to catheter system 150. For example, catheter system 250 can be coupled to a control unit (e.g., control unit 110) and/or be configured to receive an ablation medium from an ablation medium supply (e.g., ablation medium supply 120). The catheter system 250 can include an outer shaft 260 and an inner shaft 270. The inner shaft 270 can also be referred to as a first shaft, and the outer shaft 260 can be referred to as a second shaft. In some embodiments, the outer shaft 260 and the inner shaft 270 can be separate components that are used together, e.g., to perform an ablation procedure. For example, the outer shaft 260 can be implemented as an access sheath or introducer, and the inner shaft 270 can be implemented as a catheter that is insertable into a lumen of the introducer. In some embodiments, the outer shaft 260 and the inner shaft 270 can be integrated into a single catheter device, e.g., a device having two concentric shafts.

FIG. 2 provides a detailed view of the outer shaft 260. The outer shaft 260 can be, for example, an access sheath. The outer shaft 260 can define a lumen 262. The lumen 262 can be configured to receive one or more instruments, including, for example, the inner shaft 270. The outer shaft 260 can be configured to provide access to a body lumen BL (e.g., a gallbladder lumen). For example, a distal end of the outer shaft 260 can be positioned within a body lumen BL, as schematically depicted in FIG. 4. Once positioned inside the body lumen BL, the outer shaft 260 can enable delivery of one or more instruments into the body lumen BL, e.g., via lumen 262. For example, as depicted in FIG. 4, the inner shaft 270 can be inserted into lumen 262 of the outer shaft 260 and navigated into the body lumen BL such that a distal end of the inner shaft 270 is positioned inside of the body lumen BL.

In some embodiments, the lumen 262 can be configured to evacuate or drain fluids (e.g., liquids or gases) and/or debris (e.g., gallstones or fragments thereof, tissue, etc.) from within the body lumen BL. For example, the lumen 262 can allow an ablation medium (e.g., a cryogenic ablation medium) delivered to the body lumen BL to be evacuated from the body lumen BL. In some embodiments, the lumen 262 can be operatively coupled to a vacuum source 240, which can be activated to apply negative pressure within lumen 262 to evacuate fluid from within the body lumen BL. Alternatively, the lumen 262 can function as a passive evacuation passageway for fluid to exit the body lumen BL. For example, as ablation medium is delivered into the body lumen BL and pressure increases within the body lumen BL relative to an exterior of the shaft 260, such pressure can passively drive a portion of the ablation medium out from the body lumen BL via lumen 262.

In some embodiments, the outer shaft 260 can define one or more additional lumens, e.g., a lumen 264, which can be structurally and/or functionally similar to lumen 262. For example, lumen 264 can also be configured to provide access into the body lumen BL. In some embodiments, lumen 262 can be configured to receive the inner shaft 270 and lumen 264 can be configured to receive a different surgical and/or monitoring device (e.g., a probe, a second ablation device, etc.). In some embodiments, one or more of lumens 262, 264 can be fluidically coupled to a sensor (e.g., a pressure sensor) to allow for pressure measurements of the body lumen BL and/or other portions of the body. For example, a sensor integrated into a control unit (e.g., control unit 110) can be in fluid communication with one or more of lumens 262, 264 and take measurements (e.g., pressure measurements) of an environment within the outer shaft 260 and/or body lumen BL.

In some embodiments, the outer shaft 260 optionally includes a sensor 263. In some embodiments, the sensor 263 can be located in a distal portion of the outer shaft 260 that is configured to be disposed within the body lumen BL. Alternatively, the sensor 263 can be disposed at a different location along the outer shaft 260, including, for example, within a lumen (e.g., lumen 262, 264), at a proximal end at the outer shaft 260, etc. The sensor 263 can be configured to capture information about an environment within the body lumen BL or other environment within and/or surrounding the outer shaft 260. For example, the sensor can be configured to measure a property (e.g., pressure, temperature) of an ablation medium being delivered to the body lumen BL, a property (e.g., pressure, temperature) of the body lumen BL or fluid within the body lumen BL, etc. The sensor 263 can include, for example, a pressure sensor (e.g., pressure transducer, strain gauge transducer, diaphragm displacement sensor, optical fiber pressure sensor, solid state sensor), temperature sensor, light sensors, gas sensors, etc. In some embodiments, sensor 263 can be coupled to a control unit (e.g., control unit 110) and/or other compute device (e.g., compute device 190) via a wired connection, such as, for example, a wire that is coupled to and/or disposed within the outer shaft 260. In some embodiments, the sensor 263 can be configured to wirelessly transmit data, e.g., indicative of one or more measured properties of the body lumen BL, to control unit and/or another compute device.

In some embodiments, the outer shaft 260 can include a tapered portion or tapered end at the distal end of the outer shaft 260. In some embodiments, a dilator can be inserted into a lumen of the outer shaft 260 (e.g., lumen 262) to aid in insertion of the outer shaft 260 into the body lumen BL. The dilator can be positioned in the lumen such that a distal end of the dilator extends distally from the outer shaft 260. In such instances, the tapered end of the outer shaft 260 can form a smooth transition from the outer shaft 260 to an outer surface of the dilator to aid in insertion into the body lumen BL, rather than having a sudden step in the profile of the device during insertion into the body lumen BL. Further details with respect to using a dilator with the outer shaft 260 are provided with reference to FIGS. 6A-6B.

In some embodiments, the outer shaft 260 includes an expandable structure or body 266 that can be deployed within the body lumen BL, e.g., transitioned from an undeployed state or configuration to a deployed or expanded state or configuration. The expandable structure 266 can be configured to prevent dislodgement and/or create a seal between the outer shaft 260 and the body lumen BL. In use, the outer shaft 260 can be advanced, e.g., along a guidewire, until a distal end of the outer shaft 260 is positioned within the body lumen BL through an opening. The expandable structure 266 can then be deployed (e.g., expanded, inflated), as schematically shown in FIG. 2 by arrows 290. Once deployed (e.g., once in its deployed state), the expandable structure can have a diameter larger than an diameter of the opening through which the outer shaft 260 has been placed and therefore be configured to retain the outer shaft 260 within the body lumen BL. In some embodiments, the expandable structure 266 includes an inflatable balloon, a shape memory structure (e.g., a deployable nitinol structure), etc. In some embodiments, the expandable structure 266 in its deployed state can have an outer diameter that is about 1.5 times to about 3 times larger than an outer diameter of the outer shaft 260.

In some embodiments, the expandable structure 266 can transition from an undeployed state to a deployed state via compression of a portion of the outer shaft 260 and/or movement of an inner shaft relative to an outer shaft. For example, the expandable structure 266 can be bounded within a region along the length of the outer shaft 260 between two boundary rings, and the expandable structure 266 can deploy (e.g., expand) upon bringing the two boundary rings closer together. In some embodiments, the outer shaft 260 can be formed of or include multiple concentric tubes or tubular members, e.g., an inner tubular member can be translated relative to an outer tubular member to move the ends of the expandable structure 266 closer to one another to expand the expandable structure 266 (e.g., to deploy the expandable structure 266). In such embodiments, at least one end of the expandable structure 266 (e.g., a proximal end) can be coupled to an outer tubular member and the other end of the expandable structure 266 (e.g. distal end) can be coupled to an inner tubular member, and translation of the inner tubular member relative to the outer tubular member can cause expansion or deployment of the expandable structure 266. In some embodiments, the expandable structure 266 can be pre-shaped to expand into its deployed state. For example, the expandable structure 266 can be held in tension (e.g., held in its undeployed state by an outer sleeve or tubular member, or stretched flat along an outer surface of the outer shaft 260 by a tubular member or pull wire), and when released, can self-expand into its deployed state.

In some embodiments, the expandable structure 266 can include elongate members (e.g., bands, fibers, wires, splines) arranged in a woven or braided pattern. In some embodiments, the elongate members can be bent to form a bulb-like shape upon transitioning of the expandable structure 266 from an undeployed state to a deployed state. In some embodiments, linear compression of one end of the elongate members relative to the opposite end of the elongate members, can expand the expandable structure 266 outward, creating a geometry with an expanded diameter. In some embodiments, the expandable structure 266 can have a larger diameter in the deployed state in comparison to the undeployed state. This expansion can aid in inhibiting unintentional removal of the expandable structure 266 from the body lumen BL. In some embodiments, the expandable structure 266 can be composed of nitinol, stainless steel, a polymer, or any suitable material that has a high strain relief. In some embodiments, the expandable structure 266 can be formed of shape-memory material, such as, for example, shape memory Nitinol.

In some embodiments, the expandable structure 266 can function as a seal that seals an opening through which the ablation catheter 250 is disposed. Further details of suitable expandable structures 266 implemented as a seal are described in International Patent Application No. PCT/US2019/017112, incorporated herein by reference.

While two lumens (e.g., lumens 262, 264) are depicted in FIG. 2, it can be appreciated that the outer shaft 260 can include any number of lumens, including a single lumen and/or more than two lumens. The outer shaft 260 can also include additional sensors, expandable structures, etc. according to embodiments described herein.

FIG. 3 provides a more detailed view of the inner shaft 270 disposed in the lumen 262. The inner shaft 270 can be deployed from the outer shaft 260 and the lumen 262 via movement in an axial direction (e.g., translation along a longitudinal axis of the outer shaft 260), as depicted by arrow 291. The inner shaft 270 can be, for example, an ablation delivery device or ablation catheter. In some embodiments, the inner shaft 270 can form a portion of a cryoablation device and be configured to deliver a cryogenic ablation medium into the body lumen BL. The inner shaft 270 can be configured to provide an ablative energy or an ablative medium capable of killing cells within the body lumen BL. For example, the inner shaft 270 can be configured to provide an ablative energy or ablative medium capable of killing cells in a mucosal layer of a gallbladder lumen, killing cells lining a cystic duct, or any combination thereof. The ablative energy or medium can include, for example, a chemical agent (e.g., an antibiotic, a liquid sclerosant, sodium tetradecyl sulphate, acetic acid, ethanol, hypertonic sodium chloride, urea), a cryogenic ablation medium (e.g., a cryogenic liquid or gas), thermal ablation, electrical ablation, etc. In some embodiments, the inner shaft 270 can be configured to deliver multiple types of ablative energies or mediums. The inner shaft 270 can be configured to provide ablation that is spatially diffuse. Stated differently, the inner shaft 270 can be configured to provide ablation that ablates a large area of a body lumen BL. In some embodiments, the inner shaft 270 can be configured to deliver ablation for defunctionalizing gallbladder mucosa, for ablating or sclerosis of a cystic duct, or any combination thereof.

In some embodiments, the inner shaft 270 can be configured to deliver thermal ablation, cryoablation, chemical ablation, or any combination thereof. In some embodiments, cryoablation involves delivering a low temperature fluid to wall of the gallbladder, such as liquid nitrogen. In some embodiments, cryoablation involves delivering an ablation medium to the gallbladder wall that induces low temperatures due to phase change, such as nitrous oxide or carbon dioxide. In some embodiments, thermal ablation involves delivering a high temperature fluid to the wall of the gallbladder, such as, for example, hot water or steam. In some embodiments, the ablative medium is delivered in a liquid form, a gaseous form, an aerosol form, a gel form, or any combination thereof.

The inner shaft 270 can define a lumen 272. The lumen 272 can be configured to deliver an ablation medium, e.g., from ablation medium supply 120, to a nozzle 274 that is disposable within the body lumen BL. The nozzle 274 can be configured to release the ablation medium into the body lumen BL. In some embodiments, the nozzle 274 can include a plurality of openings or fenestrations for distributing the ablation medium throughout the body lumen BL. In some embodiments, the lumen 272 and nozzle 274 can be configured to convey a cryogenic ablation medium in a liquid state into the body lumen BL. The lumen 272 and nozzle 274 can be configured with dimensions that maintain a set amount of pressure on the cryogenic ablation medium such that the medium does not undergo a liquid-to-gas transition until the ablation medium exits the openings of the nozzle 274. Stated differently, the lumen 272 and nozzle 274 can be configured to convey a cryogenic ablation medium in a liquid state to the openings of the nozzle 274, at which point the release of the cryogenic ablation medium into the body lumen BL results in the cryogenic ablation medium changing from the liquid state into a gas state. In some embodiments, the lumen 272 of the inner shaft 270 can have a diameter from about 0.001 inches to about 0.1 inches, including all values and subranges in between.

In some embodiments, the inner shaft 270 can include an expandable structure or body 276. In some embodiments, the expandable structure can be disposed about the nozzle 274. In some embodiments, the expandable structure 276 can expand within the body lumen BL, such that the nozzle 274 is centered within the body lumen BL. In other words, the expandable structure 276 can expand outward to a desired diameter, such that a radial distance from the center of the nozzle 274 to the walls of the body lumen BL is consistent or approximately consistent in all radial directions. This consistent spacing or centering can ensure a minimum radial distance between the nozzle 274 and nearby tissue of the body lumen BL and/or more even distribution of the ablation medium through the body lumen BL. This can allow for ablation of luminal tissue, while ensuring that the ablation medium is not too close of a range (e.g., creating a sticking or perforation risk) or too far of a range (e.g., reducing the effectiveness of the ablation) from a section of tissue.

In some embodiments, the profile and/or the thermal mass of the expandable structure 276 can be minimized to allow for more efficient passage of ablation medium from the nozzle 274 to the surfaces of the body lumen BL. In other words, reducing or minimizing both the physical size and the amount of heat energy the expandable structure 276 can absorb or radiate can improve the efficiency of heat transfer during ablation. In some embodiments, the expandable structure 276 can be composed of Nitinol, stainless steel, a polymer, or any suitable material that has a high strain relief. In some embodiments, the material of the expandable structure 276 can be selected based on the material's ability to withstand cryogenic temperatures without significantly altering the cooling performance of the catheter system 250. In some embodiments, the use of an expandable structure 276 can avoid the creation of a significant apposition force between the expandable structure 276 and the body lumen BL, contrary to cryoablation balloon catheters. This can create a more effective cooling method that is less sensitive to the contents and geometry of the body lumen BL.

In some embodiments, the expandable structure 276 can be collapsible or retractable, such that the inner shaft 270 can be removed from the body lumen BL. In some embodiments, the expandable structure 276 can be radially symmetrical in order to ensure equidistant or approximately equidistant radial spacing of the walls of the body lumen BL around the outside of the nozzle 274.

In some embodiments, the expandable structure 276 can transition from an unexpanded state (e.g., undeployed state) to an expanded state (e.g., deployed state) via compression of a portion of the inner shaft 270 and/or movement of one portion of the inner shaft 270 relative to another portion of the inner shaft 270. In some embodiments, the expandable structure 276 can include elongate members (e.g., bands, wires, fibers, splines) arranged in a woven or braided pattern or arranged individually along a length of the inner shaft 270. For example, the expandable structure 276 can include one or more elongate members that generally extend along a length of the inner shaft 270. In some embodiments, the expandable structure 276 can include a single expandable elongate member, while in other embodiments, the expandable structure can include between 2 or 20 elongate members, including all values and subranges in-between. In some embodiments, a distal end of the expandable structure 276 can move toward a more proximal point of the expandable structure 276, causing the expandable structure 276 to expand, i.e., to transition from an undeployed state or configuration to a deployed state or configuration. In some embodiments, the inner shaft 270 can move relative to a sleeve or tubular member (not shown) to cause the expandable structure 276 to expand and contract. For example, the sleeve can be used to hold the expandable structure 276 in an undeployed state or the sleeve can move one end of the expandable structure 276 (e.g., a proximal end) relative to the other end of the expandable structure 276 (e.g., a distal end) to expand the expandable structure 276 into its expanded state. In some embodiments, the expandable structure 276 can include a plurality of wires or bands that extend along the length of the inner shaft 270, such that the wires or bands can be advanced and retracted from a proximal end of the ablation catheter 250. Such advancement and retraction can be used to deploy and undeploy the expandable structure 276. Further details of mechanism of expandable structures 276 are described with reference to later figures, including, for example, FIGS. 13A-13C and FIGS. 32A-32C.

In some embodiments, the inner shaft 270 can optionally include a valve 278. The valve 278 can be configured to control delivery of the ablation medium into the body lumen BL. For example, the valve 278 can be configured to turn on or shut off supply of the ablation medium into the nozzle 274. In some embodiments, a control unit (e.g., control unit 110) can be configured to control opening and/or closing of the valve 278. In some embodiments, a mechanical actuator (e.g., coupled to a handheld device, as described above) can be used to open and/or close the valve 278. In some embodiments, the valve 278 can be configured to close (e.g., automatically and/or via control by a control unit) in response to a pressure within the body lumen BL being greater than a predetermined threshold. In some embodiments, a sensor (e.g., sensor disposed on inner or outer shaft 260, 270 and/or sensor coupled to control unit 110) can be used to measure the pressure within the body lumen BL and control the valve 278 to open and/or close. In some embodiments, the valve 278 can be configured to close in response to a pressure difference between the body lumen BL and an evacuation lumen (e.g., lumen 262), e.g., indicating that a blockage or obstruction has formed along an evacuation pathway. For example, multiple sensors can be configured to measure different pressures associated with the catheter system 250 and/or body lumen BL, and a control unit (e.g., control unit 110) can be configured to analyze when such pressure measurements to determine when an unexpected obstruction has isolated any fluid flow paths into and/or out of the body lumen BL.

As noted above, in some embodiments, the inner shaft 270 can be or form part of a cryoablation device and be configured to deliver a cryogenic ablation medium into the body lumen BL. The cryoablation device can leverage the phase-change properties of certain cryogenic ablation mediums (e.g., liquid nitrous oxide) to induce cryoablation temperatures at a target tissue interface. When such cryogenic ablation mediums transition from liquid to gas, they expand in volume and can cause increase in pressure within the body lumen BL. Therefore, one important consideration in designing systems and devices disclosed herein lies in the monitoring and control of the intraluminal pressure in the body lumen BL during an ablation procedure. For example, systems and devices disclosed herein can be configured to ensure that intraluminal pressure does not increase above a predetermined threshold and/or lies within a predetermined range. In instances where there is an increase in intraluminal pressure (e.g., pressure above a predetermined threshold, or sudden change in pressure above a predetermined rate), systems and devices disclosed herein can be configured to evacuate air, gaseous cryoablation medium, and/or other fluids from within the body lumen BL to reduce the intraluminal pressure. In such instances, it can be important to ensure to any cryogenic ablation medium within the catheter system 250 (e.g., within lumen 272 of the inner shaft 270) and/or supply line into the catheter system 250 does not exit the catheter system 250 (e.g., nozzle 274) into the body lumen BL, further adding to the pressure increase. Accordingly, it can be desirable to minimize or reduce the amount of residual cryogenic ablation medium that is delivered into the body lumen BL in response to detecting a pressure increase event (e.g., pressure above a predetermined threshold, or sudden change in pressure above a predetermined rate). In some embodiments, the valve 278 can be used to reduce the amount of residual cryogenic ablation medium that is delivered into the body lumen 270. The valve 278 can be positioned at or near the nozzle 274 such that the valve 278, upon closing, prevents any residual or excess ablation medium within the lumen 272 and/or other passageways leading to the nozzle 274 from being delivered into the body lumen BL.

The valve 278 can include any range of suitable mechanisms. In some embodiments, the valve can be closed in its resting state but can open to allow ablation medium to be delivered into the body lumen BL. Alternatively, the valve 278 can be open in its resting state and can be closed to prevent additional ablation medium from being delivered into the body lumen BL. In some embodiments, the valve 278 can be biased closed and/or open using a spring mechanism. The valve 278 can have any suitable geometry including, for example, a cube, cone, cylinder, triangular prism, torus, helix, ovoid, or other three-dimensional body with sufficient structure to impede ablation medium flow. In some embodiments, the valve 278 can be seated against a valve seat defined within the inner shaft 270 (e.g., within lumen 272). In some embodiments, the valve 278 can be actuated, either manually or via a control device (e.g., control device 110), with a drive wire or rod, pneumatic or hydraulic pressure, electromagnetic force, and/or motor to open and/or close. Examples of suitable valves are described in International Patent Application No. PCT/US2020/045436, incorporated herein by reference.

In some embodiments, the inner shaft 270 optionally includes a sensor 273. In some embodiments, the sensor 273 can be located in a distal portion of the inner shaft 270 that is configured to be disposed within the body lumen BL. Alternatively, the sensor 273 can be disposed at a different location along the inner shaft 270, including, for example, within a lumen (e.g., lumen 272), at a proximal end at the inner shaft 270, etc. The sensor 273 can be configured to capture information about an environment within the body lumen BL. For example, the sensor 273 can be configured to measure a property (e.g., pressure, temperature) of an ablation medium being delivered to the body lumen BL, a property (e.g., pressure, temperature) of the body lumen BL or fluid within the body lumen BL, etc. The sensor 273 can include, for example, a pressure sensor (e.g., pressure transducer, strain gauge transducer, diaphragm displacement sensor, optical fiber pressure sensor, solid state sensor), temperature sensor, light sensors, gas sensors, etc. Sensor 273 can be capable of communicating data (e.g., sensor measurements) to a control unit (e.g., control unit 110) and/or other compute device (e.g., compute device 190) via a wired or wireless connection.

In some embodiments, the inner shaft 270 can optionally include one or more additional lumens. In some embodiments, a lumen can configured as a passageway for relaying pressure information or other conditions (e.g., temperature) from the body lumen BL and/or other portions of the catheter system 250. In some embodiments, the catheter system 250 can optionally include an occluder, as further described with reference to FIG. 22. While a single lumen (e.g., lumen 272) is depicted in FIG. 3, it can be appreciated that the inner shaft 270 can include any number of lumens, including a single lumen and/or more than two lumens. The inner shaft 270 can also include additional sensors, valves, nozzles, etc. according to embodiments described herein.

FIG. 4 provides a detailed view of the inner shaft 270 and the outer shaft 260 positioned within the body lumen BL. The inner shaft 270 can be disposed within the lumen 262 of the outer shaft 260. The spacing between an outer surface of the inner shaft 270 and an inner surface of the lumen 262 can define an evacuation lumen or passageway for removing gas and/or other fluids from the body lumen BL (e.g., ablation medium from the body lumen BL).

The outer shaft 260 and/or the inner shaft 270 can be formed of flexible and/or semi-flexible material that enables each to be navigated to the body lumen BL, e.g., along a guidewire. The material can be a medical grade, biocompatible material. The inner shaft 270 can be deployed into the body lumen BL in an axial direction depicted by arrow 294. The expandable structure 266 of the outer shaft 260 and the expandable structure 276 of the inner shaft 270 can be deployed radially, as depicted by arrows 292.

Figure 5:
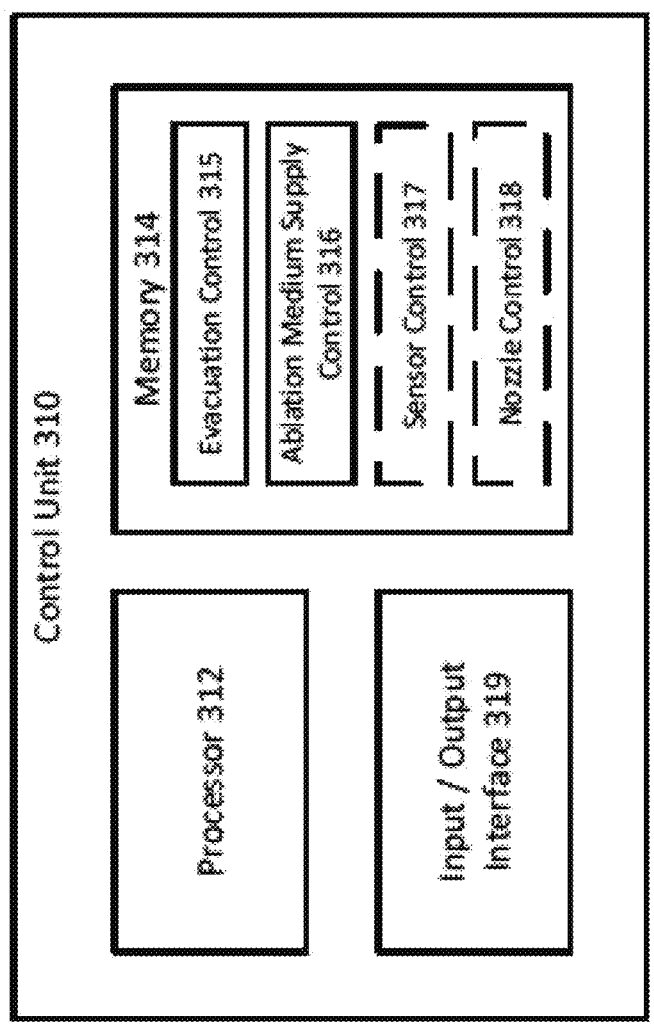
FIG. 5 is a schematic illustration of a control unit of an ablation system, according to an embodiment.

FIG. 5 is a schematic illustration of an example control unit 310, according to some embodiments. Control unit 310 can be structurally and/or functionally similar to control unit 110, as described with reference to FIG. 1. For example, control unit 310 can be configured to control one or more components of an ablation system and/or catheter system (e.g., ablation system 100, catheter system 250). Control unit 310 can include a processor 312, a memory 314, and an input/output interface 319. In some embodiments, the control unit 310 can be coupled to the catheter system, e.g., by being contained in a handheld device that is coupled to a proximal end of the catheter system. In some embodiments, the control unit 310 can be remotely situated, e.g., on a remote compute device or system, and can be used to remotely control the operation of the catheter system.

Processor 312 of control unit 310 can be any suitable processing device configured to run and/or execute functions associated with deploying one or more components of a catheter system (e.g., advancing or retracting a shaft, deploying an expandable structure, opening and/or closing a valve), delivering ablation medium into a body lumen, analyzing sensor data associated with an ablation procedure involving the catheter system, controlling temperature and/or pressure within the body lumen, etc. Processor 312 can be configured to execute modules, functions, and/or processes. Processor 312 can be a general purpose processor, a Field Programmable Gate Array (FPGA), an Application Specific Integrated Circuit (ASIC), a Digital Signal Processor (DSP), and/or the like. In some embodiments, processor 312 is part of a circuit, e.g., such as an integrated circuit. In some embodiments, one or more other components of the ablation system can be integrated into the circuit, including, for example, one or more sensors.

Input/output interface 319 can include a user interface and/or communication interfaces for connecting the control unit 310 to one or more external compute devices. The user interface(s) can include one or more components that are configured to receive inputs and send outputs to other devices and/or a user operating a device, e.g., a user operating a catheter system. For example, the user interface can include a display device (e.g., a display, a touch screen, etc.), an audio device (e.g., a speaker or alarm), and one or more additional input/output device(s) configured for receiving an input and/or generating an output to a user. The communication interface(s) can include one or more wireless and/or wired interfaces, e.g., for communicating with other compute device (e.g., compute device(s) 190) via one or more networks (e.g., a local area network (LAN), a wide area network (WAN), a virtual network, a telecommunications network).

Memory 314 can be, for example, a random access memory (RAM), a memory buffer, a hard drive, a database, an erasable programmable read-only memory (EPROM), an electrically erasable read-only memory (EEPROM), a read-only memory (ROM), and/or so forth. In some embodiments, memory 314 stores instructions that cause processor 312 to execute modules, processes, and/or functions associated with deploying one or more components of a catheter system (e.g., advancing or retracting a shaft, deploying an expandable structure, opening and/or closing a valve), delivering ablation medium into a body lumen, analyzing sensor data associated with an ablation procedure involving the catheter system, controlling temperature and/or pressure within the body lumen, etc. Methods as described herein can be implemented by way of machine (e.g., computer processor) executable code stored on an electronic storage location of the control unit 310, such as, for example, on the memory 314, or a memory operatively coupled to the control unit 310. In some embodiments, the machine executable or machine-readable code is provided in the form of software. In operation, the code can be executed by the processor 312. In some cases, the code is retrieved from the memory 314 to be accessed and/or executed by the processor 312.

As depicted in FIG. 5, memory 314 stores instructions that can cause processor 312 to execute modules, processes, and/or functions, illustrated as evacuation control 315, ablation medium supply control 316, optionally sensor control 317, and/or optionally nozzle control 318. Evacuation control 315, ablation medium supply control 316, sensor control 317, and/or nozzle control 318 can be implemented as one or more programs and/or applications that are tied to hardware components. For example, evacuation control 315, ablation medium supply control 316, sensor control 317, and/or nozzle control 318 can be implemented by one or more components of an ablation system and/or catheter system (e.g., ablation system 100, catheter system 250). In some embodiments, the processor 312 executing evacuation control 315 can control the opening of a valve and/or activation of a vacuum source to evacuate gas or other fluid (e.g., ablation medium) from a body lumen. In some embodiments, the processor 312 executing ablation medium supply control 316 can control the opening of a valve and/or operation of an ablation supply source to deliver an ablation medium into a body lumen via a catheter system. In some embodiments, the processor 312 executing sensor control 317 can receive, process, and/or analyze data from one or more sensors and/or use such data to control the operation of one or more other components of the ablation system or catheter system.

In some embodiments, the nozzle control 318 can be implemented to control positioning or movement of one or more nozzles (e.g., nozzle 274) within a body lumen (e.g., body lumen BL). In some embodiments, the nozzle control 318 can be implemented to rotate an ablation catheter (e.g., inner shaft 270) along its central axis to increase uniform or more distributed delivery of a liquid cryogen medium. In some embodiments, the nozzle control 318 can actuate the ablation catheter and/or the nozzle to move axially or linearly to increase distribution of cryogen from the nozzle. In some embodiments, the nozzle control 318 can be implemented to open and close one or more nozzle openings.

Figure 6A:
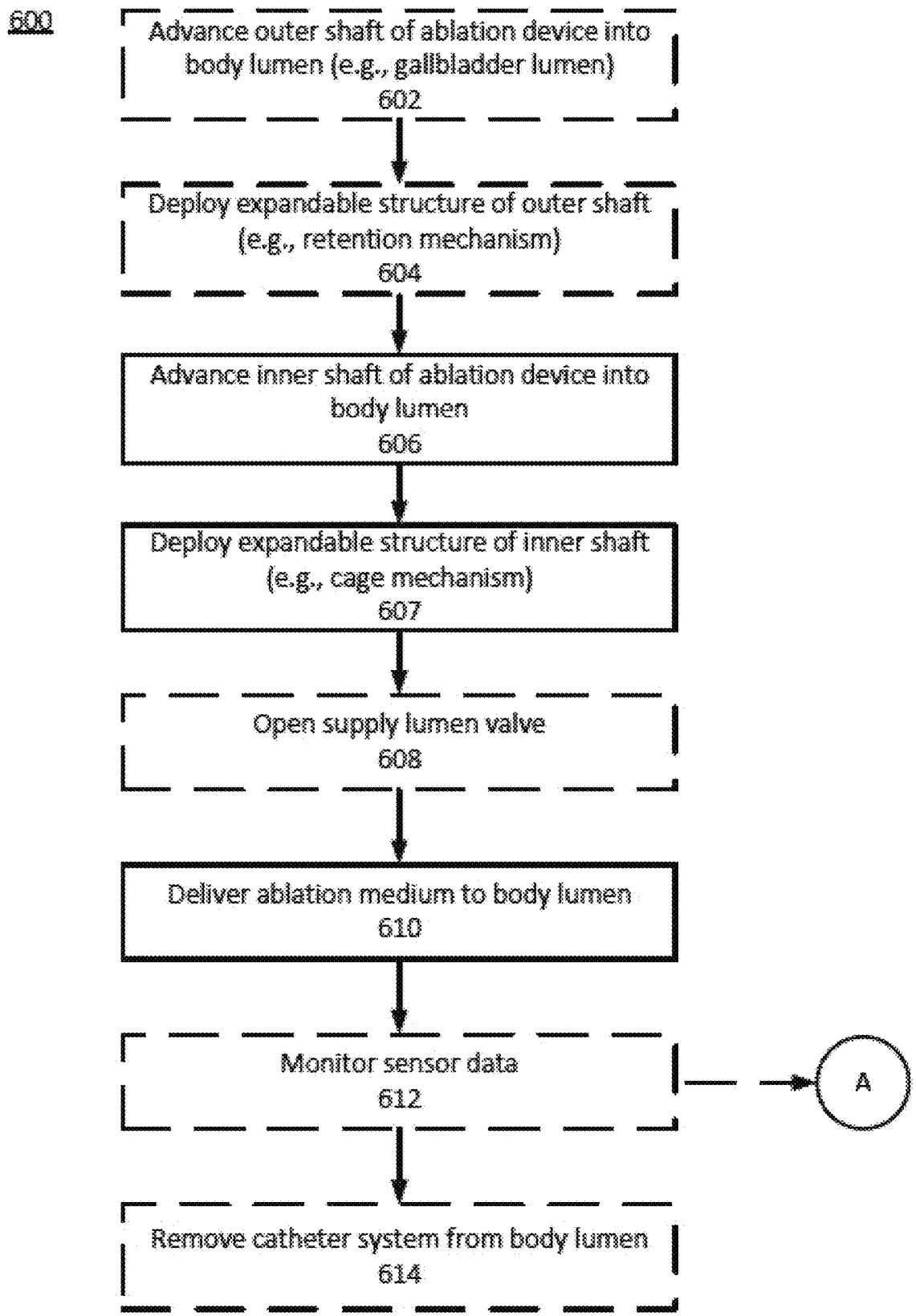
FIGS. 6A-6B are flow charts of a method for ablation and monitoring thereof, according to an embodiment.
Figure 6B:
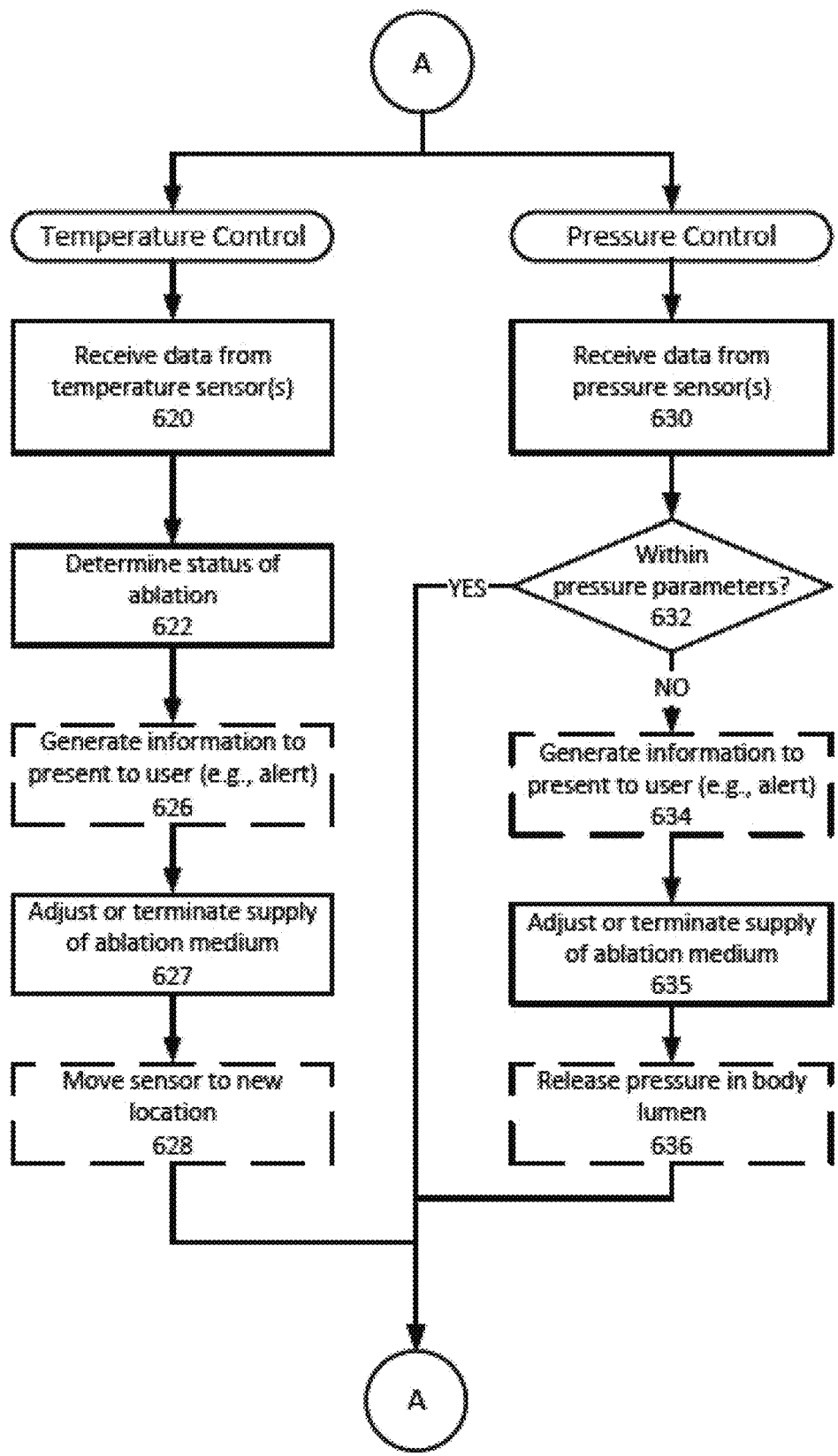

FIGS. 6A-6B depict an example method 600 for ablation and managing pressure and/or temperature during an ablation procedure, according to an embodiment. In some embodiments, the ablation procedure can be a cryoablation procedure that is implemented using an ablation system (e.g., ablation system 100) that includes a cryoablation device. In some embodiments, the ablation procedure is performed in the gallbladder to defunctionalize the gallbladder. The method 600 optionally includes advancing an outer shaft (e.g., outer shaft 260) of a catheter system (e.g., catheter system 150, 250) of the ablation system into a body lumen (e.g., gallbladder lumen), at 602. In some embodiments, ultrasonic imaging can be used to visualize the body lumen. In some embodiments, a standard needle and guidewire can be used to access the body lumen via a trans-hepatic approach, e.g., using the Seldinger technique. When the target body lumen is the gallbladder, visual return of bile through the needle and fluoroscopic confirmation of the guidewire curling inside the body lumen can assist with validating proper placement of a guidewire within the body lumen. In some embodiments, the outer shaft can be advanced along the guidewire with a dilator positioned within a lumen (e.g., lumen 262) of the outer shaft. In some embodiments, a series of progressively larger dilators can be advanced along the guidewire to dilate the tract into the body lumen. After dilating the tract, the outer shaft (e.g., with a dilator inserted within) can be advanced along the guidewire into the body lumen. In some embodiments, the outer shaft of the catheter system can be a separate tubular structure, e.g., an access sheath or an introducer, that is first placed within the body lumen before placing an inner shaft within the body lumen. Alternatively, in some embodiments, the outer and inner shafts can be placed into the body lumen simultaneously. In some embodiments, placement of the outer shaft can be similar to a percutaneous drainage tube placement technique. Once the outer shaft has been positioned in the body lumen, the dilator and guidewire can be removed to enable placement of an inner shaft within the outer shaft, as further described below.

In some embodiments, the catheter system can be placed into a gallbladder lumen. Accessing the gallbladder with the catheter system can be achieved through a percutaneous approach. In some embodiments, an access sheath or outer shaft 760 of the catheter system accesses the gallbladder 2 through a transhepatic, percutaneous approach using ultrasound guidance, as seen in FIG. 7A. In some embodiments, the access sheath 760 of the catheter device accesses the gallbladder 2 through a subhepatic, percutaneous approach using ultrasound guidance, as seen in FIG. 7B. In some embodiments, the percutaneous approach is similar to the method used to place a cholecystectomy drain. In some embodiments, the access sheath 760 provided herein accesses the gallbladder 2 endoscopically, as shown in FIG. 7C. In some embodiments, the access sheath 760 accesses the gallbladder 2 utilizing native anatomy by creating a transmural stoma connecting the inner lumen of the gallbladder to the lumen of the small bowel, as shown in FIG. 7C. In some embodiments, percutaneous access is gained using a hollow bore needle, whereby a guidewire is placed through the needle to create a tract to the desired access location (e.g., a cystic duct, a gallbladder, or a combination thereof). In some embodiments, the access sheath 760 and an inner shaft or ablation catheter are configured with a concentric lumen to enable a guidewire to pass through. In some embodiments, the access sheath 760 and the ablation catheter are configured with a non-concentric lumen to enable a guidewire to pass through.

After positioning the distal end of the outer shaft of the catheter system within the body lumen, the method 600 can optionally include deploying an expandable structure (e.g., expandable structure 266) of the outer shaft, at 604. Deploying the expandable structure within the body lumen can ensure that the outer shaft (e.g., access catheter, introducer) remains or is retained within the body lumen during the ablation procedure. In some embodiments, deploying the expandable structure can involve moving a first tubular member relative to a second tubular member to bring a first end of the expandable structure toward the second end of the expandable structure, thereby causing the expandable structure to expand outwards. In some embodiments, expanding the expandable structure can involve releasing tension placed on the expandable member (e.g., by releasing a sheath or pull wire) and allowing the expandable structure to automatically expand or self-expand into a pre-formed shape.

The method 600 can include advancing an inner shaft (e.g., inner shaft 270) of the catheter system into the body lumen, at 606. In some embodiments, where a dilator was positioned in the outer shaft to advance the outer shaft into the body lumen, the inner shaft can be advanced after removal of the dilator. The inner shaft can be advanced until a nozzle (e.g., nozzle 274) of the inner shaft is disposed within the body lumen distal to a distal end of the outer shaft. The inner shaft can be advanced into the body lumen by inserting the inner shaft into a lumen defined by the outer shaft and advancing the inner shaft through that lumen until a distal portion of the inner shaft is disposed distal to the outer shaft. The distal portion of the inner shaft can include one or more openings (e.g., fenestrations) that can deliver ablation medium into the body lumen. In some embodiments, the method 600 can optionally include deployment of saline to lavage and drain any content within the body lumen, e.g., via inner and/or outer shafts. For example, fluid such as saline can be delivered into the gallbladder via a first lumen (e.g., lumen 272 defined by inner shaft 270) and/or content within the body lumen (e.g., gallbladder content) can be evacuated from the body lumen via a second lumen (e.g., lumen 262 defined by outer shaft 260).

The method 600 includes deployment of an expandable structure (e.g., expandable structure 276) of the inner shaft, at 607. In some embodiments, the expandable structure can include a plurality of wires or bands that extend along a length of the inner shaft. Such wires can be deployed by advancing the wires distally out of a sheath. In some embodiments, the expandable structure can be deployed by moving inner and outer tubular members relative to one another. Once the expandable structure is deployed, the expandable structure can center the nozzle within the body lumen or ensure that the nozzle is at least a predetermined distance away from a tissue surface. The method 600 can optionally include opening a supply lumen valve (e.g., valve 278), at 608. For example, as discussed above with reference to FIG. 3, a valve can be positioned along an ablation medium delivery passageway (e.g., along lumen 272 defined by inner shaft) to control delivery of the ablation medium. The valve in its open state can allow ablation medium to flow past the valve and into the body lumen, while the valve in its closed state can block the flow of ablation medium into the body lumen. In some embodiments, the valve can naturally be in a closed state, and therefore method 600 can include opening the valve such that ablation medium can be delivered into the body lumen. In some embodiments, the valve can naturally be in an open state, and therefore 608 can be omitted.

The method 600 can include delivering the ablation medium to the body lumen, at 610. In some embodiments, a cartridge (e.g., ablation medium supply source 120, 220) of a cryogenic ablation medium (e.g., nitrous oxide) or any other suitable ablation medium can be loaded into a handle (e.g., handheld device) of the ablation device. In the case of using a cryogenic ablation medium, 1, 2, 3, 4, 5, 6, 7, 8, 9, 10 or more than 10 freeze-thaw cycles can be delivered to the gallbladder, at 610, to ensure complete hypothermic death of the gallbladder mucosa. While delivering the ablation medium, method 600 can include events and/or steps associated with pressure and/or temperature monitoring at 612, as further described below with reference to FIG. 6B. For example, a control unit (e.g., control unit 110, 310) can monitor pressure, temperature, and/or other conditions to ensure safe delivery of the ablation medium. After delivering the ablation medium, the method 600 can optionally include removing the catheter system (e.g., inner and outer shafts) from the body lumen, at 614.

FIG. 6B illustrates events and steps associated with a temperature and pressure monitoring protocol performed during an ablation procedure, such as the ablation procedure described with reference to FIG. 6A. The control unit (e.g., control unit 110, 310) of the ablation system or another compute device can be configured to receive data from a temperature sensor, at 620, and determine a status of ablation, at 622. In some embodiments, the status of the ablation can be determined by data received from the temperature sensor. In some embodiments, the temperature sensor can be integrated into one of the inner or outer shafts (e.g., as sensor 263, 273). In other embodiments, the temperature sensor can be operatively coupled to a lumen that extends into the body lumen, which the sensor can use to measure a temperature associated with the body lumen. In still other embodiments, the temperature sensor can be mounted to a probe that is separately insertable into the body lumen, e.g., via a separate lumen (e.g., lumen 264) and/or the same lumen that houses the inner shaft (e.g., lumen 262). In some embodiments, the temperature sensor can be implanted or inserted into tissue within the body lumen such that a temperature of the tissue can be measured.

The method 600 can optionally include generating information to present to a user, at 626. In some embodiments, the information presented to the user can be presented via a compute device, such as control unit 110 and/or 310, or other compute device in network communication with the ablation system (e.g., a tablet, smartphone, or any other suitable communication device). Based on the status of the ablation determined at 622, the supply of ablation medium can be adjusted or terminated at 627. In some embodiments, the supply of ablation medium can be reduced or terminated. In some embodiments, the supply of ablation medium can be increased. In some embodiments, to evaluate the temperature of tissue at a different location, the temperature sensor can optionally be moved to a new location, at 628. For example, the temperature sensor can be retracted from tissue a first location, moved to a second location, and inserted into tissue at a second location. In some embodiments, the method 600 can include determining whether the ablation is completed, e.g., based on sensor data, and in response to determining that the ablation has completed, the supply of ablation medium can be terminated (e.g., by closing valve 278), and the method 600 can continue to 612, where the catheter system is removed from the body lumen.

The control unit (e.g., control unit 110, 310) or another compute device can also receive pressure data from one or more pressure sensors, at 630. In some embodiments, a first pressure reading can be from inside the body lumen (e.g., measuring intraluminal pressure), while second pressure reading can be from inside the outer shaft (e.g., measuring pressure within the evacuation lumen (e.g., lumen 262)). In other embodiments, more or less pressure readings can be received at 630. At 632, at least one of the pressure measurements (e.g., intraluminal pressure within body lumen) is evaluated to determine if the pressure reading is within desired pressure parameters (e.g., within a desirable pressure range). If the pressure readings are substantially different from one another (e.g., the different pressure readings differ more than a predetermined amount or percentage from one another, or have a percentage (e.g., 30%) increase or decrease from a nominal operating pressure), or if one or more pressure readings are not within one or more desired pressure parameters (632: NO), information (e.g., an alert) can optionally be presented to the user, at 634, and the supply of ablation medium can be adjusted or terminated, at 635. The information presented to the user can indicate to the user that an error has occurred with the ablation delivery and/or operation of the device. For example, a substantial difference (e.g., difference above a predetermined amount or percentage) between an intraluminal pressure within the body lumen and a pressure within the evacuation lumen (such as the intraluminal pressure being greater than the evacuation lumen pressure) can indicate that a blockage has occurred at some point between the body lumen and the evacuation lumen. With cryogenic delivery systems, such can occur when ice or other solid content blocks a portion of an evacuation lumen. Such blockage can cause a pressure buildup in the body lumen and can result in injury to a patient. Therefore, in such cases, the control unit or other compute device can terminate supply of an ablation medium into the body lumen until the blockage is removed (e.g., via heating coils). In some embodiments, when a pressure measurement is outside of certain pressure parameters (e.g., a predetermined threshold value or range), the control unit can control one or more valves and/or a vacuum source (e.g., vacuum source 130) to evacuate ablation medium from the body lumen so as to reduce pressure buildup within the body lumen, at 636.

At 614, the catheter system (e.g., introducer and ablation catheter) can be removed from the body lumen. For a time period (e.g., a few weeks) after the removal of the ablation system, the body's chronic inflammatory response can scar the ablated gallbladder tissue, leading to involution of the lumen and occlusion of the cystic duct. Bile flow can be shut off to the gallbladder, while its blood supply remains uncompromised, resulting in an inert organ.

In some embodiments, as described above, the ablation procedures described herein use a cryogenic ablation medium. In some embodiments, the cryogenic ablation medium is a liquid. In some embodiments, the cryogenic ablation medium is a gas. In some embodiments, the cryogenic ablation medium undergoes a liquid-to-gas phase transition when being delivered using the catheter devices and nozzles disclosed herein. In some embodiments, cryoablation is achieved via the refrigerant property due to the liquid to gas phase change from an ablation medium, such as liquid nitrous oxide, carbon dioxide, and argon. In some embodiments, the phase change of the cryogenic ablation medium is triggered by a sudden reduction in pressure. In some embodiments, the phase change of the cryogenic ablation medium occurs when the liquid ablation medium contacts a wall of the body lumen (e.g., wall of the gallbladder). As such, the liquid ablation medium can be delivered into the body lumen and contact the wall of the body lumen and phase change into a liquid ablation medium. Ablation can happen at the phase change interface.

Figure 8:
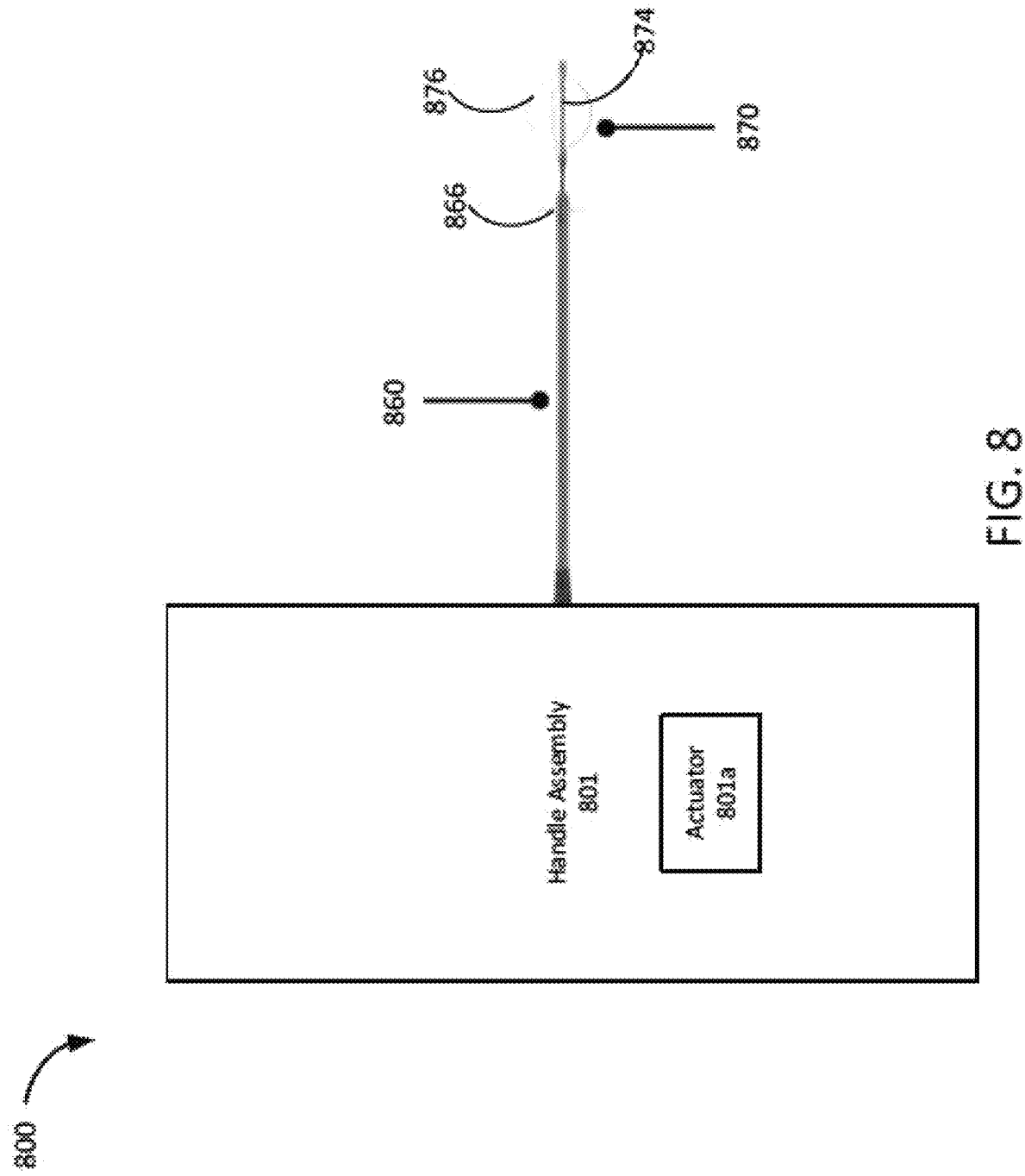
FIG. 8 is an illustration of an ablation system, according to an embodiment.
Figure 9:
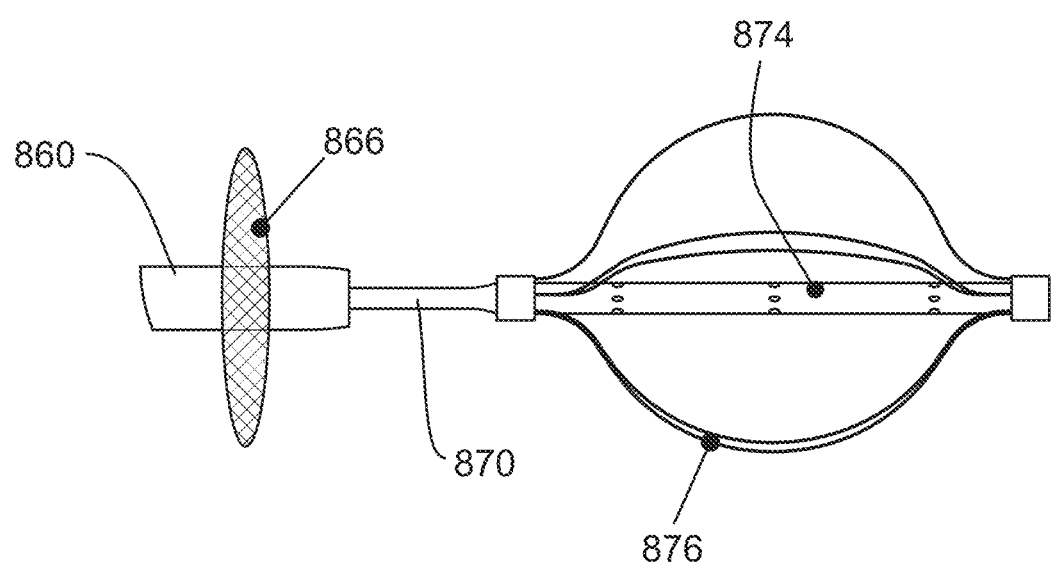
FIG. 9 is a detailed view of an outer shaft and an inner shaft of an ablation catheter, according to an embodiment.

FIGS. 8-9 illustrate an ablation system implemented as a cryoablation device 800, according to an embodiment. The cryoablation device 800 can be configured to ablate or defunctionalize a gallbladder cavity. The cryoablation device 800 can include components that are structurally and/or functionally similar to other ablation systems and components thereof described herein (e.g., ablation system 100, catheter system 250, control unit 310, etc.) As shown the cryoablation device 800 includes a handle assembly 801, an outer shaft 860, and an inner shaft 870. The outer shaft 860 includes an expandable structure 866. The inner shaft 870 includes a nozzle 874 and an expandable structure 876. In some embodiments, the handle assembly 801 can include or house a control unit (e.g., control unit 110). In some embodiments, the handle assembly 801 can include an actuator 801a (e.g., a button) or multiple actuators 801a. In some embodiments, actuators can be used to control deployment of the expandable structure 866 on the outer shaft 860, the expandable structure 876 on the inner shaft 870, deployment of ablation medium through the nozzle 874, actuation of nozzle 874 (e.g., translation of rotation of nozzle 874), etc. In some embodiments, the handle assembly 801 can be fluidically coupled to an ablation medium supply (e.g., ablation medium supply 120). In some embodiments, the handle assembly 801 can include a user interface (e.g., input/output interface 319) to communicate information to the user and/or receive inputs from the user.

FIG. 9 is a detailed view of the outer shaft 860 and the inner shaft 870 of the cryoablation device 800, according to an embodiment. The outer shaft 860 and the inner shaft 870 can include components that are structurally and/or functionally similar to other ablation systems and components thereof described herein (e.g., outer shaft 260 and the inner shaft 270, etc.). As shown, the expandable structure 876 can be implemented as an expandable cage mechanism. As shown, the expandable structure 876 has a "closed" design, e.g., the bands or wires that form the expandable structure 876 come together and are closed on both the proximal end and the distal end of the expandable structure 876 such that the expandable structure 876 forms an enclosed basket or cage.

Figure 10:
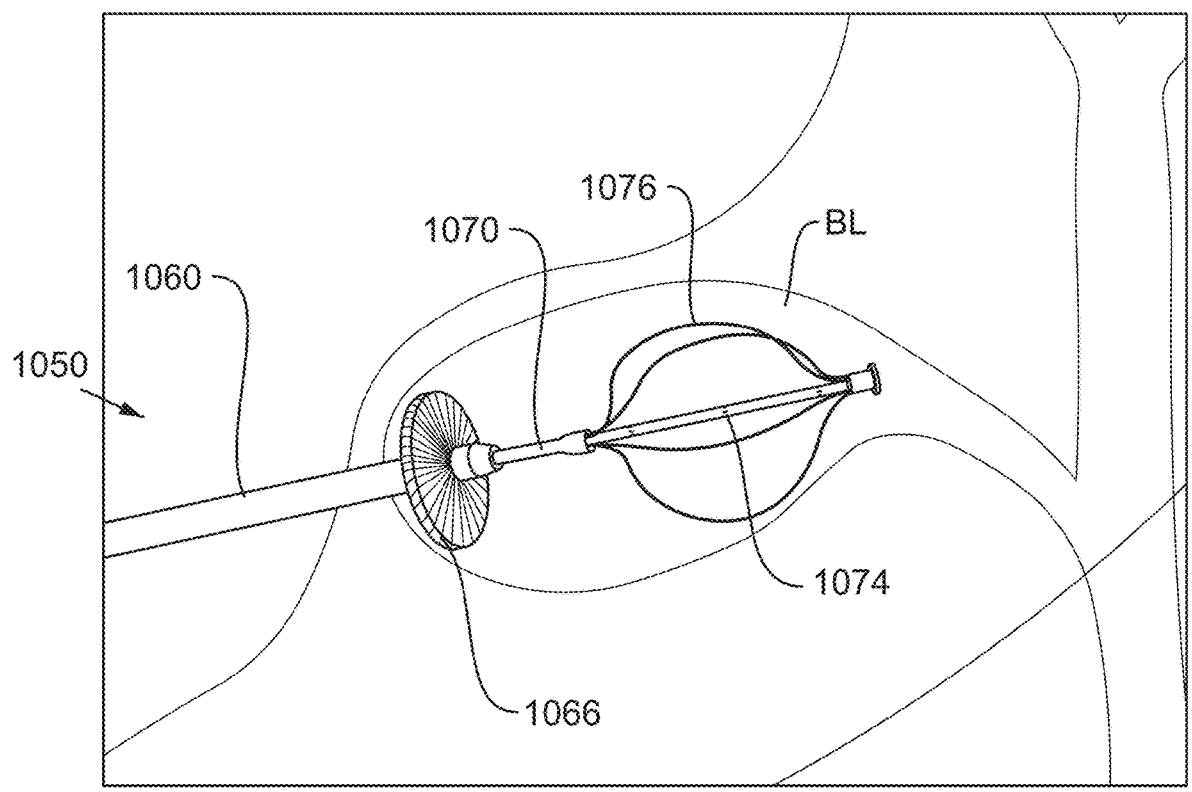
FIG. 10 is an illustration of an ablation catheter deployed into a body lumen, according to an embodiment.

FIG. 10 shows an ablation catheter 1050 deployed in a body lumen BL, according to an embodiment. The ablation catheter 1050 can include components that are structurally and/or functionally similar to other ablation systems and components thereof described herein (e.g., ablation system 100, catheter system 250, control unit 310, cryoablation device 800, etc.). As shown, the ablation catheter 1050 includes an outer shaft 1060 with an expandable structure 1066 and an inner shaft 1070 with a nozzle 1074 and an expandable structure 1076. As shown, the expandable structure 1066 on the outer shaft 1060 is in the deployed state, such that the ablation catheter 1050 is inhibited from unintentionally exiting the body lumen BL (e.g., is maintained in position within the body lumen BL). The expandable structure 1076 on the inner shaft 1070 is in the deployed state to approximately center the nozzle 1074 within the body lumen BL, e.g., to ensure uniform and/or minimum spacing (e.g., a predetermined amount of spacing) between the nozzle 1074 and a tissue wall of the body lumen BL. As described above, such placement of the nozzle 1074 increases effectiveness of the ablation delivery and reduces potential undesirable effects (e.g., injury, attachment between nozzle and tissue, etc.). The expandable structure 1066 and the expandable structure 1076 are both collapsible (e.g., transitionable back into an undeployed state), such that the ablation catheter 1050 can be retracted from the body lumen BL.

Figure 11:
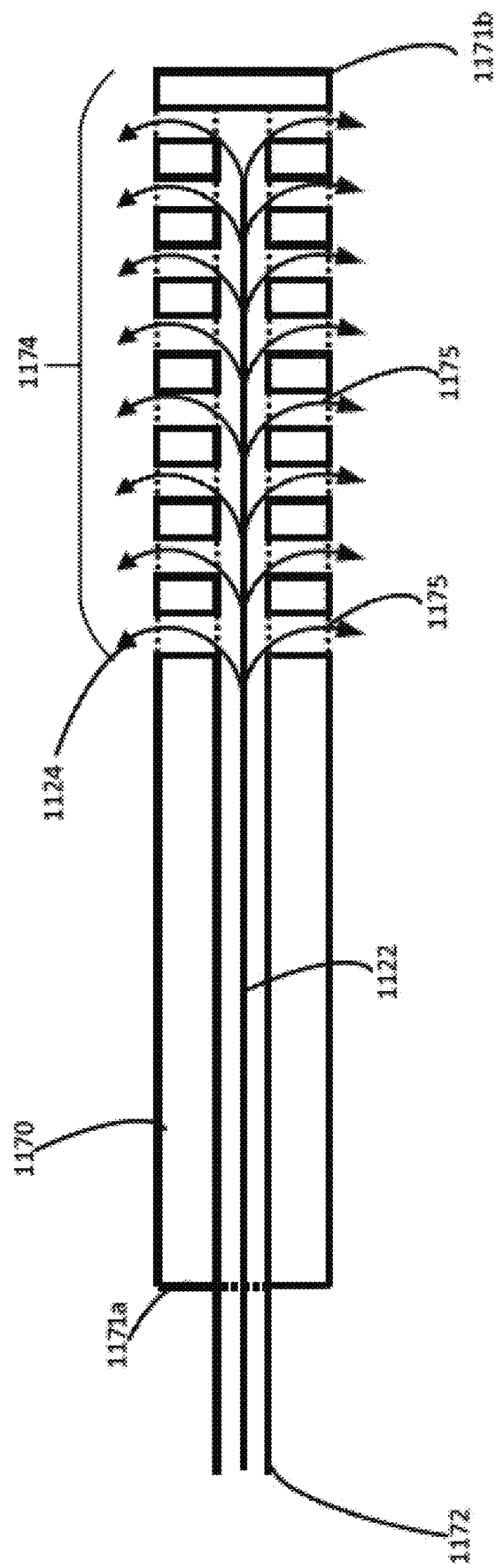
FIG. 11 is an illustration of an inner shaft of an ablation catheter with a fenestrated nozzle, according to an embodiment.

FIG. 11 illustrates an example of an inner shaft 1170 comprising a lumen 1172 and a fenestrated nozzle 1174. The inner shaft 1170 can include components that are structurally and/or functionally similar to other ablation systems and components thereof described herein (e.g., the inner shaft 270, inner shaft 870, etc.). In some embodiments, the inner shaft 1170 can include a proximal end 1171*a* and a distal end 1171*b*. In some embodiments, the lumen 1172 is sufficiently small to keep the cryogenic liquid ablation medium 1122 in a liquid state, with the cryogenic liquid ablation medium 1122 transitioning into a cryogenic gas ablation medium 1124 (i.e., a liquid-to-gas phase transition) as it exits the inner shaft 1170 via a plurality of fenestrations 1175, as shown in FIG. 11 (e.g., due to a pressure drop between inside of lumen 1172 and an inside of the gallbladder). In some embodiments, the cryogenic gas ablation medium 1124 exits the fenestrated nozzle 1174 via the plurality of fenestrations 1175 and ablates the outer surface of the gallbladder lumen once the cryogenic gas ablation medium 1124 upon contact with the tissue.

Figure 12A:
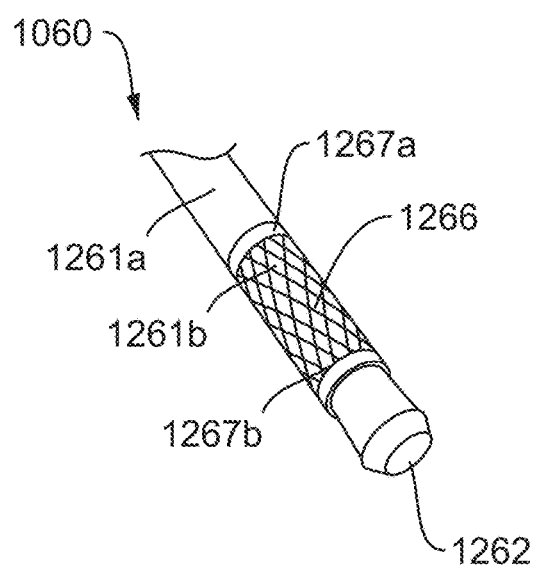
FIGS. 12A-12B are illustrations of an outer shaft of an ablation catheter, according to an embodiment.
Figure 12B:
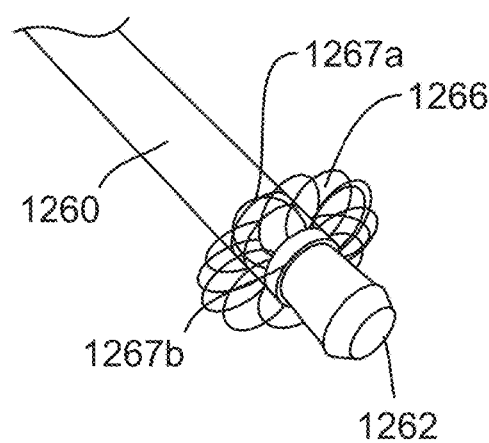

FIGS. 12A-12B are illustrations of an outer shaft 1260 of an ablation system (e.g., a cryoablation device), according to an embodiment. The outer shaft 1260 can include components that are structurally and/or functionally similar to other outer shafts of ablation systems described herein (e.g., outer shaft 260, outer shaft 860, outer shaft 1060, etc.). As shown, the outer shaft 1260 can include an outer tubular member 1261*a* and an inner tubular member 1261*b* that are arranged concentrically. Also shown are a lumen 1262 and an expandable structure 1266. FIG. 12A shows the expandable structure 1266 in an undeployed state, while FIG. 12B shows the expandable structure 1266 in a deployed state. As shown, the expandable structure 1266 includes wires arranged in a braided configuration with a proximal ring 1267*a* and a distal ring 1267*b*. In some embodiments, at least one of the proximal ring 1267*a* and the distal ring 1267*b* can be moved toward the other to induce outward expansion (e.g., deployment) of the expandable structure 1266. In some embodiments, the proximal ring 1267*a* and the distal ring 1267*b* can be moved by sliding the tubular members 1261*a*, 1261*b*.

In some embodiments, the rings 1267*a*, 1267*b* and/or wires of the expandable structure 1266 can be radiopaque to aid in visualizing actuation of the expandable structure 1266 under image guidance (e.g., fluoroscopic imaging, ultrasonic imaging). In some embodiments, the proximal ring 1267*a* and the distal ring 1267*b* can be moved via a pull wire, a spring, a sheath, and/or any other suitable mechanism. For example, one or more pull wires can be actuated to move at least one of the proximal ring 1267*a* and the distal ring 1267*b* toward the other. In some embodiments, the expandable structure 1266 can be under tension when in the undeployed state (FIG. 12A) and in a relaxed state when in the deployed state (FIG. 12B). In particular, the expandable structure 1266 can be held in tension along an outer surface of the outer shaft 1260, and can be released (e.g., by releasing the hold on one or both ends of the expandable structure 1266, such as by releasing a pull wire, a sheath, etc.) to allow the expandable structure 1266 to self-expand into a deployed state. In some embodiments, the expandable structure 1266 can be composed of a shape memory material, such that they maintain their shape in the deployed state, unless subject to outside force. In some embodiments, the bands can be under tension when in the deployed state and in a relaxed state when in the undeployed state. For example, pushing or moving the outer tubular member 1261*a* in a distal direction relative to the inner tubular member 1261*b* can cause the expandable structure 1266 to transition from an undeployed state to a deployed state. As another example, pulling or moving the inner tubular member 1261*b* in a proximal direction relative to the outer tubular member 1261*a* can cause the expandable structure 1266 to transition from an undeployed state to a deployed state.

Figure 13A:
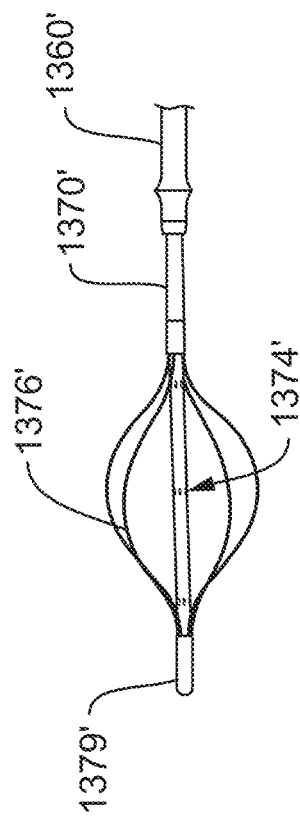
FIGS. 13A-13C are illustrations of portions of ablation catheters with expandable structures, according to various embodiments.
Figure 13B:
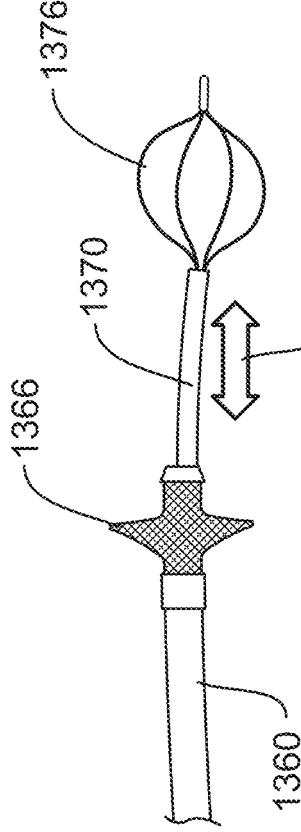
Figure 13C:
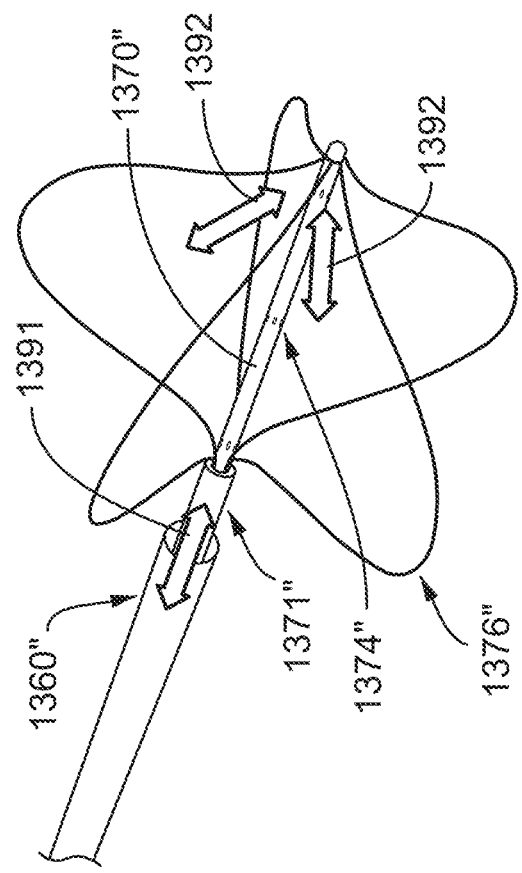

FIGS. 13A-13C show portions of ablation devices with different arrangements of expandable structures and nozzles. The ablation devices described in FIGS. 13A-13C can include components that are structurally and/or functionally similar to other ablation systems and components thereof described herein (e.g., ablation system 100, catheter system 250, control unit 310, cryoablation device 800, cryoablation catheter 1050, etc.). FIG. 13A shows an outer shaft 1360 with an expandable structure 1366 and an inner shaft 1370 with an expandable structure 1376. The inner shaft 1370 is slidable within the outer shaft 1360, such that the inner shaft 1370 can move axially in a direction along arrow 1391 (e.g., in a direction along a longitudinal axis of the outer shaft 1360). The expandable structure 1376 can be coupled to distal portion of the inner shaft 1370. The inner shaft 1370 can be advanced through the outer shaft 1360 until the distal portion of the inner shaft 1370 (e.g., including the expandable structure 1376) is disposed distal to a distal end of the outer shaft 1360. When so positioned, the expandable structure 1376 can be configured to expand into its expanded state, as depicted in FIG. 13A. While not depicted in FIG. 13A, a nozzle can be separately advanced distally from the outer shaft 1360. For example, a separate shaft supporting a nozzle can be advanced through the lumen of the outer shaft 1360 and into a space proximate to the expandable structure 1376. The nozzle can be advanced separately from the expandable structure 1376 such that a user can manipulate a position of the nozzle relative to the expandable structure 1376. Alternatively, in some embodiments, the inner shaft 1370 can include a nozzle. The expandable structure 1376 can include a plurality of bands or wires. In some embodiments, the bands can be composed of a shape memory material, such that they maintain their shape in the deployed state, unless subject to outside force. As described above, in some embodiments, the bands can be under tension when in the undeployed state and in a relaxed state when in the deployed state. Alternatively, the bands can be in a relaxed state when in the undeployed state and under tension when in the deployed state.

FIG. 13B shows an ablation device with an outer shaft 1360', an inner shaft 1370', a nozzle 1374', an expandable structure 1376', and a hub 1379'. As shown, the expandable structure 1376' includes a plurality of wires or bands that extends outward and distally from the inner shaft 1370' and couples to a distal hub 1379'. In some embodiments, the bands extend through the length of the inner shaft 1370', such that the bands can be advanced and retracted from the proximal end of the inner shaft 1370'. Advancement of the bands can cause expansion of the expandable structure 1376' to deploy the expandable structure 1376', and retraction of the bands can pull the expandable structure 1376' back toward the inner shaft 1370 to return the expandable structure 1376' to its undeployed state. In some embodiments, the bands of the expandable structure 1376' can be under tension when in an undeployed state and in a relaxed state when in the deployed state. In other words, the bands can be held in tension such that the expandable structure 1376' is held in a undeployed or unexpanded state, and releasing the bands can allow the bands to self-expand into the deployed state. In some embodiments, the bands can be moved via an actuator located at a proximal end of the inner shaft 1370'. In some embodiments, the actuator can be activated by pushing a button, moving a slider, releasing a spring, or actuating any other suitable mechanism. In some embodiments, the bands of the expandable structure 1376' can be under tension when in the deployed state and in a relaxed state when in the undeployed state. In other words, the bands can be advanced or pushed from the proximal end of the inner shaft 1370' to expand the expandable structure 1376' into its expanded or deployed state. As shown, the nozzle 1374' can be located within the expandable structure 1376'. The nozzle 1374' can be coupled to a lumen that extends through the inner shaft 1370', such that the nozzle 1374' can receive and delivery an ablation medium into the body lumen. The nozzle 1374' can terminate proximal of the hub 1379'. In some embodiments, the nozzle 1374' can be advanced independently of the expandable structure 1376' such that its position within the expandable structure 1376' can be adjusted.

In some embodiments, a sensor can be disposed in the hub 1379'. In some embodiments, the sensor can be a temperature sensor. In some embodiments, the sensor can be a pressure sensor. In some embodiments, when the inner shaft 1370' is positioned within a gallbladder lumen to deliver the ablation medium (e.g., cryogenic ablation medium), the hub 1379' can be positioned at or proximate to a cystic duct and can measure a temperature and/or a pressure within the cystic duct. Such measurements can be used to monitor a progress of the ablation procedure and/or operational conditions during the ablation procedure (e.g., for safety).

FIG. 13C shows an ablation device (e.g., cryogenic catheter) with an outer shaft 1360", an inner shaft 1370", a nozzle 1374", an expandable structure 1376". The ablation device can include a sleeve 1371" that defines a set of one or more lumens for receiving one or more bands or wires that form the expandable structure 1376". The bands that form the expandable structure 1376" can extend from a proximal end beyond a distal end of the sleeve 1371", such that the bands can be advanced and/or retracted from the proximal end of the sleeve 1371". In some embodiments, the bands of the expandable structure 1376" can be under tension when in an undeployed state and in a relaxed state when in the deployed state. In other words, pulling the bands from the proximal end of the sleeve 1371" can flatten the expandable structure 1376" and releasing the bands can allow the bands to self-expand into the deployed state. In some embodiments, the bands can be pulled or released from the proximal end of the secondary inner shaft 1371" via an actuator. In some embodiments, the bands of the expandable structure 1376" can be under tension when in the deployed state and in a relaxed state when in the undeployed state. In other words, the bands can be advanced or pushed from the proximal end of the secondary inner shaft 1371" to expand. In some embodiments, the movement of the bands of the expandable structure 1376" can be caused by an actuator (e.g., a button, slider, motor, spring, etc.).

In some embodiments, the sleeve 1371" can move in proximal and distal directions along line 1391. In some embodiments, the sleeve 1371" can act as a pushing mechanism, e.g., to deploy the expandable structure 1376". For example, in response to pushing the sleeve 1371" toward the distal end of the inner shaft 1370", the expandable structure 1376" can expand outward to a deployed state in a first direction along arrows 1392. In response to pulling the sleeve 1371" away from or proximally from the distal end of the inner shaft 1370", the expandable structure 1376" contracts inward to an undeployed state in the opposite direction along arrows 1392.

Figure 14:
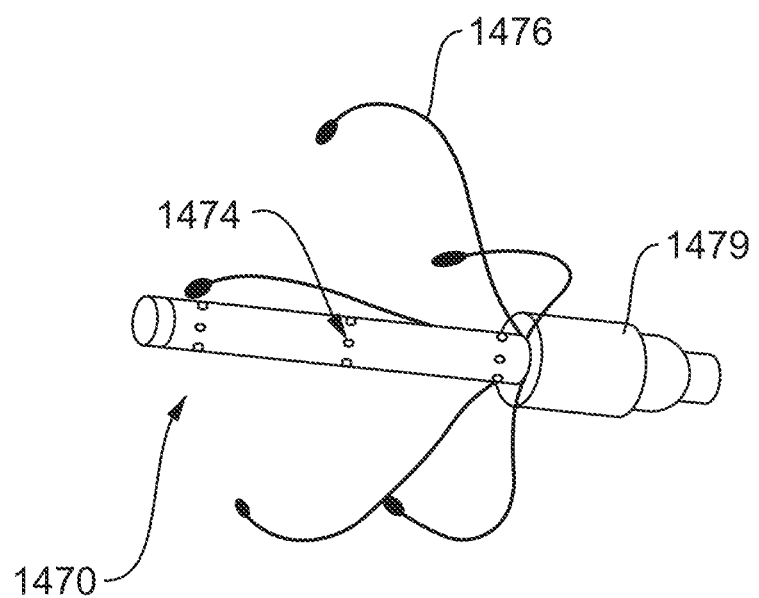
FIG. 14 is an illustration of an inner shaft of an ablation catheter with an expandable structure, according to an embodiment.

FIG. 14 shows an inner shaft 1470 of an ablation catheter or catheter system with an alternative example of an expandable structure 1476, according to an embodiment. The expandable structure 1476 can include a plurality of wires or splines that are coupled to a hub or shaft at a first end (e.g., a proximal end) and uncoupled at a second, opposite end (e.g., a distal end). In other words, the expandable structure 1476 has an "open" configuration. The inner shaft 1470 can include components that are structurally and/or functionally similar to other ablation systems and components thereof described herein (e.g., the inner shaft 270, inner shaft 870, inner shaft 1170, inner shafts 1370, 1370', 1370", etc.). The inner shaft 1470 also includes a nozzle 1474 and a hub 1479. The bands of the expandable structure 1476 can be coupled to the hub 1479 at their proximal end. As shown, the hub 1479 is located on the proximal to the nozzle 1474. While the hub 1479 is depicted being proximal to the nozzle 1474, it can be appreciated that in other embodiments, the hub 1479 can be located distal to the nozzle 1474. Similar to other expandable structures described herein, the expandable structure 1476 can be configured to self-expand (e.g., after being released from being in tension, or after the bands are advanced distal of the hub 1479). In some embodiments, the expandable structure 1476 can be composed of a shape memory material, such that the expandable structure 1476 remains in the expanded state during cryoablation.

Figure 15:
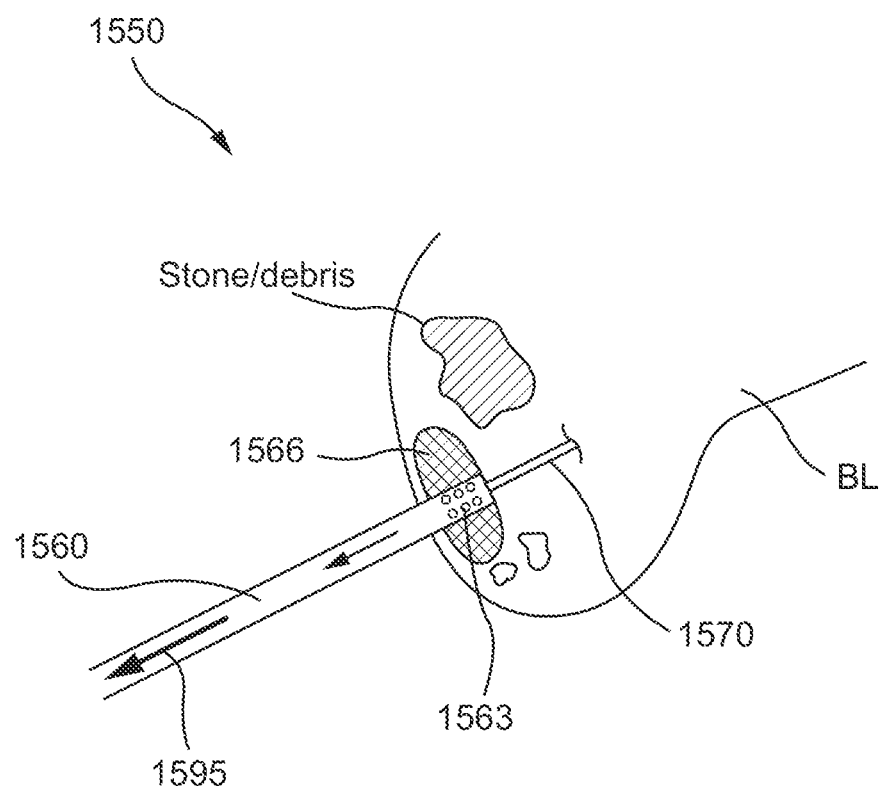
FIG. 15 is an illustration of an ablation catheter with openings for evacuation, according to an embodiment.
Figure 16A:
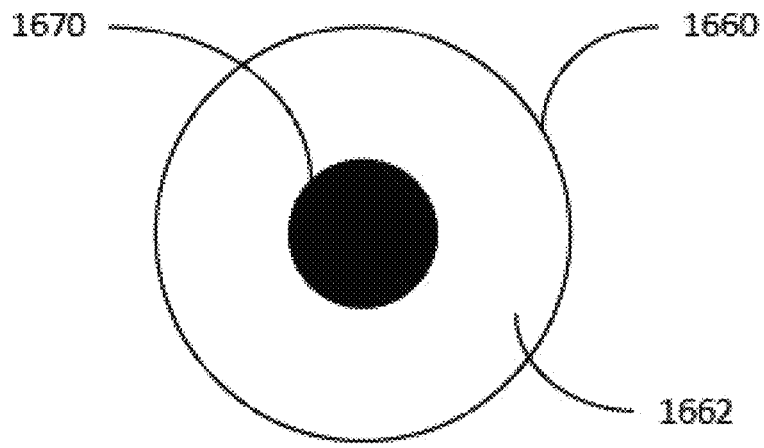
FIGS. 16A-16B are cross-sectional views of ablation catheters including evacuation lumens, according to various embodiments.
Figure 16B:
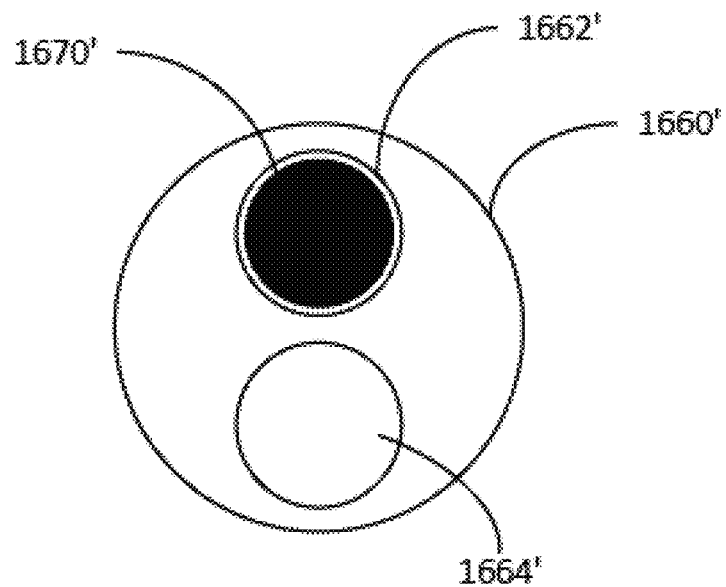

FIGS. 15-16B show catheter systems with evacuation lumens for evacuation of fluids (e.g., gas, liquid) or smaller debris from a body lumen BL, according to various embodiments. FIG. 15 shows an ablation catheter 1550 partially disposed in a body lumen BL, according to an embodiment. The ablation catheter 1550 can include components that are structurally and/or functionally similar to other ablation systems and components thereof described herein (e.g., ablation system 100, catheter system 250, control unit 310, cryoablation device 800, ablation catheter 1050, etc.). The ablation catheter 1550 includes an outer shaft 1560 and an inner shaft 1570. The outer shaft 1560 includes evacuation holes 1563 (e.g., evacuation openings) and an expandable structure 1566. In some embodiments, the evacuation holes 1563 can be inserted into the body lumen BL during ablation, such that fluids or smaller debris can exit the body lumen BL through the evacuation holes 1563 and flow out of the body lumen BL via the outer shaft 1560 along a passageway indicated by arrow 1595. In some embodiments, the expandable structure 1566 can be disposed around the outside of the evacuation holes 1563, such that the expandable structure 1566 acts as a filter to prevent larger pieces of debris from clogging the evacuation holes 1563. In some embodiments, the expandable structure 1566 can have a mesh structure that can aid in filtering debris (e.g., stones, sludge, bile) from entering an evacuation pathway in the outer shaft 1560, creating a reliable pathway to relieve ablation gas and pressure in the body lumen BL. In some embodiments, the debris that exits the body lumen via the evacuation holes 1563 can be solid, liquid, and/or gas. In some embodiments, the evacuation holes 1563 can be fluidically coupled to a lumen that runs along the arrow 1595 inside the outer lumen 1560 and outside the inner lumen 1570. In some embodiments, the expandable structure 1566 can create a reliable pocket for evacuation of ablation gas.

FIGS. 16A-16B show cross sections of outer shafts 1660, 1660' with evacuation lumens, according to various embodiments. FIG. 16A includes an outer shaft 1660 and an inner shaft 1670. The outer shaft 1660 and inner shaft 1670 can include components that are structurally and/or functionally similar to other ablation systems and components thereof described herein (e.g., outer shaft 260, inner shaft 270, outer shaft 860, inner shaft 870, outer shaft 1060, inner shaft 1070, outer shaft 1260, etc.). As shown in FIG. 16A, the outer shaft 1060 can include a lumen 1662 within which the inner shaft 1070 is disposed. During an ablation procedure, the space between an outer surface of the inner shaft 1070 and an inner surface of the outer shaft 1060 can define an evacuation channel or passageway. In some embodiments, debris can flow into evacuation holes (e.g., evacuation holes 1563) within a body lumen and flow through the evacuation channel to exit the body lumen.

FIG. 16B depicts an alternative arrangement of lumens within an outer shaft 1670' of an ablation catheter (e.g., a cryoablation device). As shown, the outer shaft 1670' can include a separate lumen 1664' that is designated for evacuation of content (e.g., solids, fluids, etc.) from within the body lumen BL. In some embodiments, the lumen 1664' can be fluidically coupled to evacuation holes (e.g., evacuation holes 1563) that can be disposed in the body lumen. In some embodiments, the lumen 1664' can provide a flow path for fluid and/or debris to exit the body lumen. Similar to other outer shafts, the outer shaft 1660' can define a lumen 1662' that can receive an inner shaft 1670' and be used to guide the inner shaft 1670' into the body lumen.

FIGS. 17A-17B show an outer shaft 1760 of an ablation catheter (e.g., a cryoablation device) with an expandable structure 1766, according to an embodiment. The outer shaft 1760 includes evacuation holes 1762a and an evacuation lumen 1762. The outer shaft 1760 can include components that are structurally and/or functionally similar to other ablation systems and components thereof described herein (e.g., outer shaft 260, outer shaft 860, outer shaft 1060, inner shaft 1070, outer shaft 1660, etc.). FIG. 17A shows the expandable structure 1766 in an undeployed (i.e., unexpanded) state, while FIG. 17B shows the expandable structure 1766 in a deployed state. As shown, the expandable structure 1766 is disposed on the outer shaft 1760, such that the expandable structure 1766 covers the evacuation holes 1762a. Upon deployment of the expandable structure 1766, the expandable structure 1766 expands outward in a direction indicated by arrows 1792. In some embodiments, the expandable structure 1766 can create a mesh or include perforations or openings, such that in its expanded state, the expandable structure 1766 can act as a filter for fluids and/or debris entering the evacuation holes 1762a. In such a case, the expandable structure 1766 can act as a filter and prevent any debris large enough to clog the evacuation holes 1762a from entering the evacuation holes 1762a.

Figure 18A:
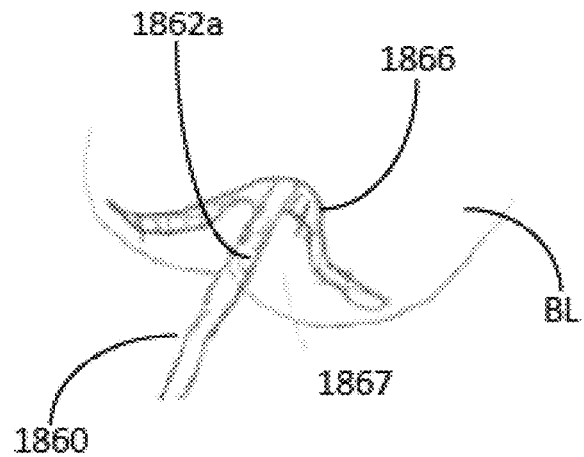
FIGS. 18A-18B are illustrations of an ablation catheter including an expandable mechanism and evacuation openings, according to an embodiment.
Figure 18B:
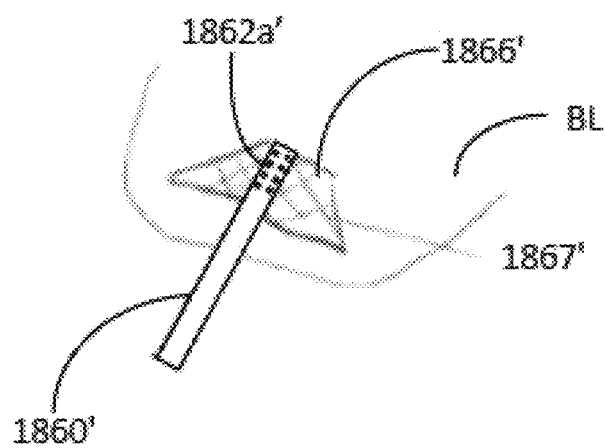

FIGS. 18A-18B show different arrangements of expandable structures of outer shafts of an ablation catheter, according to embodiments. FIGS. 18A-18B depict outer shafts 1860, 1860' of an ablation catheter (e.g., a cryoablation device), disposed in a body lumen BL. The outer shaft 1860, 1860' can include components that are structurally and/or functionally similar to other ablation systems and components thereof described herein (e.g., outer shaft 260, outer shaft 860, outer shaft 1060, inner shaft 1070, outer shaft 1660, outer shaft 1760, etc.). FIG. 18A shows the outer shaft 1860 with an expandable structure 1866, evacuation holes 1862a, and an evacuation pocket 1867. As shown, the evacuation holes 1862a are disposed in the body lumen BL when the outer shaft 1860 is positioned for an ablation procedure. The expandable structure 1866 can be configured to expand to form a curved or concave structure that defines an evacuation pocket 1867 around the evacuation holes 1862a. Stated differently, the expandable structure 1866 can form a shape similar to an umbrella that blocks debris from entering evacuation holes 1862a.

FIG. 18B shows the outer shaft 1860' with an expandable structure 1866', evacuation holes 1862a', and an evacuation pocket 1867'. As shown, the evacuation holes 1862a' are disposed in the body lumen BL. The expandable structure 1866' partially covers the evacuation holes 1862a' forming the evacuation pocket 1867'. As shown, the evacuation pocket 1867' is expanded such that it has a flat or substantially flat proximal side. This shape can form a secure engagement with the walls at the entry point of the body lumen BL to stabilize the outer shaft 1860' within the body lumen. This shape can ensure better retention of the outer shaft 1860' within in a body lumen such as, for example, a gallbladder.

Figure 19A:
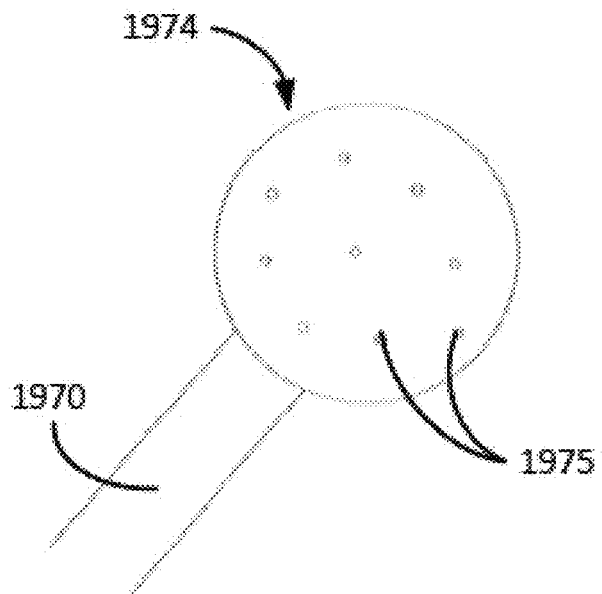
FIGS. 19A-19B are illustrations of an inner shaft of an ablation catheter with a spherical or rounded nozzle, according to an embodiment.
Figure 19B:
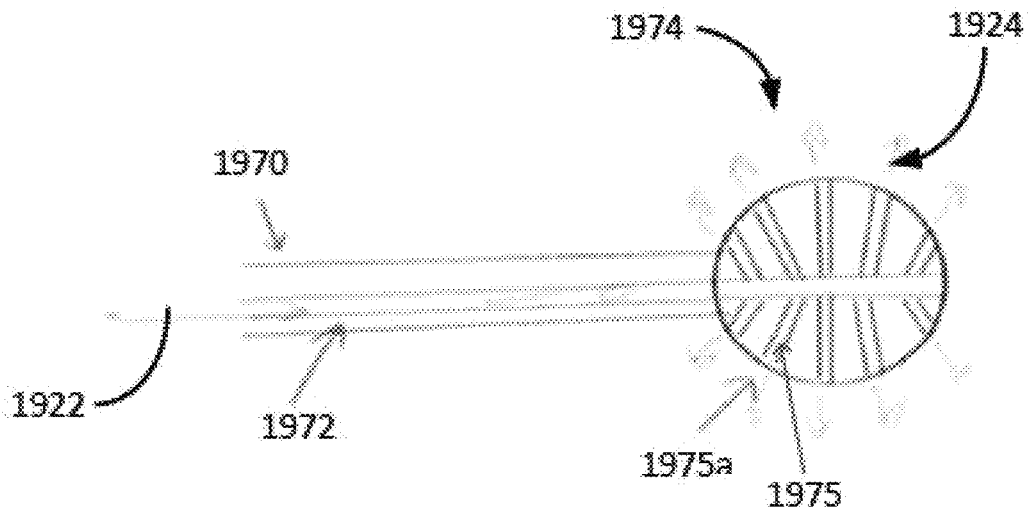
Figure 20:
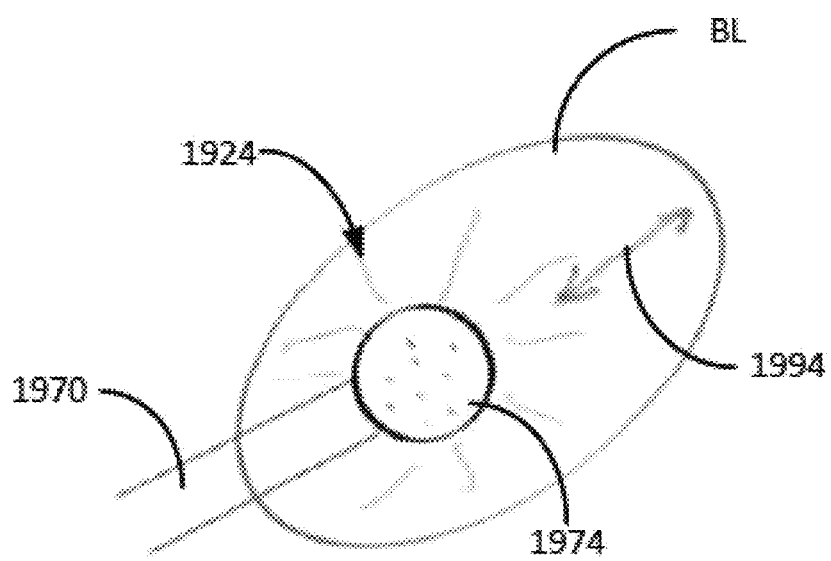
FIG. 20 is an illustration of an inner shaft of an ablation catheter with a spherical or rounded nozzle deployed into a body lumen, according to an embodiment.

FIGS. 19A-19B and FIG. 20 show example views of an inner shaft 1970 with a nozzle 1974 (e.g., a dispersion nozzle) located at the distal end of the inner shaft 1970, according to various embodiments. FIG. 19A illustrates a perspective view of the inner shaft 1970 while FIG. 19B illustrates a cross-sectional side view of the inner shaft 1970. The inner shaft 1970 can include components that are structurally and/or functionally similar to other ablation systems and components thereof described herein (e.g., inner shaft 270, inner shaft 870, inner shaft 1070, inner shaft 1670, etc.).

In some embodiments, the inner shaft 1970 can include a long catheter body with at least one delivery lumen 1972 that carries liquid ablation medium 1922 and terminates into the dispersion nozzle 1974. In some embodiments, the geometry of the dispersion nozzle 1974 is spherical and includes a series of holes 1975 that span from the outer diameter of the dispersion nozzle 1974 to the supply lumen 1972. In some embodiments, the dispersion nozzle 1974 uses liquid nitrous oxide as the ablation medium that undergoes a phase-change where the geometry of each hole 1975 intersects the outer surface of the dispersion nozzle 1974 (a phase-change interface 1975a). In other words, the liquid ablation medium 1922 transitions into a gas ablation medium 1924 near the outer surface of the dispersion nozzle 1974. In some embodiments, the holes 1975 are sufficiently small in size (e.g., on the order of about 0.0005"-0.004") to withstand the high pressures needed to keep a nitrous oxide in its liquid form until the cryogen reaches the desired phase-change interface 1975a. In some embodiments, the phase-change interface 1975a is controlled by a pressure drop (e.g., atmospheric venting) relative to the supply pressure of the liquid ablation medium 1922. In some embodiments, the phase change occurs when the liquid nitrous oxide is exposed to the near atmospheric pressure in a body lumen BL or other desired ablation area. In some embodiments, the phase change occurs at the wall of the body lumen BL; therefore fluid ablation medium can be delivered into the body lumen BL and contact the wall of the body lumen BL and phase change into a gas ablation medium. In such cases, ablation can occur at the liquid-gas phase change interface. As shown, the holes 1975 that are located on the proximal side of the nozzle 1974 are angled (e.g., angled proximally relative to a longitudinal axis of the inner shaft 1970), such that the gas ablation medium 1924 is dispensed at an angle toward a proximal region of a body lumen. The holes 1975 that are located on the distal side of the nozzle 1974 are angled (e.g., angled distally relative to a longitudinal axis of the inner shaft 1970), such that the gas ablation medium 1924 is dispersed at an angle toward a distal region of a body lumen. This angled configuration of the holes 1975 can aid in increasing distribution of the gas ablation medium 1924 throughout the body lumen.

Although illustrated as a spherical configuration, the geometry of the dispersion nozzle 1974 can be a cube, cone, cylinder, triangular prism, torus, helix, ovoid, or any other three dimensional (3D) body with sufficient structure to enable the delivery of ablation medium. In some embodiments, the dispersion nozzle 1974 can be made from metal, polymer, ceramic, or other structural material. In some embodiments, the maximum diameter of the distal geometry is sufficiently small to slide through an access catheter. In some embodiments, the dispersion nozzle 1974 can be expanded (e.g. inflated) to achieve a larger shape than the diameter of the access catheter.

FIG. 20 illustrates how the gas ablation medium 1924 is uniformly dispersed from the dispersion nozzle 1974 to the walls of the body lumen BL during use. In some embodiments, the inner shaft 1970 can move freely in an axial direction (i.e., along the axis indicated by line 1994) in order to sufficiently treat the walls of the body lumen BL with gas ablation medium 1924 throughout the axial length of the body lumen BL.

Figure 21:
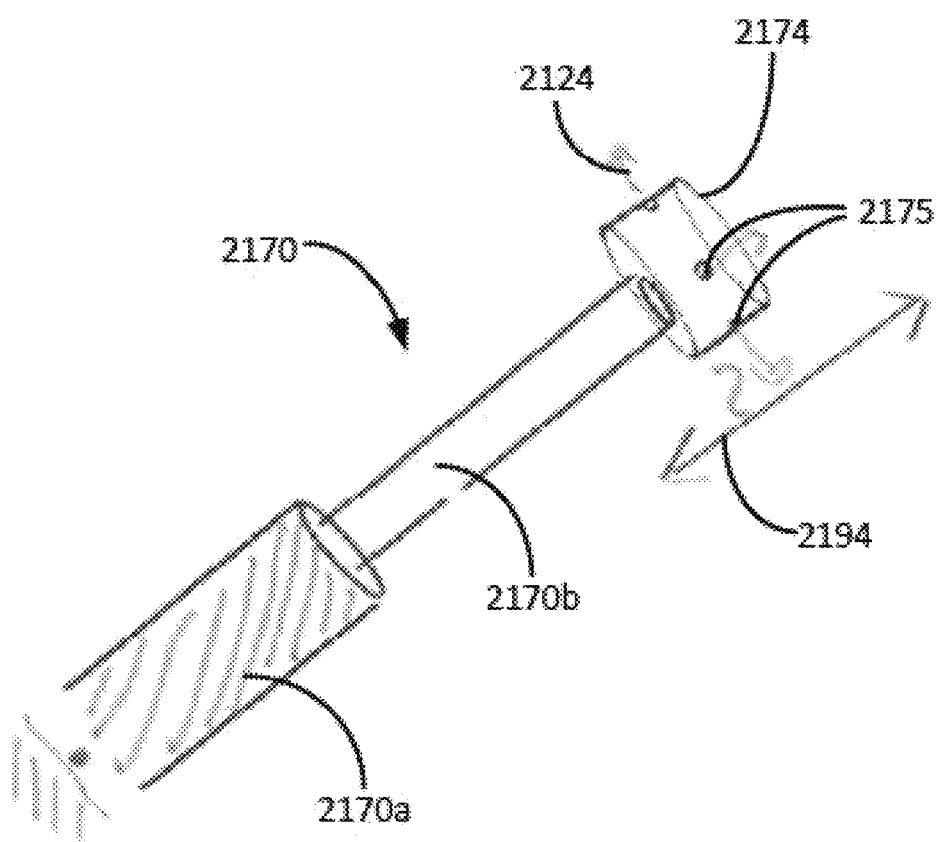
FIG. 21 is an illustration of an ablation catheter with a movable nozzle having a free end, according to an embodiment.

FIG. 21 shows an inner shaft 2170 with an actuated nozzle 2174 located near the distal end of the inner shaft 2170, according to an embodiment. The inner shaft 2170 can include components that are structurally and/or functionally similar to other ablation systems and components thereof described herein (e.g., inner shaft 270, inner shaft 870, inner shaft 1070, inner shaft 1670, inner shaft 1970, etc.). In some embodiments, gas ablation medium 2124 can be expelled via holes 2175 on the actuated nozzle 2174. In some embodiments, the inner shaft 2170 can include an inner shaft body 2170a and a linear rail component 2170b. In some embodiments, the actuated nozzle 2174 can be attached to the linear rail component 2170b. In some embodiments, the linear rail component 2170b allows the actuated nozzle 2174 to move axially (i.e., along the line indicated by arrow 2194) in response to a driving force. In some embodiments, the linear rail component 2170b allows the actuated nozzle 2174 to move non-linearly along its central axis in response to a driving force.

In some embodiments, the driving force is either manually or automatically applied such as via a control unit (e.g., control unit 110). In some embodiments, the driving force can be manually or automatically be applied using a stiff drive wire system, a flexible drive cable system, a mating gear drive system, a rack-and-pinion system, a screw-drive mechanism, a pneumatic actuator system, an electromagnetic coil system, a hydraulic actuator system, or any other type of system as can be appreciated. In some embodiments, the driving force is the user's grip force, pull force, twist force or squeeze force. In some embodiments, the driving force can be electromechanical, such as the use of electrical current to drive an AC/DC motor or the use of electromagnetic fields.

In some embodiments, the linear rail component 2170b can be fixed or nearly fixed by a distal and proximal feature to the linear rail component 2170b. In some embodiments, the linear rail component 2170b can be fixed or nearly fixed by only a proximal feature to the rail. In some embodiments, the linear rail component 2170b can be fixed or nearly fixed by only a distal feature to the linear rail component 2170b. In some embodiments, the distal feature can be a cystic duct occlusion mechanism. In some embodiments, the proximal feature is an access catheter lumen.

In some embodiments, the actuated nozzle 2174 can be similar to the nozzles described in FIGS. 19A, 19B, and FIG. 20, according to various embodiments. In some embodiments, the diameter of the hole or holes 2175 located on the actuated nozzle 2174 can vary in diameter, relative to their position. In some cases, the holes 2175 can be "tapered" or increase/decrease in diameter, along the geometry, to deliver a constant mass flow rate of gas ablation medium 2124 and combat the effects of pressure drop in an ablation supply lumen.

In some embodiments, the size, shape, and number of holes 2175 emanating from the supply lumen will determine the spray pattern, spray velocity, and spray uniformity of the ablation medium. In some embodiments, some of the holes 2175 are optimized to target close targets (e.g., 0-0.5 cm). In some embodiments, some of the holes 2175 are optimized to target distant targets (e.g., greater than 0.5 cm).

In some embodiments, the actuated nozzle 2174 is able to spin along its central axis, rotating the holes 2175 relative to their starting position. In some embodiments, the actuated nozzle 2174 is able to spin between 0-360 degrees or any inclusive range. In at some embodiments, the rotating actuated nozzle 2174 allows for greater coverage of ablation medium delivery.

In some embodiments, the actuated nozzle 2174 can be fixed relative to the distal end of the linear rail component 2170b and can move with the displacement of the linear rail component 2170b by the driving force.

In some embodiments, the linear rail component 2170b can facilitate either concentric or non-concentric movement of the actuated nozzle 2174 between about 0-10 cm or any inclusive range in response to a driving force.

Figure 22:
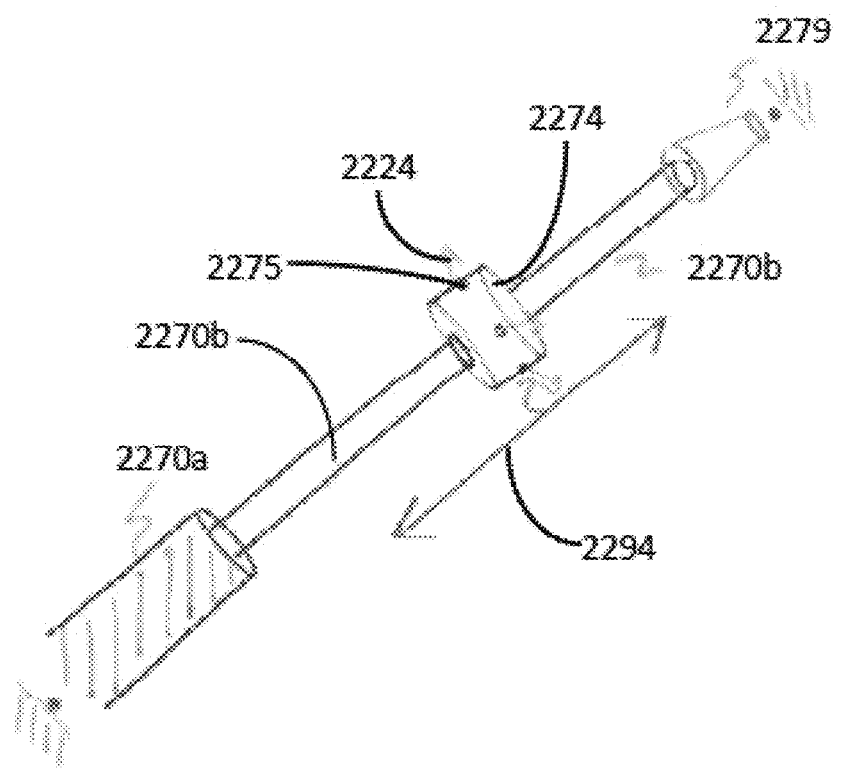
FIG. 22 is an illustration of an ablation catheter with a movable nozzle having a fixed end (e.g., fixed using an occluder), according to an embodiment.

FIG. 22 shows an inner shaft 2270 with an actuated nozzle 2274 located near the distal end of the inner shaft 2270, according to an embodiment. The inner shaft 2270 can include components that are structurally and/or functionally similar to other ablation systems and components thereof described herein (e.g., inner shaft 270, inner shaft 870, inner shaft 1070, inner shaft 1670, inner shaft 1970, inner shaft 2170, etc.). In some embodiments, gas ablation medium 2224 can be expelled via holes 2275 on the actuated nozzle 2274. In some embodiments, the inner shaft 2270 can include an inner shaft body 2270a and a linear rail component 2270b. In some embodiments, the actuated nozzle 2274 can move in an axial direction (i.e., along the line indicated by arrow 2294) along the linear rail component 2270b in response to a driving force. In some embodiments, the inner shaft 2270, the actuated nozzle 2274, the holes 2275, the inner shaft body 2270a, and the linear rail component 2270b can be the same or substantially similar to the inner shaft 2170, the actuated nozzle 2174, the holes 2175, the inner shaft body 2170a, and the linear rail component 2170b, as described above with reference to FIG. 21.

The inner shaft 2270 also includes an occluder 2279. The occluder 2279 can be configured to occlude or close an opening or lumen outlet into nearby anatomical structures from a body lumen. For example, in the case where the body lumen is a gallbladder lumen, the occluder 2279 can be configured to occlude a cystic duct. The occluder 2279 can be coupled to and/or detachable from the inner shaft 2270. In operation, the occluder 2279 can be coupled to a distal end of the inner shaft 2270. In some embodiments, the occluder 2279 can be coupled to the linear rail component 2270b. The inner shaft 2270 can be navigated into the body lumen. The inner shaft 2270 can be manipulated to position the occluder 2279 at an opening out of the body lumen (e.g. outlet lumen such as a cystic duct). The occluder 2279 can then be decoupled or ejected from the inner shaft 2270, allowing the occluder 2279 to be placed in the opening. The occluder 2729 can subsequently be fixed in place, e.g., via volume expansion of the occluder 2279, external threads, friction fit, adhesion, or other suitable fixation mechanism. Further details of suitable occluders such as, for example, plugs, are described in International Patent Application No. PCT/US2019/017112, incorporated herein by reference.

Figure 23:
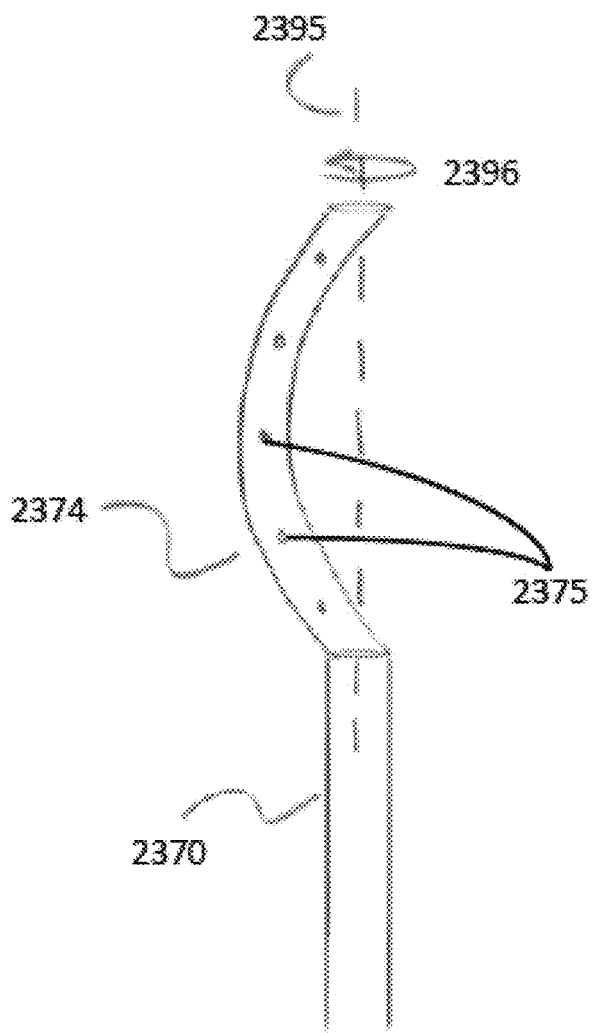
FIG. 23 is an illustration of an ablation catheter with a bowed nozzle, according to an embodiment.
Figure 24:
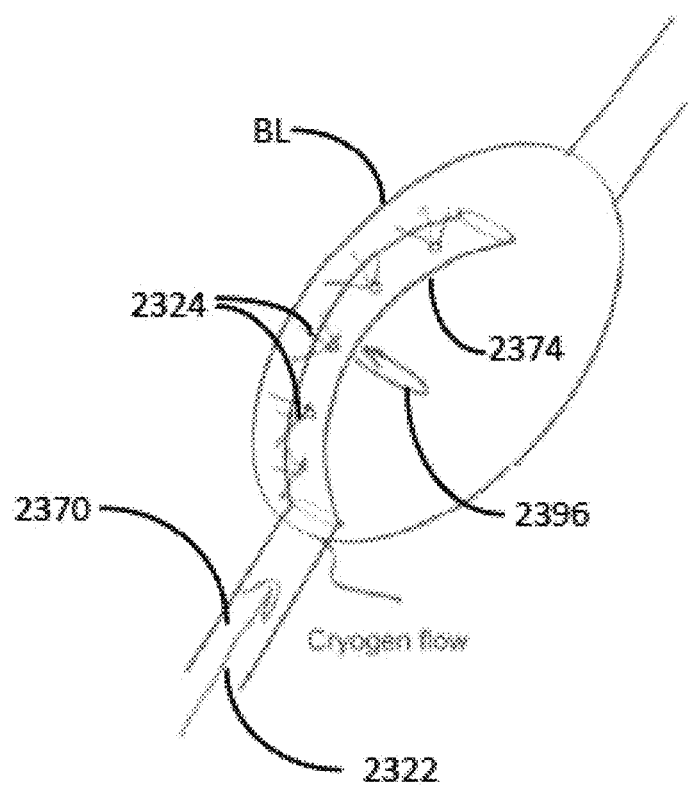
FIG. 24 is an illustration of an ablation catheter with a bowed nozzle deployed in a body lumen, according to an embodiment.

FIGS. 23-24 show an inner shaft 2370 having a nozzle 2374 with a bowed design that can increase the effective spray area of an ablation medium. The inner shaft 2370 can include components that are structurally and/or functionally similar to other ablation systems and components thereof described herein (e.g., inner shaft 270, inner shaft 870, inner shaft 1070, inner shaft 1670, inner shaft 1970, inner shaft 2170, inner shaft 2270, etc.). In some embodiments, the nozzle 2374 has at least one bowed segment that contains at least one hole 2375 emanating from a supply lumen. In some embodiments, at the nozzle 2374 can rotate along its central axis 2395 (i.e., along arrow 2396) to uniformly deliver an ablation medium to the surface of a body lumen. FIG. 24 shows the inner shaft 2370 disposed in a body lumen BL. As shown, liquid ablation medium 2322 exits the nozzle 2374 via the holes 2375 and undergoes a phase change to become a gas ablation medium 2324.

In at least one embodiment, the diameter of the one or more holes 2375 located on the nozzle 2374 can vary in diameter, relative to their distance along the nozzle 2374. In some cases, the holes can be "tapered" or increase/decrease in diameter, between the proximal and distal end of the nozzle 2374, to deliver a constant mass flow rate of ablation medium and combat the effects of pressure drop in the supply lumen.

In some embodiments, the size, shape, and number of holes 2375 emanating from the supply lumen will determine the spray pattern, spray velocity, and spray uniformity of the ablation medium. In some embodiments, the entire nozzle 2374 can rotate and/or slide longitudinally, relative to its central axis 2395. In some embodiments, some of the holes 2375 are optimized to target close targets. In some embodiments, some of the holes 2375 are optimized to target distant targets.

Figure 25:
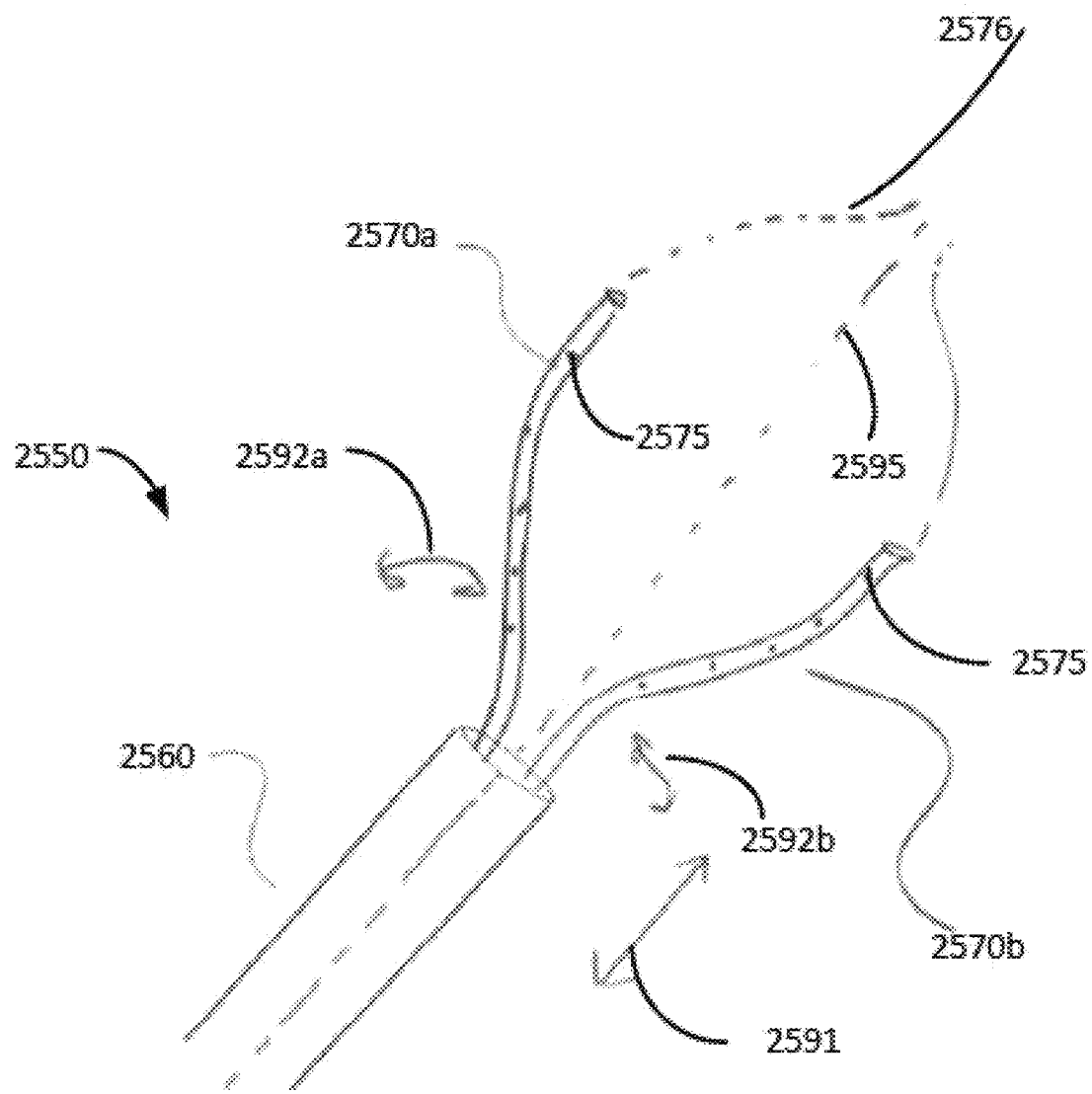
FIG. 25 is an illustration of an ablation catheter with nozzle arms, according to an embodiment.
Figures 26A, 26B:
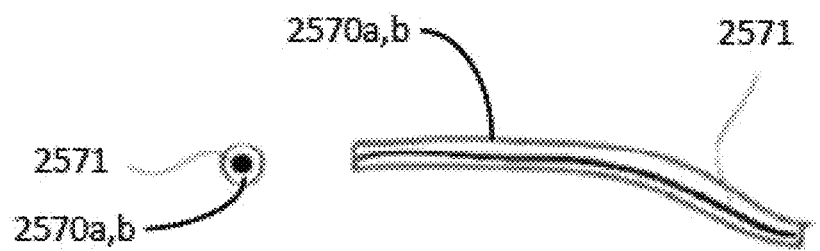
FIGS. 26A-26B are cross-sectional views of a nozzle arm of an ablation catheter, according to an embodiment.

FIGS. 25-26B show an ablation catheter 2550 with a collapsible cryogen dispersion nozzle, according to an embodiment. The ablation catheter 2550 can include components that are structurally and/or functionally similar to other ablation systems and components thereof described herein (e.g., ablation system 100, catheter system 250, control unit 310, cryoablation device 800, ablation catheter 1050, etc.). The ablation catheter 2550 includes an outer shaft 2560, a first inner shaft 2570a, and a second inner shaft 2570b. In some embodiments, the ablation catheter 2550 can include an expandable structure 2576. In some embodiments, the inner shafts 2570a, 2570b (collectively referred to as inner shafts 2570) can be coupled to the expandable structure 2576. In some embodiments, the inner shafts 2570 can be uncoupled at their distal ends. In other words, the ablation catheter 2550 can be without an expandable structure 2576. The inner shafts 2570 include holes 2575 for the delivery of ablation medium. In some embodiments, the inner shafts 2570a can move along the line indicated by arrow 2591. In some embodiments, the inner shafts 2570 can be rotated around a central axis 2595 (i.e., along paths indicated by arrows 2592a, 2592b). As shown, the ablation catheter 2550 includes two inner shafts 2570. In some embodiments, the ablation catheter 2550 can include 3, 4, 5, 6, 7, 8, 9, 10, 11, 12, 13, 14, 15, 16, 17, 18, 19, 20, or more inner shafts 2570. As shown, the inner shafts 2570, extend a partial length of the expandable structure 2576. In some embodiments, the inner shafts 2570 can extend the entire length of the expandable structure 2576, such that the inner shafts 2570 are coupled together at a distal end of the ablation catheter 2550.

In some embodiments, at least of the inner shafts 2570 forms a bowed shape along the central axis 2595 that extends to a maximum radial dimension and converges back towards the central axis 2595 to bring the holes 2575 closer to the target ablation site. In some embodiments, the ablation catheter 2550 uses liquid nitrous oxide as an ablation medium and is configured such that the phase-change interface of the ablation medium is located on the outer surface of the inner shafts 2570.

In some embodiments, the inner shafts 2570 can be spring-loaded and can collapse to be delivered through a smaller diameter delivery lumen, relative to the nominal expanded diameter of the inner shafts 2570.

FIGS. 26A-26B show the inner shafts 2570 in greater detail. FIG. 26A shows a cross-sectional view of the inner shafts 2570, while FIG. 26B shows a side view of the inner shafts 2570. In some embodiments, the ablation catheter 2550 can be constructed with a pre-shaped core 2571 within the inner shafts 2570 that exerts a return force when subjected to mechanical stress, thermal energy, electrical current, or light. In some embodiments, the pre-shaped core 2541 can be made from an alloy metal, such as Nitinol or spring steel. In some embodiments, the pre-shaped core 2571 can be made from a polymer, such as acrylonitrile butadiene styrene (ABS). In some embodiments, the inner shafts 2570 can be driven to an expanded conformation by a mechanical driving force, such as rack and pinion gear system, a cable drive system, or electromechanical control system. In some embodiments, the inner shafts 2570 can be actuated along a linear or radial pathway to increase distribution of cryogen from the inner shafts 2570.

Figure 27A:
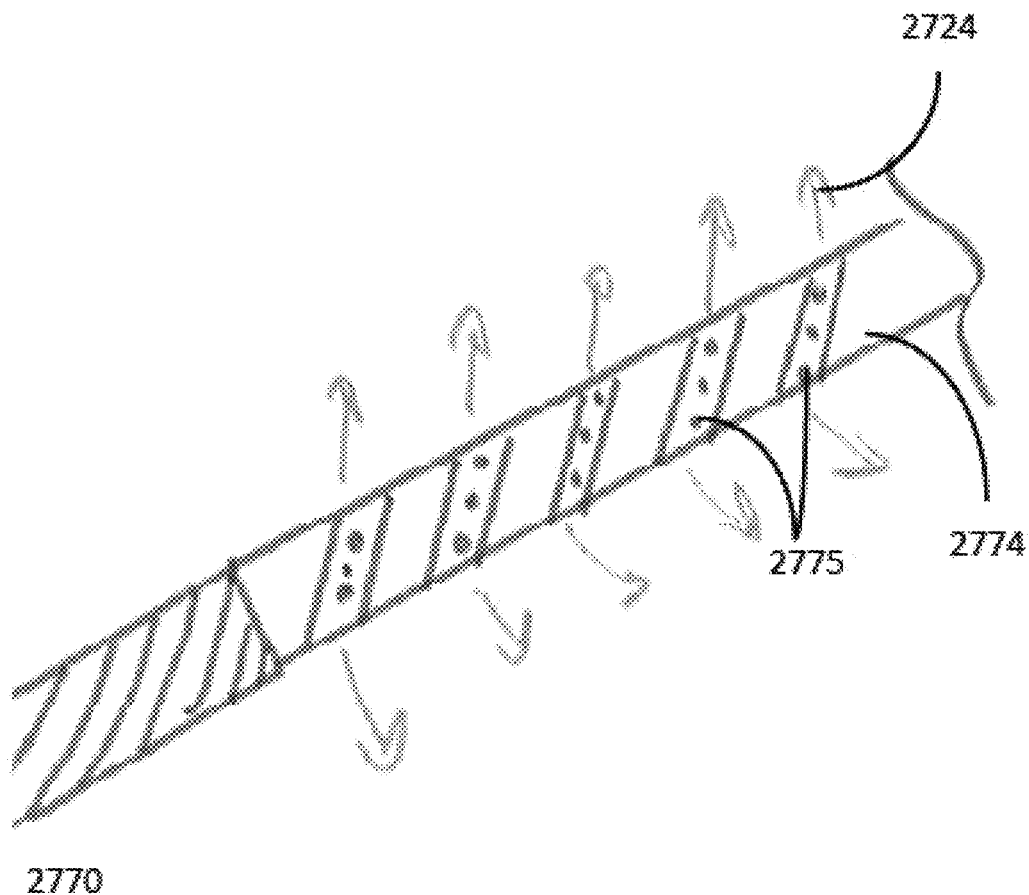
FIGS. 27A-27B are illustrations of an ablation catheter with a spiral nozzle, according to an embodiment.
Figure 27B:
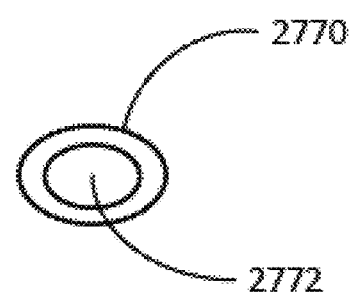

FIGS. 27A-27B show an inner shaft 2770 having a spiral nozzle 2774 with a number of holes 2775 emanating from at least one continuous supply lumen 2772. FIG. 27A shows a side view of the inner shaft 2770, while FIG. 27B shows a cross-sectional view of the inner shaft 2770. The inner shaft 2770 can include components that are structurally and/or functionally similar to other ablation systems and components thereof described herein (e.g., inner shaft 270, inner shaft 870, inner shaft 1070, inner shaft 1670, inner shaft 1970, inner shaft 2170, inner shaft 2270, etc.). Gas ablation medium 2724 is shown exiting the inner shaft 2770 via the holes 2775. In some embodiments, the spiral nozzle 2774 can be mounted around a structural body that holds the spiral conformation of the spiral nozzle 2774. In some embodiments, the holes 2775 can vary in size, shape, and location depending on the desired spray pattern. In some embodiments, the holes 2775 can "taper" or increase/decrease along the nozzle 2774, relative to their distance along the nozzle 2774, to maintain a desired mass flow rate along each of the holes 2775. In some embodiments, the aforementioned design allows for a minimal distance between the phase change surface and the supply lumen 2772, so as to minimize variability in spray patterns between holes.

FIG. 28 shows an ablation catheter 2850 with an outer shaft 2860 and an inner shaft 2870. The ablation catheter 2850 can include components that are structurally and/or functionally similar to other ablation systems and components thereof described herein (e.g., ablation system 100, catheter system 250, control unit 310, cryoablation device 800, ablation catheter 1050, etc.). Ablation medium 2826 can be evacuated from a body lumen through the outer shaft 2860. In some embodiments, heating coils 2882 can be deployed around the outside of the outer shaft 2860. In some embodiments, heating coils 2884 can be deployed around the outside of the inner shaft 2870. According to various embodiments of the present disclosure, the cryoablation devices of the present disclosure are designed to leverage the phase-change properties of liquid nitrous oxide ($N_2O$ or $LN_2O$), to induce cryoablation temperatures (e.g., about −80 C) at the target tissue interface. $N_2O$ is a clear liquid at ambient temperatures and high pressures (>650 psi), but undergoes a phase change from liquid to gas when it experiences a sufficient pressure drop, resulting in an endothermic reaction that produces a refrigerant property. Further, while liquid nitrous oxide affords a unique refrigerant property that is well suited for cryoablation applications, it can present safety issues as the volume of the gas can increase 600-fold or more during the phase change, creating a source of pressure build up within the lumen. In order to combat this risk, the cryoablation devices of the present disclosure can be designed to utilize a passive evacuation management system to vent cryogen gas out of the body during the procedure. For example, systems, devices, and methods described herein can allow flow of ablation medium through a concentric lumen space between an (e.g., inner shaft 2870) and an outer shaft (e.g., outer shaft 2860) of an ablation catheter. Pressure driven flow can cause the ablation medium to enter the lumen space between the inner shaft and the outer shaft and exit out an exhaust port at a proximal end of ablation catheter.

In addition, liquid nitrous oxide has a melting point within a few degrees Celsius of its boiling point, i.e., a small margin exists between its gas phase and solid phase. Such can lead to solid nitrous oxide ice buildup if the pressure and temperatures within the outer shaft and the inner shaft are not controlled properly. Solid nitrous ice buildup, in conjunction with remnant fluid within the gallbladder, can lead to clogging of the evacuation lumen in certain circumstances. This can cause pressure build-up within the gallbladder lumen and is a safety concern. To directly combat icing of the evacuation lumen, the heating coils 2882, 2884 can be applied to melt or evaporate ice build-up.

FIGS. 29A-29B show views of an ablation catheter 2950 with a catheter heating system configured to combat ice build-up in the evacuation lumen, according to various embodiments of the present disclosure. The ablation catheter 2950 can include components that are structurally and/or functionally similar to other ablation systems and components thereof described herein (e.g., ablation system 100, catheter system 250, control unit 310, cryoablation device 800, ablation catheter 1050, etc.). As shown, the ablation catheter 2950 includes an outer shaft 2960 and an inner shaft 2970. The inner shaft 2970 includes a nozzle 2974. In some embodiments, a heating coil 2982 can be wrapped around (e.g., disposed around) the outside of the outer shaft 2960. In some embodiments, a heating coil 2984 can be wrapped around (e.g., disposed around) the outside of the inner shaft 2970. In particular, FIG. 29A illustrates an example view of a catheter heating system designed to defrost cryogen ice build-up within a lumen. The catheter heating system of FIG. 29A includes a multi-surface heating system in which the outer face of the outer shaft 2960 and the outer face of the inner shaft 2970 are heated to vaporize ice-build up and maintain the patency of the annular space between the two shafts. FIG. 29B shows a ablation catheter 2950' with a single surface heating system in which the outer face of the outer shaft 2960 is heated via heating coil 2982 to vaporize ice-build up and maintain the patency of the annular space between the inner shaft 2970 and the outer shaft 2960.

In some embodiments, the heating coils 2982, 2984 can include a resistive heating element, such as, for example, a resistive wire, that transfers electrical energy into heat, thereby conductively heating nearby bodies. In some embodiments, the resistive heating wire is wrapped around the outer circumference of the outer shaft 2960. In some embodiments, the resistive heating wire is wrapped around the inner circumference of the outer shaft 2960. In at least one embodiment, the resistive heating wire is embedded within the outer shaft 2960 wall material.

In some embodiments, the resistive heating wire is wrapped in a helical coil configuration with about 0-1" pitch spacing, including all subranges and values in between. In some embodiments, the resistive heating wire is wrapped in a helical coil configuration with a fixed pitch. In another embodiment, the resistive heating wire is wrapped in a helical coil configuration with a variable or "progressive fix" such that the sections of tighter coil pitch are located closer to the distal end of the outer shaft 2960. In the aforementioned configuration, the tighter pitch section enables greater heat density, compared to looser pitch sections, thereby heating the bodies surrounding the tighter pitch section more. Such can localize the heating energy of the coil and minimize competing effects on the therapy.

In some embodiments, the outer shaft 2960 can be polymer, metal, ceramic, or composite or any combination of. In some embodiments, a metal or high thermal conductance material can span parts and the entirety of the outer shaft 2960 wall thickness and circumference to increase the heat transfer rate to the desired heating target. In some embodiments, the delivery lumen can have a metal segment near the distal end of the outer shaft 2960 to concentrate the effect of the heating coil 2982. In some embodiments, an insulating material can be used to electrically and/or thermally insulate the heating coil 2982 from surrounding bodies.

Figure 30A:
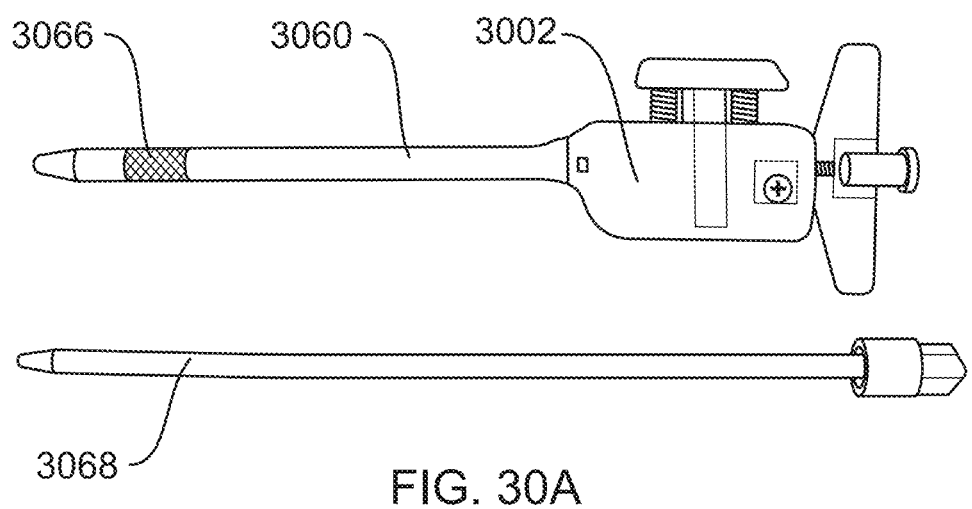
FIGS. 30A-30B are illustrations of an outer shaft of an ablation catheter and a dilator, according to an embodiment.
Figure 30B:
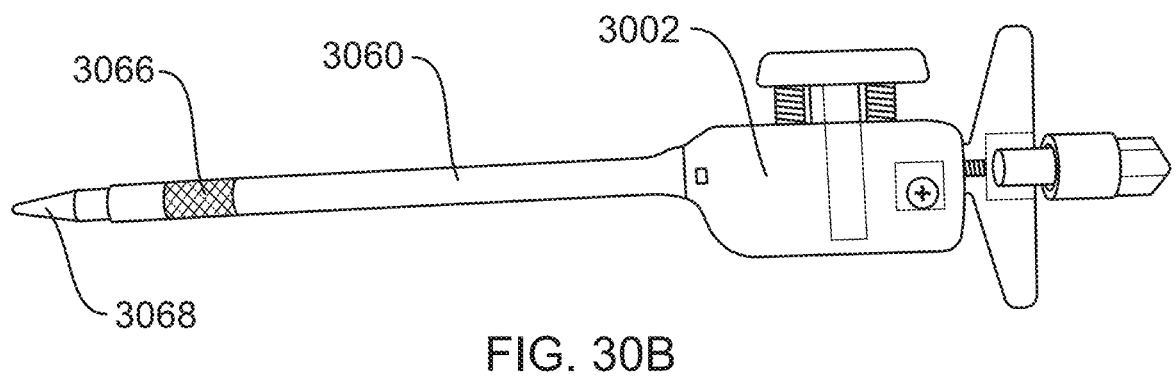

FIGS. 30A-33 show an ablation catheter 3050 in various stages of assembly. FIGS. 30A-30B show an outer shaft 3060 and a dilator 3068, according to an embodiment. The ablation catheter 3250 can include components that are structurally and/or functionally similar to other ablation systems and components thereof described herein (e.g., ablation system 100, catheter system 250, control unit 310, cryoablation device 800, ablation catheter 1050, etc.). The outer shaft 3060 includes a handle assembly 3002 and an expandable structure 3066. In some embodiments, the deployment of the expandable structure 3066 can be controlled by the handle assembly 3002. FIG. 30A shows the outer shaft 3060 separated from the dilator 3068. FIG. 30B shows the dilator 3068 secured in the outer shaft 3060. In some embodiments, the dilator 3068 can be used to securely fit the outer shaft around a guidewire during insertion into a body lumen, as described above with reference to FIGS. 6A-6B. In some embodiments, the dilator 3068 can be secured in the outer shaft 3060 via a threading.

Figure 31A:
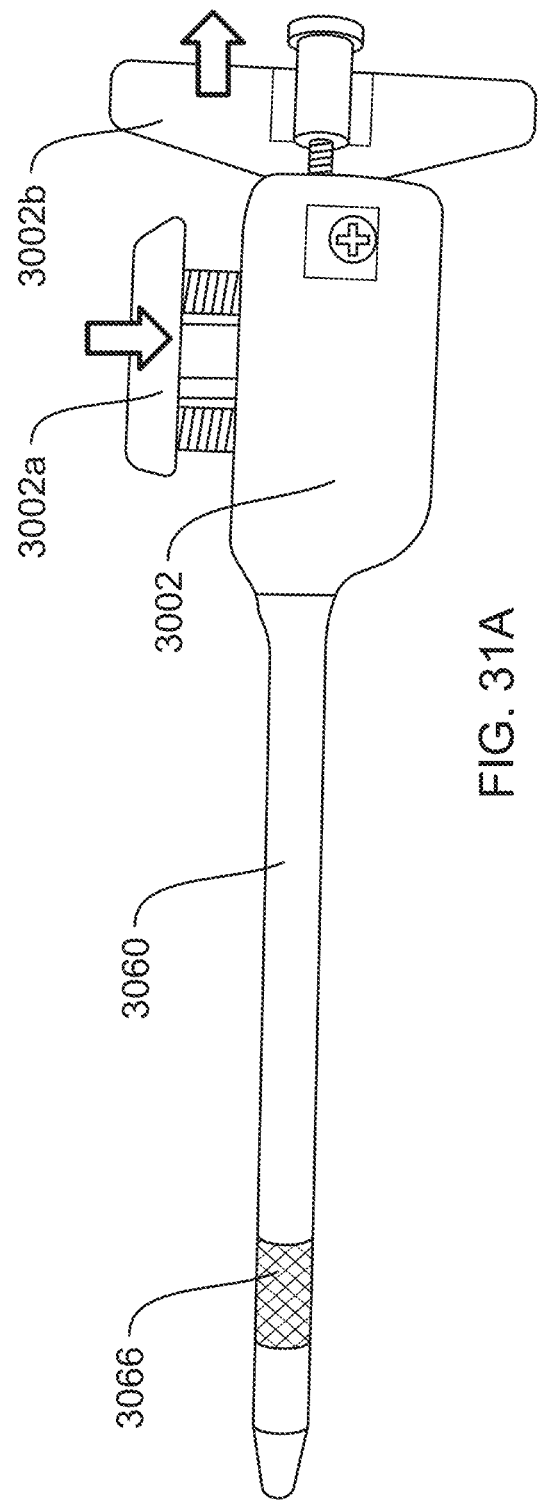
FIGS. 31A-31B are illustrations of an outer shaft of an ablation catheter with an expandable structure in an undeployed state and a deployed state, according to an embodiment.
Figure 31B:
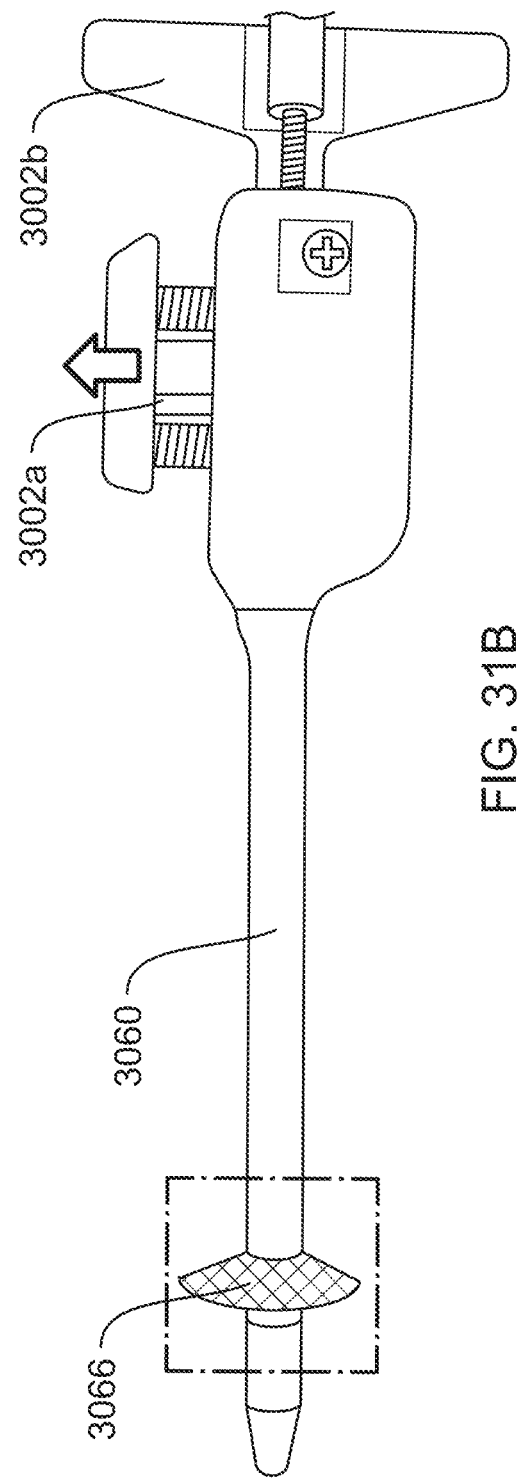

FIGS. 31A-31B show the outer shaft 3060 with an expandable structure 3066 in an undeployed state (FIG. 31A) and a deployed state (FIG. 31B), according to an embodiment. As shown, the handle assembly 3002 includes a button 3002a and a handle 3002b. In some embodiments, pushing the button 3002a can unlock the mechanism that controls the deployment of the expandable structure 3066. After the mechanism is unlocked, the handle 3002b can be pulled to actuate the expandable structure 3066 into the deployed state. Once the expandable structure 3066 is in the deployed state, the button 3002a can be released to lock the expandable structure 3066 in the deployed state.

Figure 32A:
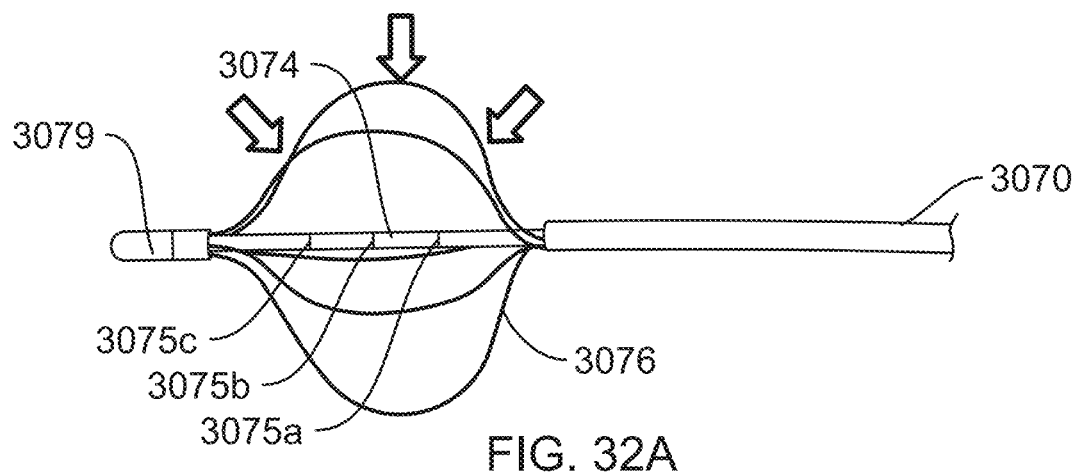
FIGS. 32A-32C are illustrations of an inner shaft of an ablation catheter with an actuator, according to an embodiment.
Figure 32B:
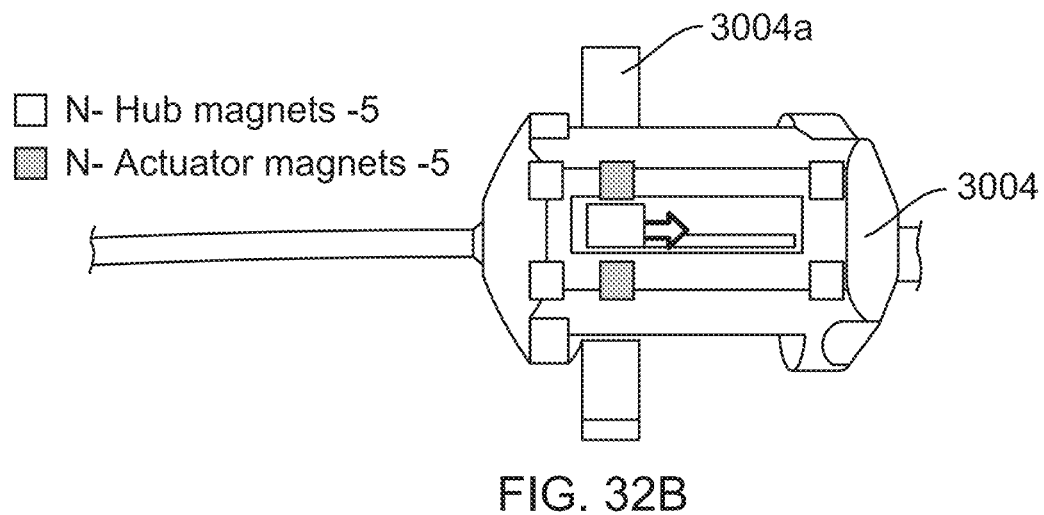
Figure 32C:
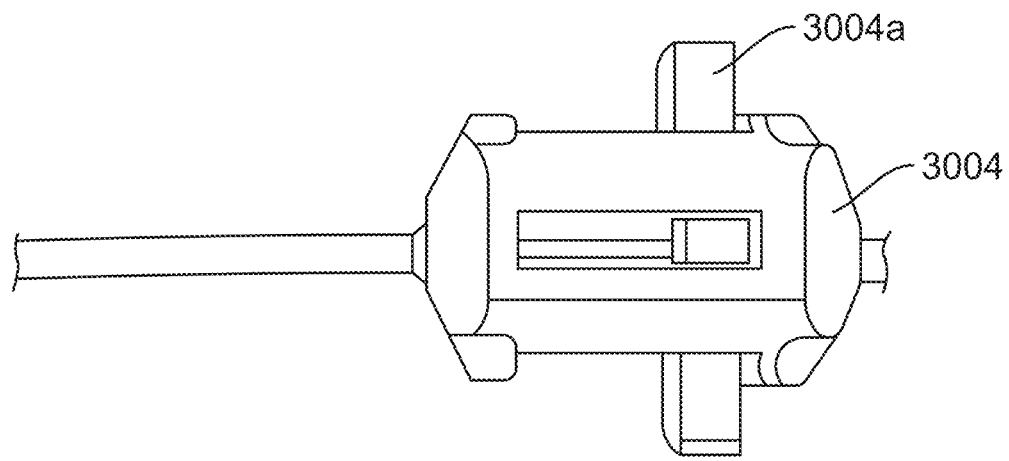

FIGS. 32A-32C are illustrations of an inner shaft 3070 with an actuator handle assembly 3004, according to an embodiment. The actuator handle assembly 3004 includes an actuator handle 3004a. The inner shaft 3070 includes a nozzle 3074, an expandable structure 3076, and a hub 3079. The nozzle 3074 includes holes 3075a, 3075b, 3075c (collectively referred to as holes 3075). As shown, the holes 3075a in a proximal position are angled, such that an ablation medium exits the nozzle 3074 in a slightly proximal direction. As shown, the holes 3075c in a distal position are angled, such that an ablation medium exits the nozzle 3074 in a slightly distal direction. Advantages of such an angled configuration of the holes 3075 are described above with reference to the holes 1975 in FIGS. 19A-19B.

As shown, FIG. 32A shows detail of the expandable structure 3276, while FIG. 32B shows the actuator handle 3004a positioned such that the expandable structure 3076 is in a deployed state, and FIG. 32C shows the actuator handle 3004a positioned such that the expandable structure 3076 is in an undeployed state. In some embodiments, the actuator handle 3004a can be fixed in position by magnets. For example, the actuator handle assembly 3004 can include magnets on both a proximal side and a distal side, and the actuator handle 3004a can include magnets such that the actuator handle 3004a is attracted to the proximal side and the distal side of the actuator handle assembly 3004. In such a case, the actuator handle 3004a can be more attracted to whichever side of the actuator handle assembly 3004 is closer.

Figure 33:
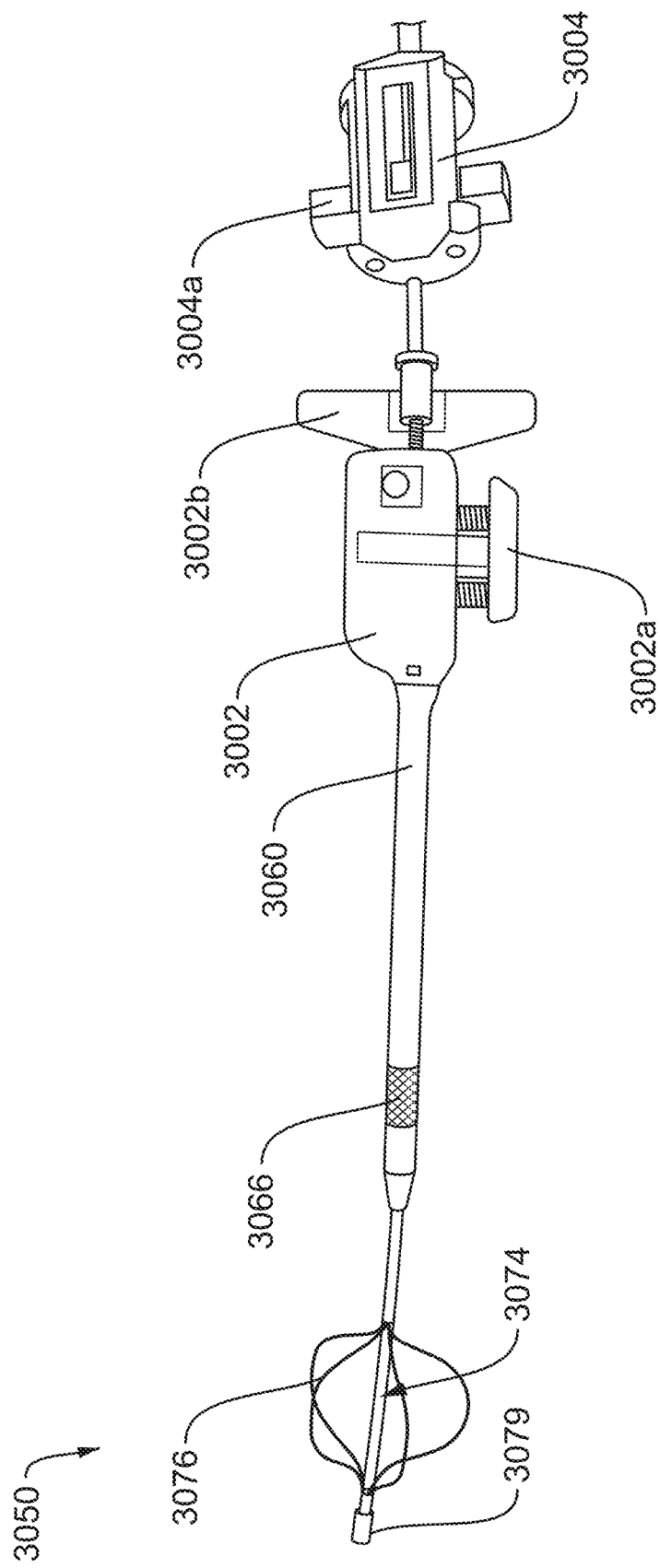
FIG. 33 is an illustration of an assembled ablation catheter, according to an embodiment.

FIG. 33 shows an assembled ablation catheter 3050, with the inner shaft 3070 disposed within and/or coupled to the outer shaft 3060. As shown, the expandable structure 3066 is in the undeployed state and the expandable structure 3076 is in the deployed state. As shown, the actuator handle 3004a is coupled to the actuator handle assembly 3004. In some embodiments, the actuator handle 3004a can be coupled to the actuator handle assembly 3004. In some embodiments, the button 3002a can be disposed in the handle assembly 3002. In some embodiments, the button 3002a can be coupled to the handle assembly 3002. In some embodiments, the handle 3002b can be disposed in the handle assembly 3002. In some embodiments, the handle 3002b can be coupled to the handle assembly 3002.

Figure 34A:
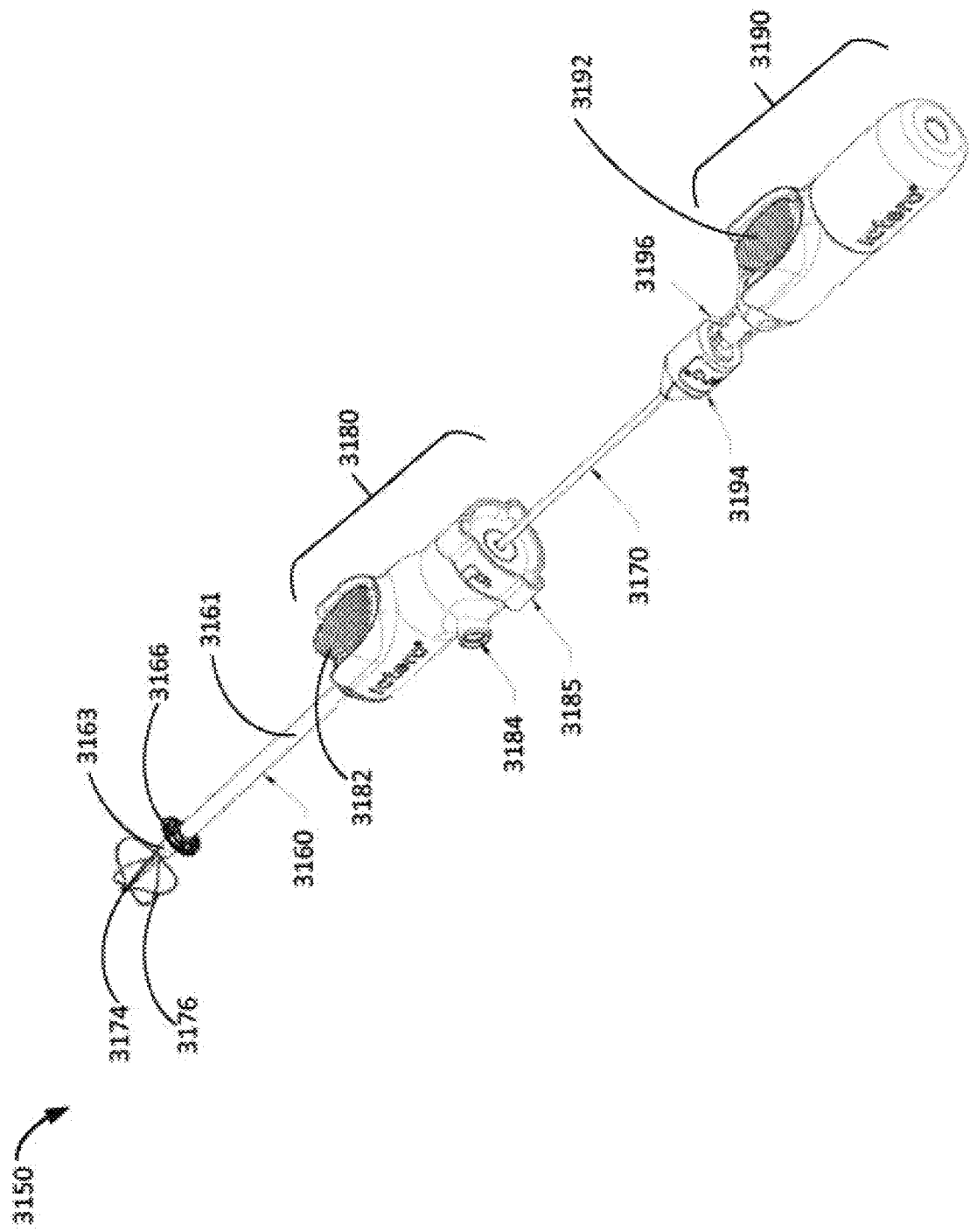
FIGS. 34A-34B are illustrations of an ablation catheter, according to an embodiment.
Figure 34B:
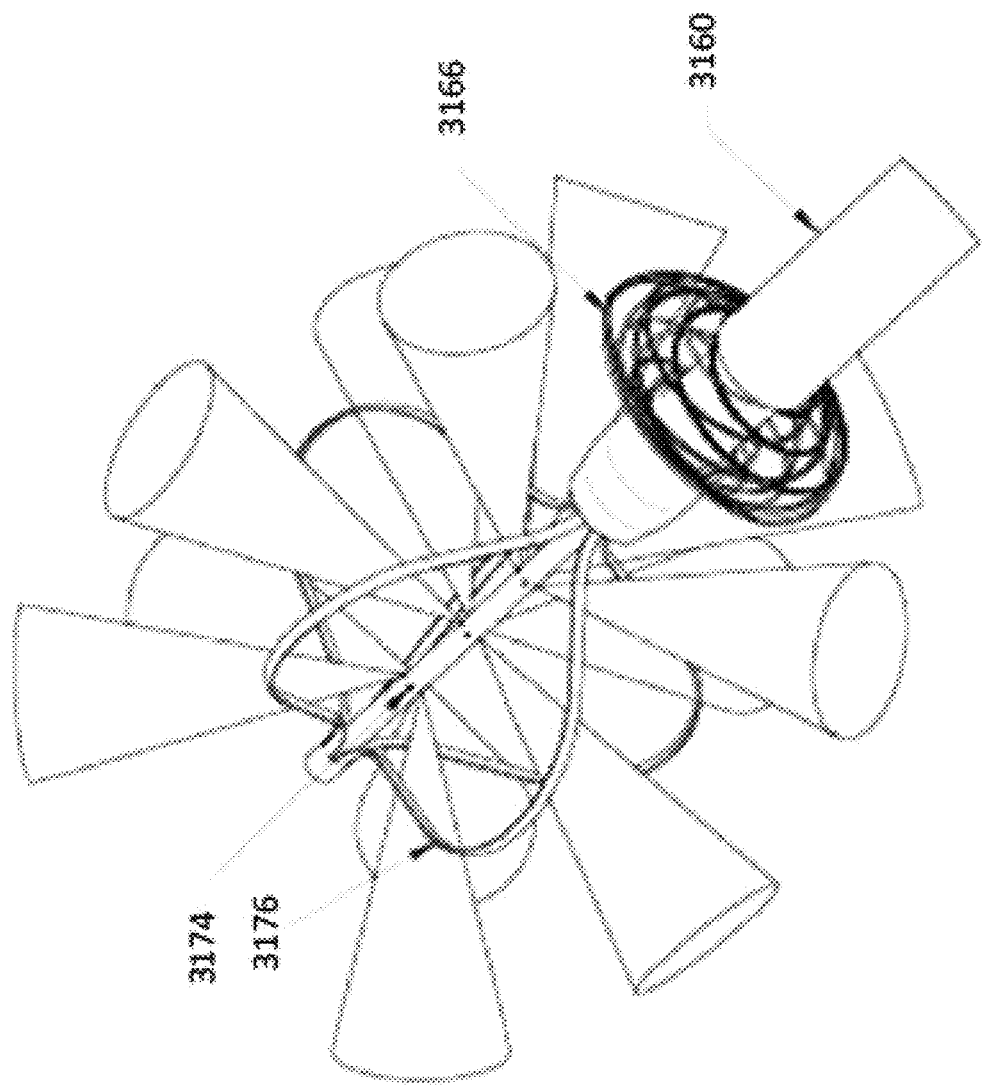

FIGS. 34A-34B shows an ablation system 3150 with a handle assembly including multiple handles, according to an embodiment. FIG. 34A shows the ablation system 3150, while FIG. 34B shows a spray pattern of nozzles of the ablation system 3150. As shown, the ablation system 3150 includes an outer shaft 3160, an expandable structure 3166 (e.g., retention mechanism), an inner shaft 3170, a nozzle 3174, an expandable structure 3176 (e.g., an expandable body or cage), an outer shaft (introducer or access sheath) handle 3180, an outer shaft (introducer or access sheath) handle button 3182, an evacuation chamber port 3184, an evacuation chamber collar 3185, an inner shaft (catheter) handle 3190, an inner shaft (catheter) handle button 3192, a wire termination collar 3194, and a heated sheath plug 3196. In some embodiments, the outer shaft 3160, the expandable structure 3166, the inner shaft 3170, the nozzle 3174, and the expandable structure 3176 can be the same or substantially similar to the outer shaft 3060, the expandable structure 3066, the inner shaft 3070, the nozzle 3074, and the expandable structure 3076, as described above with reference to FIG. 33. Thus, certain aspects of the outer shaft 3160, the expandable structure 3166, the inner shaft 3170, the nozzle 3174, and the expandable structure 3176 are not described in greater detail herein.

In some embodiments, the user can push the outer shaft handle button 3182 to advance an outer liner or sheath 3161 of the outer shaft 3160 distally. Advancement of the outer liner 3161 relative to a tip 3163 of the outer shaft 3160 can cause the expandable structure 3166 to expand (e.g., transition into an expanded configuration), such that the expandable structure 3166 can hold the tip 3163 in position inside the gallbladder. In some embodiments, the outer shaft handle 3180 can include a locking mechanism (not shown), such that the liner 3161 of the outer shaft 3160 can lock into position relative to the tip 3163. The evacuation chamber port 3184 is in fluidic communication with the interior of the outer shaft 3160. Cryoablation medium can flow through the interior of the outer shaft 3160 and exit the ablation system 3150 via the evacuation chamber port 3184. In some embodiments, the evacuation chamber port 3184 can be connected to a hose and/or a vacuum line, such that cryoablation medium can be evacuated from the outer shaft 3160 and the handle assembly 3180 on demand.

The evacuation chamber collar 3185 fits around the outside of the inner shaft 3170. In some embodiments, the evacuation chamber collar 3185 can create a seal with the inner shaft 3170, such that the evacuation chamber collar 3185 can prevent liquid and/or gas (e.g., of the ablation medium) from leaking or flowing further along the inner shaft 3170.

The inner shaft handle 3190 includes an inner shaft handle button 3192. Pressing the inner shaft handle button 3192 can advance a portion of the inner shaft 3170 relative to the inner handle assembly 3190. In some embodiments, pressing the inner shaft handle button 3192 can advance one or more outer layers of the inner shaft 3170 relative to an inner ablation lumen of the inner shaft 3170. In some embodiments, the inner handle assembly 3190 can include a locking mechanism (not shown), such that the portion of the inner handle assembly 3180 that has been advanced can lock into position relative to the other portions of the inner shaft 3170. This movement of the portion of the inner shaft 3170 can be used to deploy the expandable structure 3176.

The wire termination collar 3194 couples to the inner shaft 3170 and can serve as a connection point between one or more heating elements, sensors, lumens, etc. and external sources. Alternatively, in some embodiments, the collar 3194 can be omitted and connections can be formed between one or more components of the inner shaft 3170 and external sources via another section of the handle 3190. In some embodiments, the collar 3194 can be configured to couple one or more heating wires of the inner shaft 3170 to an external heat source. In some embodiments, the wire termination collar 3194 can provide heat to the inner shaft 3170 via the internal heat source to prevent clogging due to freezing. Cryoablation medium can cause materials passing through the inner shaft 3170 and/or outer shaft 3160 to freeze, thereby clogging the pathway through the inner shaft 3170. By activating heating (e.g., via the external heat source coupled to one or more heating wires that extend along the inner shaft 3170), the heat applied to the inner shaft 3170 can melt frozen materials, allowing flow through the inner shaft 3170 and/or outer shaft 3160. In some embodiments, the wire termination collar 3194 can be coupled to the inner handle assembly 3190. The collar 3194 can include a heated sheath plug 3196 that is used to couple to an external heat source.

While not shown in detail in FIGS. 34A and 34B, the inner shaft 3170 defines a lumen that can deliver an ablation medium, such as, for example, cryoablation medium, to openings of the nozzle 3174. In some embodiments, the nozzle 3174 can be rotatable to adjust the location of the openings of the nozzle 3174 and where the ablation medium is being delivered. In some embodiments, the nozzle 3174 can actuate independently of the expandable structure 3176, e.g., be moved relative to the expandable structure 3174, to adjust the locations of the openings of the nozzle 3174 and where the ablation medium is being delivered.

In some embodiments, a pressure sensing lumen (not shown) can be disposed in one or more of the outer shaft 3160 and/or the inner shaft 3170. In some embodiments, the pressure sensing lumen can be fluidically coupled to a pressure sensor at a proximal end of the ablation system 3150 (not shown). In some embodiments, the pressure sensing lumen can terminate at an orifice that is disposed in the gallbladder cavity, while the pressure sensor is located outside of the gallbladder cavity. In other words, the pressure sensing lumen can fluidically couple an interior of the gallbladder cavity to the pressure sensor. In some embodiments, the pressure sensing lumen can be disposed about the inner shaft 3170. In some embodiments, the pressure sensing lumen can be disposed about the outer shaft 3160. In some embodiments, the pressure sensing lumen can be disposed in the inner shaft 3170. In some embodiments, the ablation system 3150 can include multiple pressure sensing lumens.

FIG. 34B shows spray patterns of the ablation system 3150, according an embodiment. As described above, the ablation system 3150 can be used to deliver an ablation medium, such as a cryoablation medium, via openings of the nozzle 3174. In some embodiments, the medium can be delivered as a fluid. In some embodiments, the medium can be delivered as a gas. In some embodiments, the medium can be delivered as a fluid that transitions into a gas at a point along the length of the ablation system 3150 and/or within the gallbladder lumen. As shown schematically in FIG. 34B, the spray pattern of the ablation medium exiting the ablating catheter 3150 via the openings of the nozzle 3174 can be conical. In other words, the ablation medium can be delivered via multiple spray zones that may or may not overlap with one another.

FIGS. 35A-35B provide more detailed views of an outer shaft 3260 and an outer shaft handle 3280 of an ablation system, according to an embodiment. FIG. 35A depicts a side view of the outer shaft 3260 and the outer shaft handle 3280, and FIG. 35B depicts a cross-sectional view of the outer shaft 3260 and the outer shaft handle 3280. As shown, the outer shaft 3260 includes an expandable structure 3266 (e.g., retention mechanism). The outer shaft 3260 is coupled to an outer shaft handle 3280. The outer shaft handle 3280 includes an outer shaft handle button 3282 and an evacuation chamber port 3284. In some embodiments, the outer shaft 3260, the expandable structure 3266, the outer shaft handle 3280, the outer shaft handle button 3282, and the evacuation chamber port 3284 can be the same or substantially similar to the outer shaft 3160, the expandable structure 3166, the outer shaft handle 3180, the outer shaft handle button 3182, and the evacuation chamber port 3184, as described above with reference to FIGS. 34A-34B. Thus, certain aspects of the outer shaft 3260, the expandable structure 3266, the outer shaft handle 3280, the outer shaft handle button 3282, and the evacuation chamber port 3284 are not described in greater detail herein. The outer shaft 3260 can define a lumen 3265 that can receive an inner shaft (e.g., an inner shaft of an ablation catheter, such as any of those described herein).

The handle 3280 can have a button 3282 that can be moved (e.g., slid) distally to advance an outer liner 3261 of the outer shaft 3260 relative to a tip 3263 of the outer shaft 3260. This advancement can be used to deploy the expandable structure 3266, e.g., transition the expandable structure 3266 from a collapsed state where it extends generally parallel to a longitudinal axis of the outer shaft 3260 to an expanded state where it bows radially outwards from the longitudinal axis. The expandable structure 3266 once deployed can be configured to retain the distal end of the outer shaft 3260 within an gallbladder lumen. In other words, the expandable structure 3266 can be configured to have a diameter in its expanded state that is larger than an opening through which the distal end of the outer shaft 3260 has used to gain access to the gallbladder lumen. As such, the expanded structure 3266 in its expanded state can rest against the walls of the gallbladder near that opening to retain the distal end of the outer shaft 3260 within the gallbladder lumen. The button 3282 can be locked by a spring 3281. The button 3282 can be depressed to unlock the button 3282 and then slid to advance the liner 3161. Once the button has slid its maximum distance (e.g., along a track), the button 3282 can be locked once again via a notch 3283 and the spring 3282 that presses the button 3282 into the notch. While a button is described as an example of an actuator (e.g., actuator 801a), it can be appreciated that any type of actuation mechanism can be used to advance and/or retract various components of the outer shaft 3260.

Figure 36:
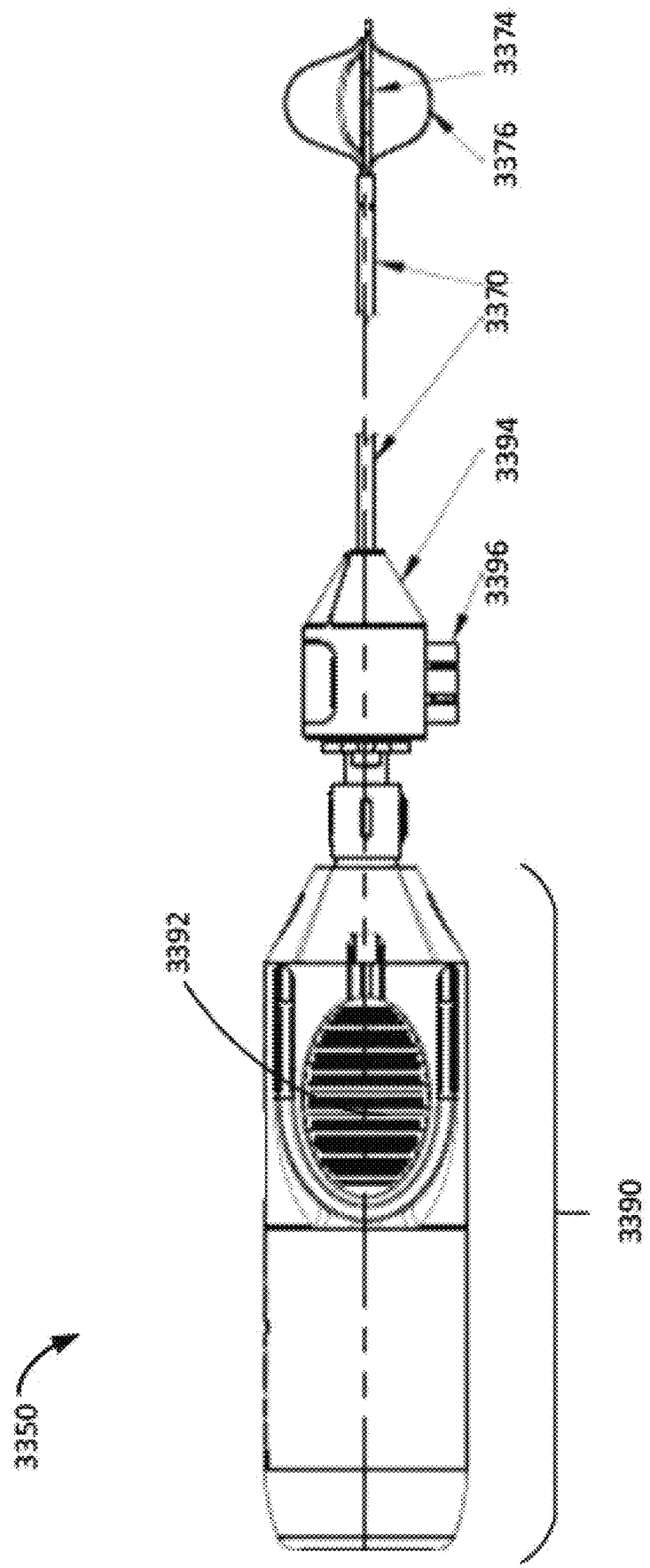
FIG. 36 is an illustration of an ablation catheter, according to an embodiment.

FIG. 36 provides a more detailed view of an ablation catheter 3350 of an ablation system, according to an embodiment. As shown, the ablation catheter 3350 includes an inner shaft 3370, a nozzle 3374, an expandable structure 3376 (e.g., expandable cage), an inner shaft handle 3390 with an inner shaft handle button 3392, a wire termination collar 3394, and an inner shaft plug 3396. In some embodiments, the inner shaft 3370, the nozzle 3374, the expandable structure 3376, the inner shaft handle 3390, and the inner shaft handle button 3392, the wire termination collar 3394, and the inner shaft plug 3396 can be the same or substantially similar to the inner shaft 3170, the nozzle 3174, the expandable structure 3176, the inner shaft handle 3190, the inner shaft handle button 3192, the wire termination collar 3194, and the inner shaft plug 3196, as described above with reference to FIGS. 34A-34B. Thus, certain aspects of the inner shaft 3370, the nozzle 3374, the expandable structure 3376, the inner shaft handle 3390, the inner shaft handle button 3392, the wire termination collar 3394, and the inner shaft plug 3396 are not described in greater detail herein.

In some embodiments, the distal end of the ablation catheter 3350 can be inserted through a lumen of an outer shaft or introducer, e.g., as depicted in FIG. 34A. For illustrative purposes in FIG. 36, the inner shaft 3370 is shown with a discontinuity to indicate that a length of the inner shaft is longer than that shown in FIG. 36. The expandable structure 3376 can be transitioned between an undeployed configuration and a deployed configuration. When the expandable structure 3376 is in the undeployed configuration, the expandable structure 3376 can have elongate members that extend substantially parallel to a longitudinal axis of the catheter 3350 and, in particular, a longitudinal axis of the shaft 3370. In such configuration, the distal portion of the shaft 3370 (including the nozzle 3374 and the expandable structure 3376) can be inserted through a lumen of an outer shaft or introducer, e.g., into a gallbladder lumen. After the distal portion of the shaft 3370 has been inserted past a distal end of the outer shaft, then the expandable structure 3376 can be transitioned into the deployed configuration, where the elongate members of the expandable structure 3376 extend outward (e.g. bow out radially) from the longitudinal axis.

Figure 37A:
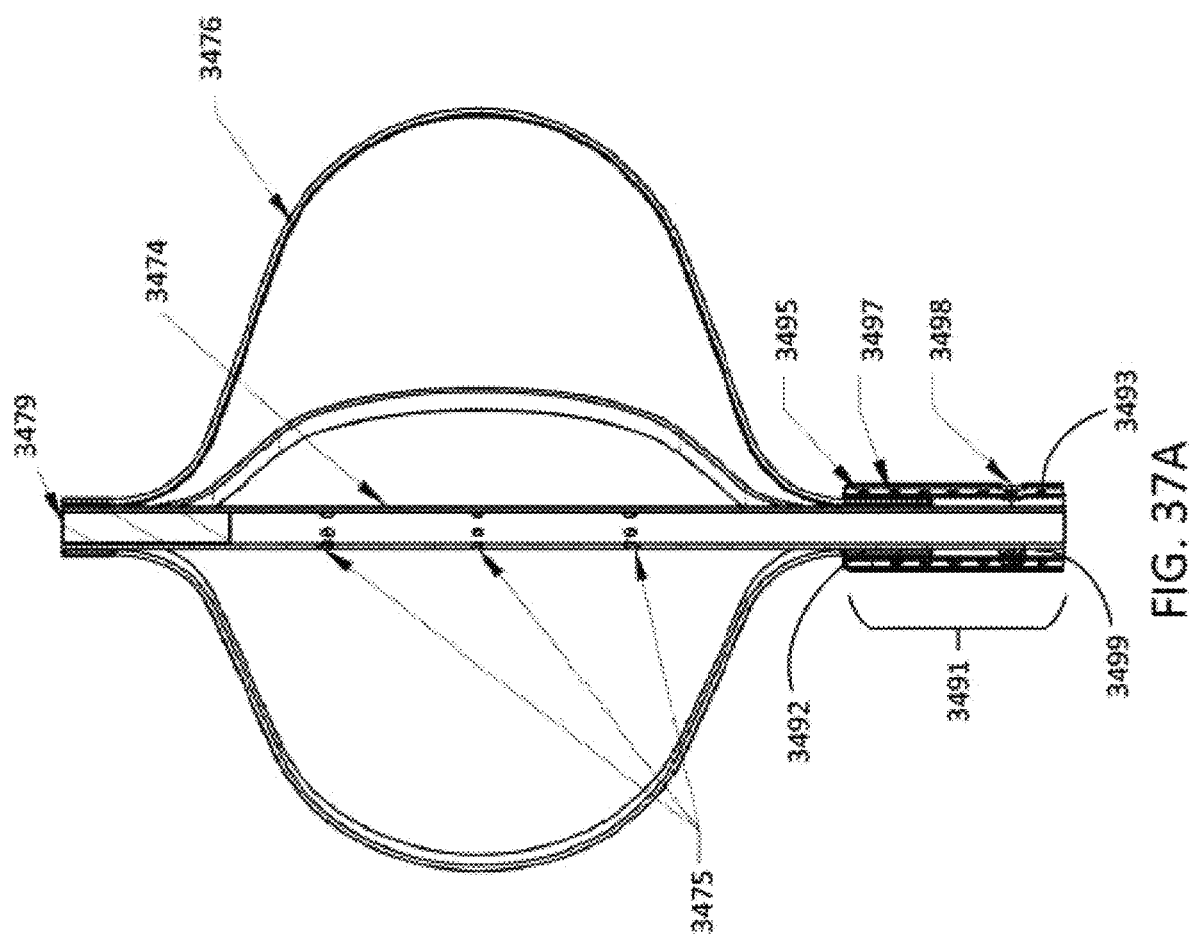

FIGS. 37A-37B are detailed viewed of a distal portion of an ablation catheter with heating elements, according to an embodiment. FIG. 37A shows a cross-sectional view of the distal portion, with portions of the interior shown, while FIG. 37B is an exterior view of the distal portion. As shown, the distal portion of the ablation catheter includes a nozzle 3474 including a plurality of nozzle openings or fenestrations 3475, an expandable structure 3476 (e.g., expandable cage), a hub 3479, and a heated sheath 3491. The heated sheath 3491 includes a jacket 3492, a liner 3493, a sensor wire or lead implemented as a thermocouple wire 3495, a heating element implemented as a heating wire 3497, and vent openings or holes 3498. In some embodiments, the fenestrations 3475 can be the same or substantially similar to the fenestrations 1175, as described above with reference to FIG. 11, or other nozzle openings described herein. In some embodiments, the expandable structure 3476 can be the same or substantially similar to other expandable structures described herein, including, for example, expandable structure 876, as described above with reference to FIG. 9, and/or expandable structure 3176, as described above with reference to FIG. 34A. Thus, certain aspects of the fenestrations 3475 and the expandable structure 3476 are not described in greater detail herein.

The expandable structure 3476 can be formed of a plurality of elongate members. The plurality of elongate members are transitionable between an undeployed configuration in which the elongate members extend substantially parallel to a longitudinal axis of the catheter and a deployed configuration in which the elongate members extend outward (e.g., bow out radially) from the longitudinal axis. In some embodiments, each of the elongate members can have a proximal end that is coupled to a distal end of the heated sheath 3491 and a distal end that is coupled to a hub 3479. In such embodiments, deployment of the elongate members can be made by moving the hub 3479 or the heated sheath 3491 relative to the other of the hub 3479 and the heated sheath 3491. For example, the heated sheath 3491 can be advanced distally toward the hub to cause the elongate members to extend outward (e.g., bow out radially) and to deploy the expandable structure 3476.

The jacket 3492 and the liner 3493 of the heated sheath 3491 insulate the thermocouple wire 3495 and the heating wire 3497. In some embodiments, the jacket 3492 and/or the liner 3493 can be extruded over the wires 3495, 3497. The jacket 3492 is positioned exterior to the thermocouple wire 3495 and the heating wire 3497, while the liner 3493 is positioned interior to the thermocouple wire 3495 and the heating wire 3497. In some embodiments, the thermocouple wire 3495 and the heating wire 3497 can be wound together. In some embodiments, the thermocouple wire 3495 can be laid straight under the heating wire 3497.

The vent holes 3498 are configured to communicatively couple a pressure sensing lumen 3499 with an exterior of the catheter. As such, the vent holes 3498 can be configured to couple the pressure sensing lumen 3499 with a lumen of a gallbladder such that an intraluminal pressure of the gallbladder can be measured via the pressure sensing lumen 3499. The pressure sensing lumen 3499 can be an annular space that is disposed between an inner shaft defining a lumen for delivering the ablation medium and the heated sheath 3491. As shown, the catheter includes two vent holes 3498. Inclusion of multiple vent holes 3498 can allow the maintain coupling between the pressure sensing lumen 3499 and a body lumen when one of the vent holes is clogged. In some embodiments, the catheter can include 3, 4, 5, 6, 7, 8, 9, 10, or more than about 10 vent holes 3498.

The thermocouple wire 3495 can be configured to couple a temperature sensor (e.g., thermocouple) with a control unit or processor (e.g., control unit 110) at a proximal end of the ablation catheter (or operatively coupled to a proximal end of the ablation catheter). The temperature sensor can be disposed near the vent holes 3498 and/or outside of the ablation catheter to measure a temperature near the distal portion of the ablation catheter.

Figure 38A:
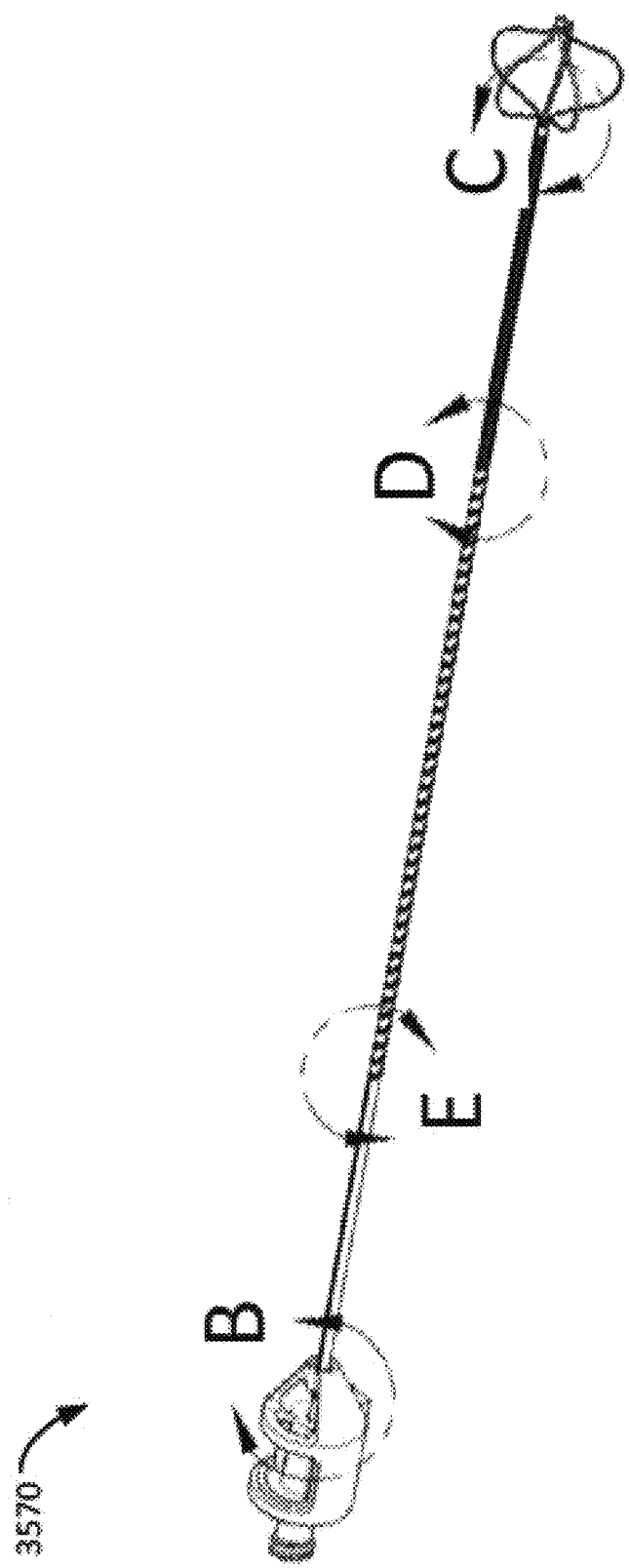
FIGS. 38A-38E are illustrations of a catheter assembly, according to an embodiment.
Figure 38B:
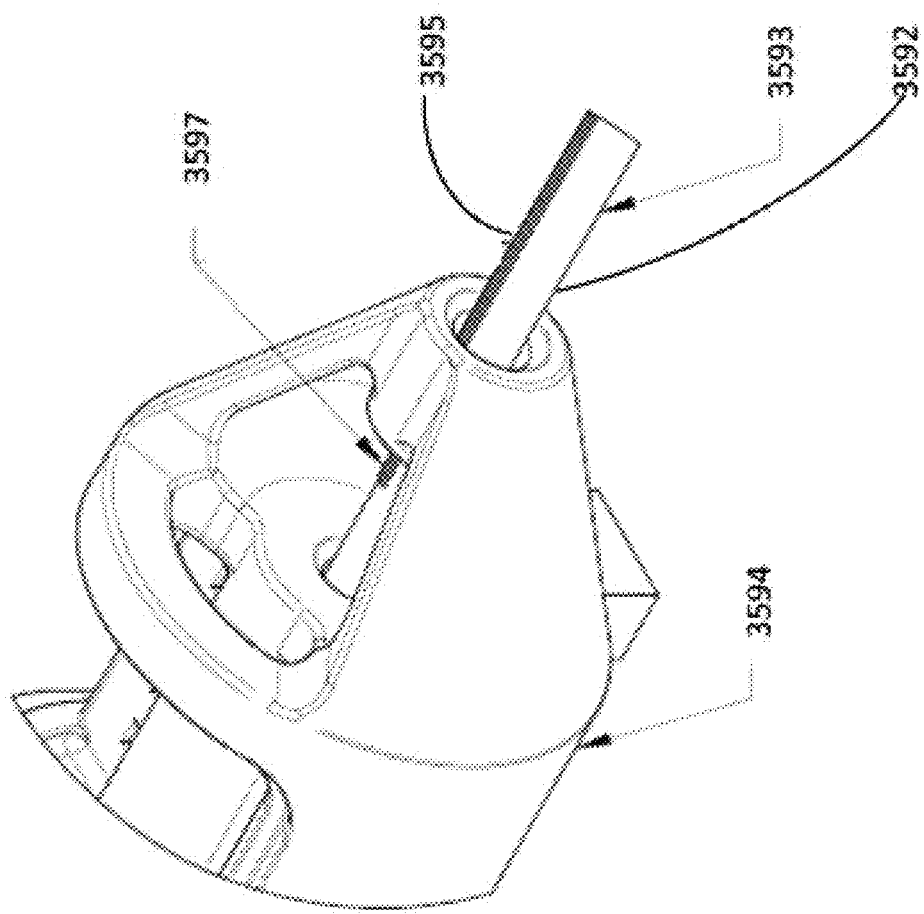
Figure 38C:
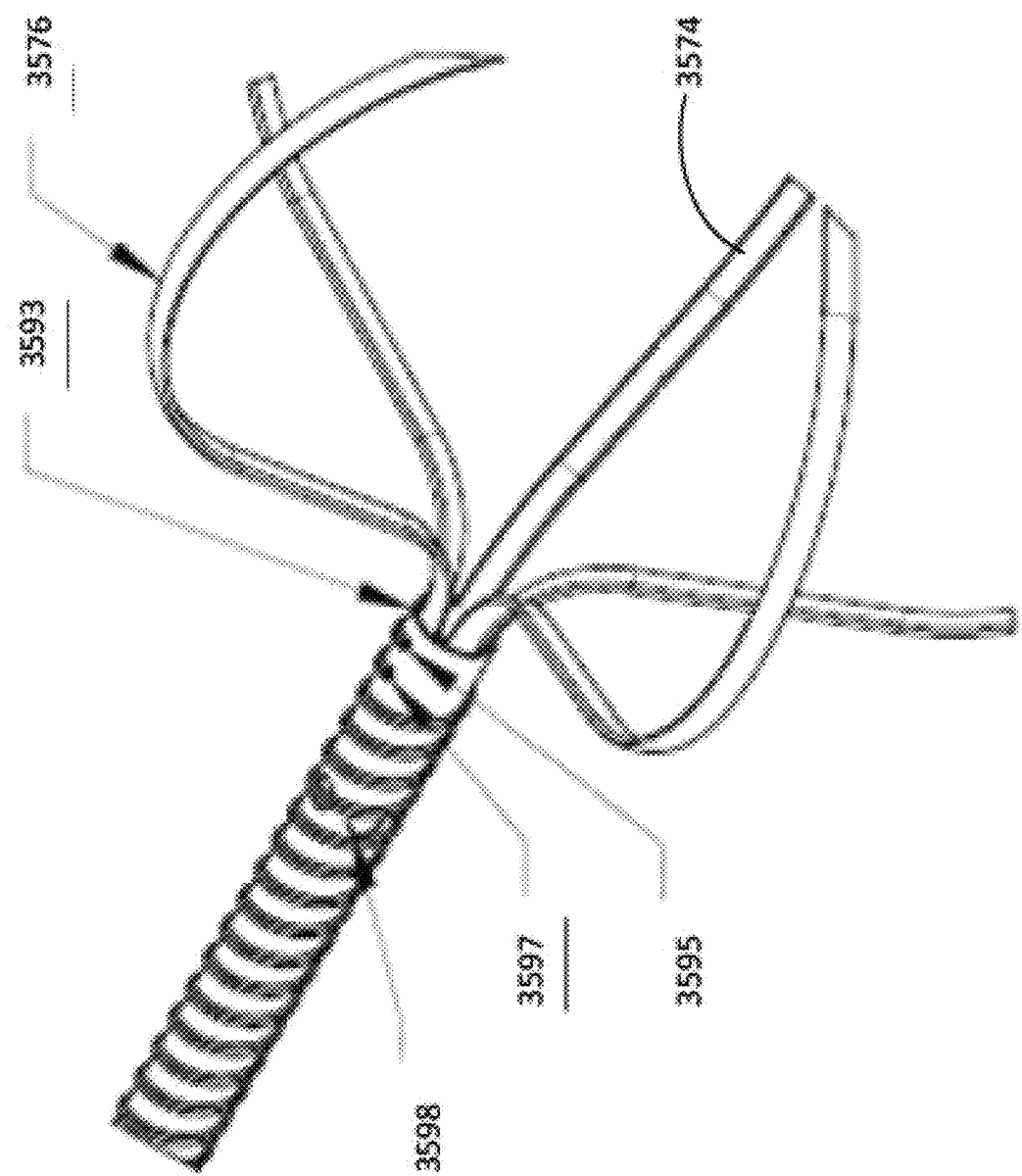
Figure 38D:
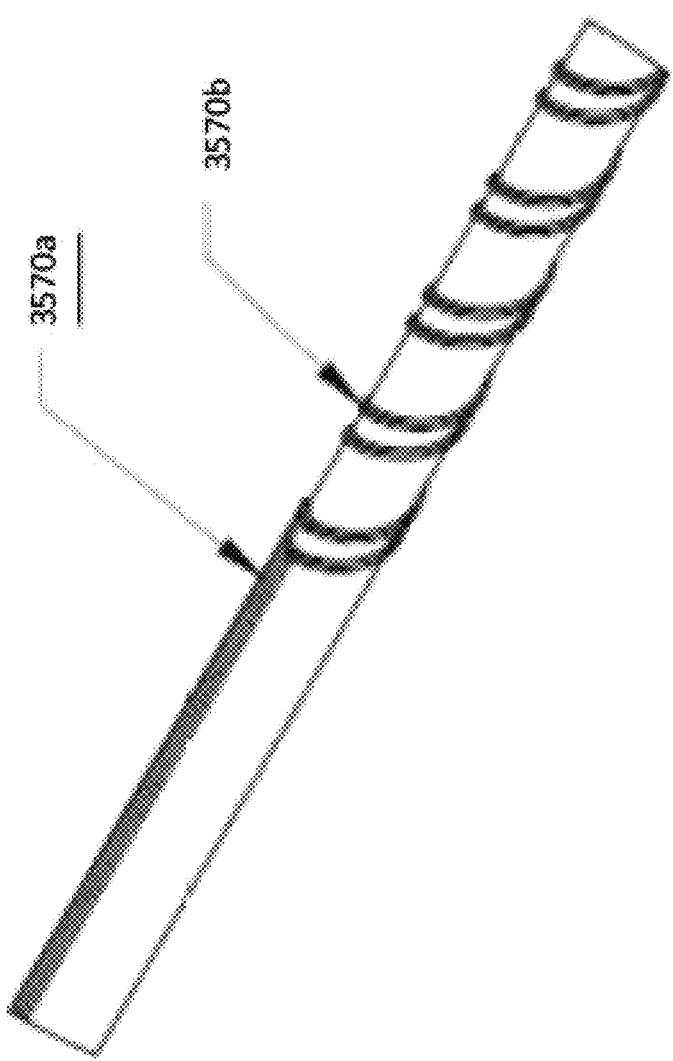
Figure 38E:
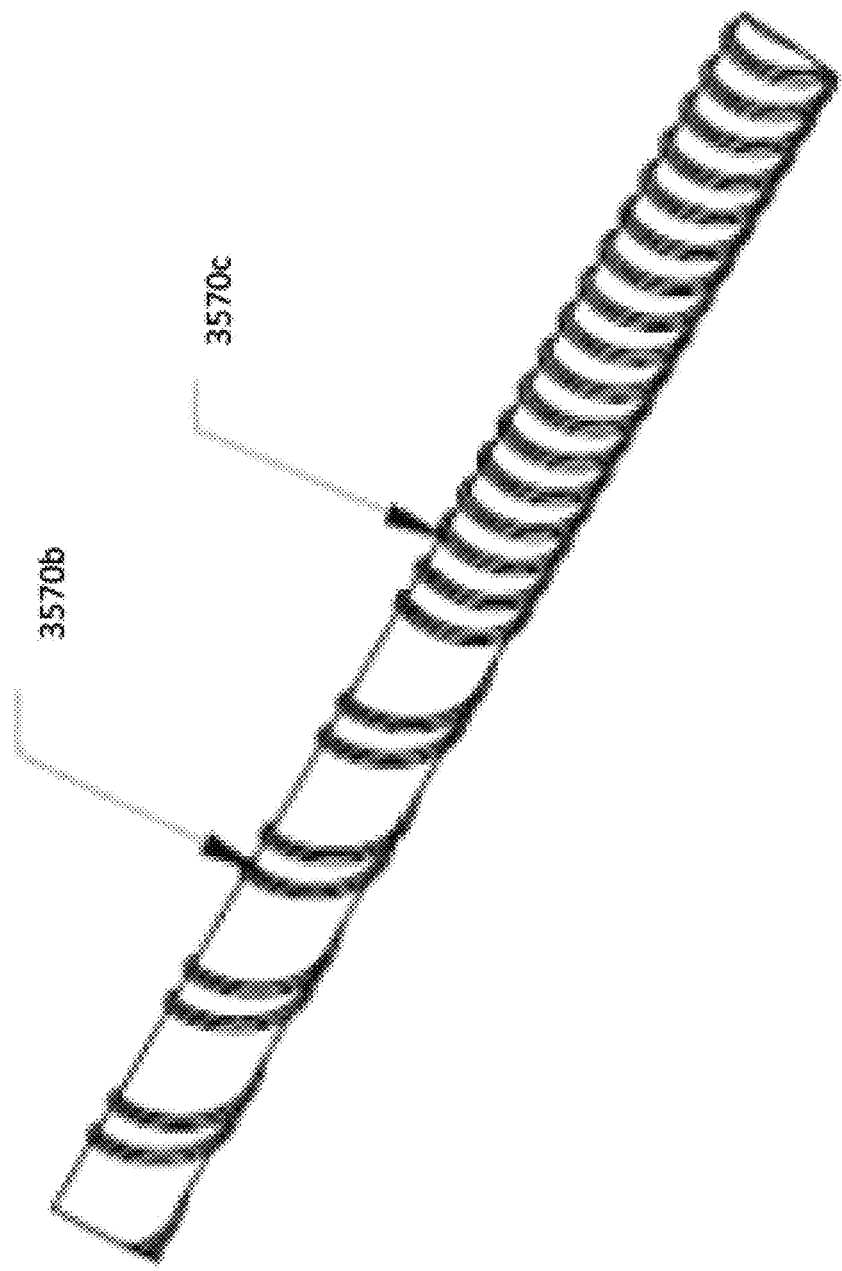

FIGS. 38A-38E show an ablation catheter assembly 3570, and details thereof, according to an embodiment. FIG. 38A shows the full catheter assembly 3570, while FIG. 38B shows details of section B, as marked in FIG. 38A, FIG. 38C shows details of section C, as marked in FIG. 38A, FIG. 38D shows details of section D, as marked in FIG. 38A, and FIG. 38E shows details of section E, as marked in FIG. 38E. As shown, the catheter assembly 3570 includes a nozzle 3574, an expanded structure 3576, a jacket 3592, a liner 3593, a wire termination collar 3594, a thermocouple wire 3595, a heating wire 3597, and vent holes 3598. In some embodiments, the nozzle 3574, the expanded structure 3576, the jacket 3591, the liner 3593, the thermocouple wire 3595, the heating wire 3597, the wire termination collar 3594, and the vent holes 3598 can be the same or substantially similar to like components described in other embodiments herein, including, for example, the nozzle 3174, the expandable structure 3176, the wire termination collar 3194, and the inner shaft plug 3196, as described above with reference to FIGS. 34A-34B and/or the nozzle 3474, the expanded structure 3476, the jacket 3492, the liner 3493, the thermocouple wire 3495, the heating wire 3497, and the vent holes 3498, as described above with reference to FIGS. 37A-37B. Thus, certain aspects of the nozzle 3574, the expanded structure 3576, the jacket 3591, the liner 3593, the wire termination collar 3594, the thermocouple wire 3595, the heating wire 3597, and the vent holes 3598 are not described in greater detail herein. The heating wire 3597 and/or thermocouple wire 3595 can be wound around portions of the sheath, the shaft, and/or an annular space between the sheath and the shaft to heat those portions.

In some embodiments, the thermocouple wire 3595 and/or the heating wire 3597 can couple to one or more connections in the wire termination collar 3595. For example, the thermocouple wire 3595 can be configured to couple via the collar 3595 to an external processor or control unit (e.g., control unit 110), e.g., for monitoring temperature, pressure, and/or other conditions and/or controlling the delivery and/or evacuation of the ablation medium. The heating wire 3597 can be configured to couple to an external heat source via the collar 3595, e.g., for receiving energy from the external heat source and to generate heat for heating portions of the ablation catheter. In some embodiments, the wire termination collar 3595 can be coupled to a proximal handle for operating the ablation catheter, as described with reference to FIG. 34A. In some embodiments, the collar 3595 can be omitted, and the thermocouple wire 3595 and/or the heating wire 3597 can be configured to couple to the handle (including any onboard components, such as, for example, an onboard processor and/or microcontroller, a power source, etc.).

As shown in FIGS. 38D and 38E, the thermocouple wire 3595 and the heating wire 3597 are divided into a straight section 3570a, a coarse wound section 3570b, and a finely wound section 3570c. A tighter pitch of the heating wire 3597 (i.e., a finer wound heating wire) can increase the energy density of a particular region. In some embodiments, the finely wound section 3570c can have a length of about 0.5 cm, about 1 cm, about 1.5 cm, about 2 cm, about 2.5 cm, about 3 cm, about 3.5 cm, about 4 cm, about 4.5 cm, or about 5 cm, inclusive of all values and ranges therebetween. In some embodiments, the finely wound section 3570c can cover about 5%, about 10%, about 15%, about 20%, about 25%, or about 30% of the full length of the full catheter assembly 3570, inclusive of all values and ranges therebetween. In some embodiments, the transition from the coarse wound section 3570b to the finely wound section 3570c can be gradual, or the spacing between the thermocouple wire 3595 and the heating wire 3597 can change as a gradient. In some embodiments, the transition from the coarse wound section 3570b to the finely wound section 3570c can be immediate.

In some embodiments, adjacent turns of the wires can be spaced apart in the coarse wound section by about 0.5 mm, about 1 mm, about 1.5 mm, about 2 mm, about 2.5 mm, about 3 mm, about 3.5 mm, about 4 mm, about 4.5 mm, or about 5 mm, inclusive of all values and ranges therebetween. In some embodiments, the wires can be spaced apart in the finely wound section 3570c by about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm, inclusive of all values and ranges therebetween.

Power delivered to the thermocouple wire 3595 and the heating wire 3597 can be a function of operating voltage and wire resistance. Operating voltage and wire resistance can be tuned to achieve a desired energy density through the cross-sectional area of the heating wire, thus determining the thermal flux generated by the heating wire 3597 and the temperature response to cooling.

While a single heating element is depicted in FIGS. 38A-38A, it can be appreciated that any number of heating elements can be used. For example, multiple heating wires that extend along different portions of the ablation catheter (e.g., different portions of a sheath, a shaft, or annular space therebetween). In some embodiments, multiple heating wires can be selectively activated, e.g., using a processor (e.g., control unit 110), to maintain substantially uniform temperature along an entire length of the sheath, the shaft, or the annular space therebetween. Substantially uniform temperature can be, for example, temperatures along the entire length that do not deviate more than 10% from an average or median temperature. In some embodiments, one or more sensors (e.g., coupled to thermocouple wires) can be disposed at one or more locations along the length of the shaft and used to measure temperatures at different points along the length of the shaft. These measured temperatures can be received at the processor and used to control the one or more heating elements (e.g., selectively activate or adjust amount of power being delivered to the heating elements).

Figure 39:
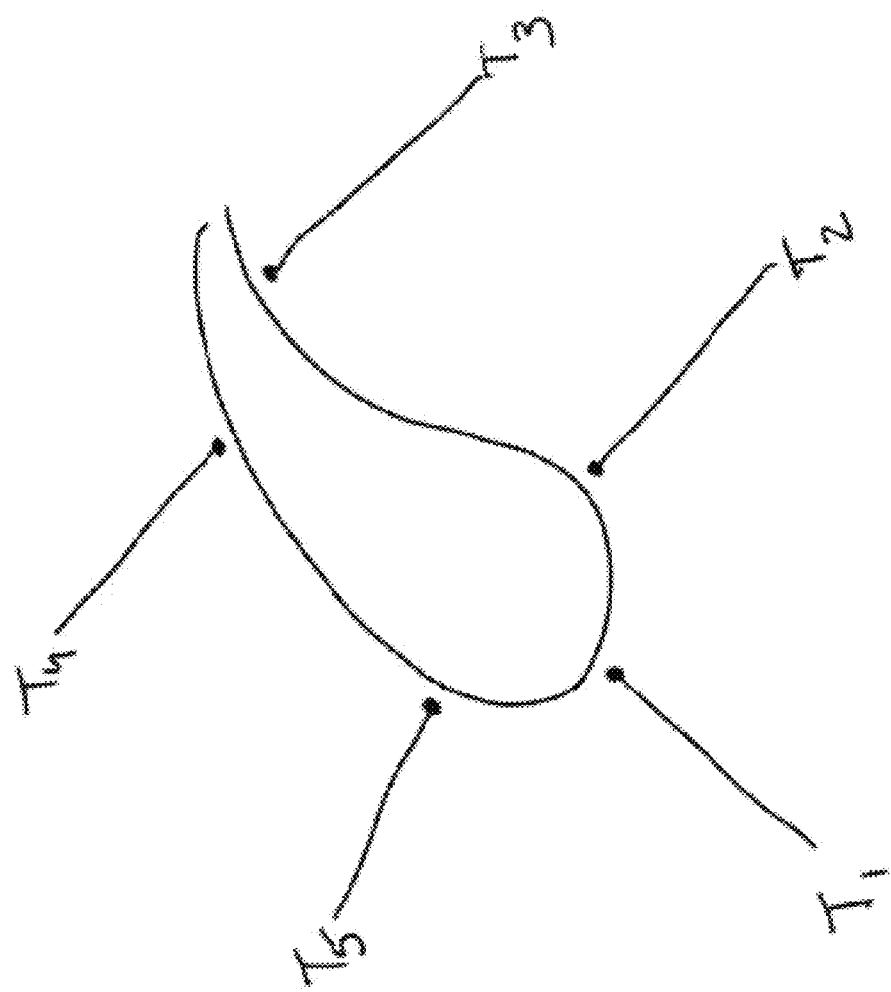
FIG. 39 is a depiction of temperature sensor placement locations in the gallbladder, according to an embodiment.

In some embodiments, the thermocouple wire 3595 can be coupled to a temperature sensor disposed near a distal end of the ablation catheter. The thermocouple wire 3595 can carry the temperature signal to a processor (e.g., an onboard processor and/or external processor) for monitoring of temperature and/or control of ablation delivery and/or evacuation based on temperature. In some embodiments, ablation devices and/or systems described herein can be used with external temperature probes. FIG. 39 is a depiction of placement of temperature sensors (e.g., probes or needle-like temperature sensors) throughout a length of a gallbladder, according to an embodiment. As shown, the gallbladder includes a neck region, a body region, and a fundus region. Temperature probes can be placed outside of the wall of the gallbladder to monitor how temperature changes along the length of the gallbladder, e.g., from neck through fundus. The placement of temperature probes can confirm that temperature changes have pervaded from the inside to the outside of the gallbladder, which can facilitate determination of the efficacy of the ablation. In other words, the temperature probes can also aid in confirming that cryoablation has occurred, i.e., the gallbladder wall has been ablated. In some embodiments, a first temperature probe T1 can be placed at a distal end of the gallbladder. Measuring the temperature at the fundus end of the gallbladder can confirm that the cryoablation medium has penetrated to that end of the gallbladder. In some embodiments, a temperature probe can be placed at a point between the fundus end and the neck of the gallbladder (e.g., temperature probe T2). In some embodiments, a temperature probe can be placed in the neck region near the opening of the gallbladder into the cystic duct (e.g., temperature probe T3). In some embodiments, an additional temperature probe can be placed in the neck region of the gallbladder (e.g., temperature probe T4). In some embodiments, an additional temperature probe can be placed at a point between the fundus and the neck of the gallbladder (e.g., temperature probe T5). In some embodiments, a combination of at least three temperature sensors (e.g., one placed at neck, one placed at body, one placed at fundus) can be used to measure the temperature of the tissue wall along a length of the gallbladder. In some embodiments, depending on the temperature measurements, a location of the nozzles of the ablation catheter can be adjusted, e.g., translated distally and/or proximally to target regions of tissue having higher temperatures. As such, the placement of the temperature probes can be used to confirm even distribution of ablation medium within the gallbladder and/or provide feedback for controlling further delivery of ablation medium.

Figure 40A:
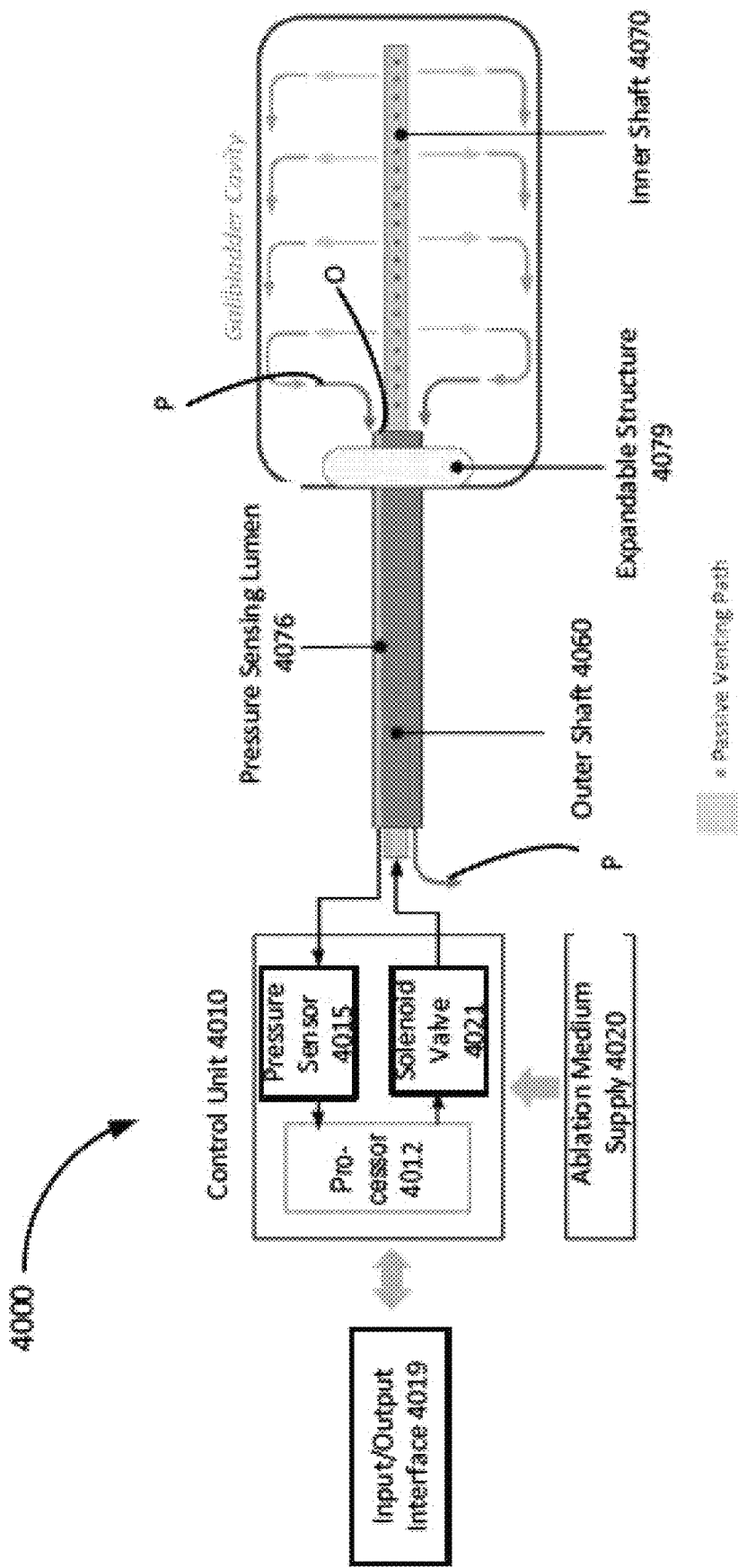
FIGS. 40A-40D are illustrations of an ablation system (e.g., cryoablation device) with a pressure sensor, according to various embodiments.
Figure 40D:
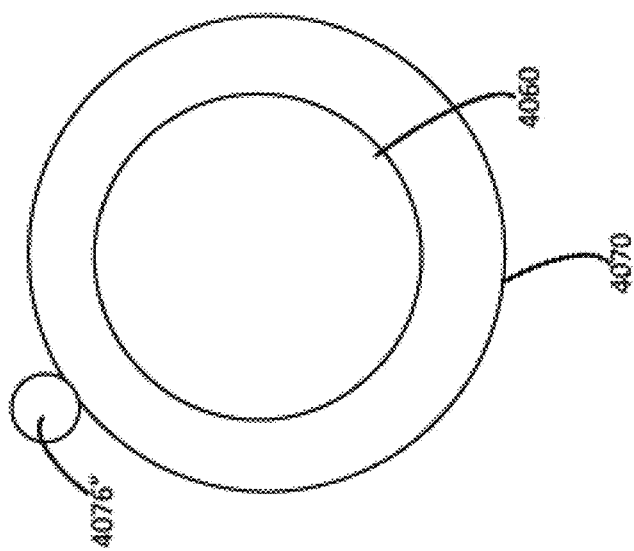
Figure 40C:
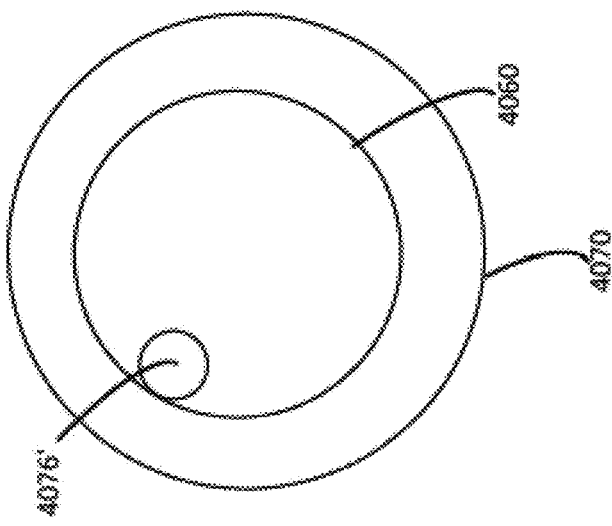
Figure 40B:
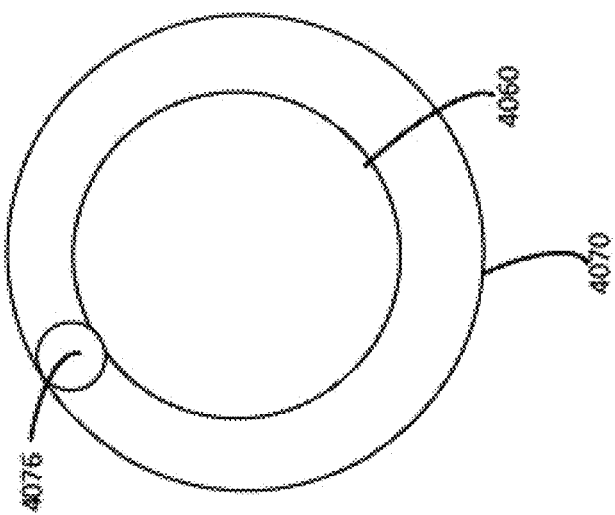

FIGS. 40A-40D are illustrations of ablation system implemented as a cryoablation device 4000. The cryoablation device 4000 can be configured to ablate or defunctionalize a gallbladder cavity. The cryoablation device 4000 can include components that are structurally and/or functionally similar to other ablation systems and components thereof described herein. FIG. 40A shows a side profile view of the cryoablation device 4000, while FIGS. 40B-40D show cross sectional views of various configurations of lumens of inner and outer shafts of the cryoablation device 4000. The cryoablation device 4000 includes a control unit 4010, an outer shaft 4060, an inner shaft 4070, and a pressure sensing lumen 4076. The control unit 4010 includes a processor 4012, a pressure sensor 4015, an input/output interface 4019, and a solenoid valve 4021. In some embodiments, an expandable structure 4079 can hold the inner shaft 4070 in the gallbladder cavity during deployment of an ablation medium. The control unit 4010 is fluidically coupled to an ablation medium supply 4020. In some embodiments, ablation medium can flow from the ablation medium supply to the inner shaft 4070, passing by the solenoid valve 4021.

In some embodiments, the pressure sensing lumen 4076 can terminate at an orifice O that is disposed in the gallbladder cavity, while the pressure sensor 4015 is located outside of the gallbladder cavity. In other words, the pressure sensing lumen 4076 can fluidically couple an interior of the gallbladder cavity to the pressure sensor 4015. The pressure sensor 4015 can be disposed at the control unit 4010 and/or operatively coupled to the control unit 4010. In such a configuration, the pressure sensor 4015 can measure the pressure inside of the gallbladder cavity while being positioned outside of the gallbladder cavity.

The pressure sensing lumen 4076 can be disposed about the inner shaft 4070 or outer shaft 4060 of the catheter system according to one of several different arrangements. In some embodiments, the pressure sensing lumen 4076 can have a circular cross-section and be disposed to one side of a shaft. For example, in an embodiment, the pressure sensing lumen 4076 can be affixed to the inner shaft 4070, as shown in FIG. 40B. Alternatively, a pressure sensing lumen 4076' can be disposed or defined within the inner shaft 4070, as shown in FIG. 40C. As yet another alternative, a pressure sensing lumen 4076" can be disposed outside the outer shaft 4060, as shown in FIG. 40D. As additional alternatives, a pressure sensing lumen can be integrated into a wall of the inner or outer shaft, coupled to both inner and outer shafts, etc. In some embodiments, a pressure sensing lumen 4076 can be an annular space that is formed between outer and inner concentric sheaths and/or shafts of the inner shaft 4070, such as described with reference to FIG. 37A. Pressure can be relieved from the gallbladder cavity via venting paths P that pass through the outer shaft 4060 and to the outside of the cryoablation device 4000. The pressure sensing lumen may also be referred to as a pressure lumen or a sensor lumen.

While not expressly identified in FIGS. 40A-40D, the cryoablation device 4000 includes a lumen defined by inner and outer shafts 4060, 4070 for delivery of an ablation medium and/or evacuation of an ablation medium from the gallbladder cavity. For example, similar to other catheter systems described herein, the inner shaft 4070 can define a lumen for delivery of a cryogenic ablation medium to the gallbladder cavity, e.g., via one or more nozzle openings. The outer shaft 4060 can define a for evacuating the cryogenic ablation medium from the gallbladder cavity.

Systems, devices, and methods described herein can implement a passive evacuation channel and cryogen control system to safely vent cryogen gas from the gallbladder cavity, while ensuring safe operating conditions. During cryogen delivery, a cryogenic ablation medium (e.g., nitrous oxide) expands and evacuates to an external environment (e.g., atmosphere) through an annular space between an inside surface of the outer shaft 4060 and an outer surface of the inner shaft 4070. Resistance in the evacuation channel can cause the gallbladder cavity to distend, to facilitate exposure of tissue within the lumen to the cryogenic ablation medium. The solenoid valve 4021 can be configured to control or regulate delivery of the ablation medium, e.g., from the ablation medium supply 4020, into the gallbladder lumen. For example, the control unit 4010 can control the solenoid valve 4021 to transition from an open state in which ablation medium can be delivered into the gallbladder lumen to a closed state in which ablation medium can be prevented from being delivered into the gallbladder lumen. While a solenoid valve is provided as the example valve herein, it can be appreciated that other types of valves, including mechanically actuated valves, magnetically actuated valves, etc. can be used to control the delivery of the ablation medium into the gallbladder lumen. The control unit 4010, pressure sensor 4015, and solenoid valve 4021 can produce a closed-loop pressure feedback system for maintaining safe operating pressures within the gallbladder cavity. In particular, in response to detecting a pressure within the gallbladder cavity that is greater than a predetermined maximum threshold, the control unit 4010 can control the solenoid valve 4021 to terminate supply of the ablation medium into the gallbladder cavity and/or evacuate via the outer shaft 4060 the ablation medium from the gallbladder cavity to an external environment. Additionally or alternatively, in response to detecting a pressure within the gallbladder cavity that is less than a predetermined minimum threshold, the control unit 4010 can control the ablation medium supply 4020 and/or solenoid valve 4021 to provide additional ablation medium into the gallbladder cavity to sufficiently distend the gallbladder for cryoablation.

It will be appreciated that the present disclosure may include any one and up to all of the following examples.

Example 1: A cryoablation catheter, comprising: a catheter body including at least one cryogen delivery lumen for delivery of a cryogen to an area of tissue; and a nozzle disposed at a distal end of the at least one cryogen delivery lumen, the nozzle including a plurality of orifices extending between the at least one cryogen deliver lumen an outer surface of the nozzle, and individual orifices of the plurality of orifices being sized and shaped to uniformly disperse the cryogen onto the area of tissue with a constant mass flow rate through each of the plurality of orifices.

Example 2: The cryoablation catheter of Example 1, wherein the cryogen includes nitrous oxide.

Example 3: The cryoablation catheter of Example 1, wherein the nozzle further includes a phase-change interface at an intersection of the plurality of orifices and the outer surface of the nozzle.

Example 4: The cryoablation catheter of Example 3, wherein the plurality of orifices are sized and shaped such that the cryogen remains a liquid until the cryogen reaches the phase-change interface.

Example 5: The cryoablation catheter of Example 3, wherein a diameter of each of the plurality of orifices sized in the range of about 0.0005 inches to 0.004 inches.

Example 6: The cryoablation catheter of Example 3, wherein a phase change of the cryogen occurs with the cryogen is exposed to a near atmospheric pressure associated with a target ablation area.

Example 7: The cryoablation catheter of Example 3, wherein the phase-change interface is controlled by a pressure drop relative to a supply pressure of the cryogen.

Example 8: The cryoablation catheter of Example 1, wherein a nozzle geometry of the nozzle is one of a sphere, a cube, a cone, a cylinder, a triangular prism, a torus, a helix, or an ovoid.

Example 9: The cryoablation catheter of Example 1, wherein the nozzle geometry is a sphere, and the plurality of orifices are disposed along a spherical body of the nozzle, each orifice of the plurality of orifices extending from an outer diameter of the spherical body to the at least one cryogen delivery lumen.

Example 10: The cryoablation catheter of Example 1, wherein the nozzle is sized to allow the nozzle to slide through an access catheter.

Example 11: The cryoablation catheter of Example 1, wherein the nozzle is inflatable.

Example 12: The cryoablation catheter of Example 1, wherein the nozzle includes a linear rail component and a nozzle geometry, the nozzle geometry being coupled to the linear rail component, and the plurality of orifices being disposed along an outer surface of the nozzle geometry.

Example 13: The cryoablation catheter of Example 12, the linear rail component can facilitate at least one of concentric movement or non-concentric movement of the nozzle geometry between about 0-10 cm in response to a driving force Example 14: The cryoablation catheter of Example 12, wherein a nozzle geometry of the nozzle includes one of a sphere, a cube, a cone, a cylinder, a triangular prism, a torus, a helix, or an ovoid.

Example 15: The cryoablation catheter of Example 12, wherein the nozzle geometry includes a sphere, and the plurality of orifices are disposed along a spherical body of the nozzle, each orifice of the plurality of orifices extending from an outer diameter of the spherical body to the at least one cryogen delivery lumen.

Example 16: The cryoablation catheter of Example 12, wherein the nozzle geometry is fixed relative to a distal end of the linear rail component.

Example 17: The cryoablation catheter of Example 12, wherein the nozzle geometry is moveable in response to displacement of the linear rail component by a driving force.

Example 18: The cryoablation catheter of Example 12, wherein the nozzle geometry is moveable along at least one axis of the linear rail component.

Example 19: The cryoablation catheter of Example 12, wherein the nozzle geometry is moveable along the linear rail component in response to a driving force.

Example 20. The cryoablation catheter of Example 19, wherein the driving force is automated, and further comprising a control unit, the control unit being configured to initiate the driving force.

Example 21: The cryoablation catheter of Example 19, wherein the driving force is caused by at least one of: a stiff drive wire system, a flexible drive cable system, a mating gear drive system, a rack-and-pinion system, a screw-drive mechanism, a pneumatic actuator system, an electromagnetic coil system, a hydraulic actuator system, or an electromechanical system.

Example 22: The cryoablation catheter of Example 12, wherein the linear rail component is fixed by at least one of: a proximal component of the linear rail component or a distal component of the linear rail component.

Example 23: The cryoablation catheter of Example 1, wherein respective diameters of individual orifices of the plurality of orifices in the nozzle vary from one another based at least in part on a location of the individual orifices on the nozzle.

Example 24: The cryoablation catheter of Example 1, wherein a diameter along a length of individual orifices of the plurality of orifices tapers.

Example 25: The cryoablation catheter of Example 1, wherein at least a subset of orifices are shaped and sized to target close targets.

Example 26: The cryoablation catheter of Example 1, wherein at least a subset of orifices are shaped and sized to target distant targets.

Example 27: The cryoablation catheter of Example 1, wherein the nozzle includes a bowed segment.

Example 28: The cryoablation catheter of Example 27, wherein at least one of the plurality of orifices are disposed along the bowed segment.

Example 29: The cryoablation catheter of Example 27, wherein the bowed segment is rotatable around its central axis.

Example 30: The cryoablation catheter of Example 27, wherein the bowed segment is moveable longitudinally relative to its central axis.

Example 31: The cryoablation catheter of Example 1, wherein the nozzle includes a spiral nozzle, the plurality of orifices being disposed along a spiral nozzle lumen of the spiral nozzle and extending from the at least one cryogen delivery lumen to an outer surface of the spiral nozzle lumen.

Example 32: The cryoablation catheter of Example 31, further comprising a spiral body structure, the spiral nozzle lumen being mounted on the spiral body structure.

Example 33: The cryoablation catheter of Example 1, wherein the nozzle is collapsible.

Example 34: The cryoablation catheter of Example 1, wherein the nozzle includes at least one nozzle branch with a plurality of orifices to deliver the cryogen.

Example 35: The cryoablation catheter of Example 34, wherein the at least one branch forms a bowed shape along a central axis that extends to a maximum radial dimension and converges back towards the central axis to help bring the nozzle holes closer to the target ablation site.

Example 36: The cryoablation catheter of Example 34, wherein at least one branch at least one branch forms a bowed shape along a central axis that extends to a maximum radial dimension and terminates to help bring the nozzle holes closer to the target ablation site.

Example 37: The cryoablation catheter of Example 34, wherein the nozzle is spring loaded and can collapse to be delivered through a smaller diameter delivery lumen, relative to the nominal expanded diameter of the at least one branch.

Example 38: The cryoablation catheter of Example 34, wherein the nozzle is constructed with a pre-shaped core within the nozzle branches and exerts a return force when subjected to mechanical stress, thermal energy, electrical current, or light Example 39: The cryoablation catheter of Example 38, wherein the pre-shaped core is made from an alloy metal.

Example 40: The cryoablation catheter of Example 38, wherein the pre-shaped core is made from a polymer.

Example 41: The cryoablation catheter of Example 34, the nozzle can be driven to an expanded conformation by a mechanical driving force, such as a rack and pinion gear system, a cable drive system, or electromechanical control system.

Example 42: The cryoablation catheter of Example 1, wherein the nozzle can be actuated along a linear or radial pathway to increase distribution of cryogen from the at least one nozzle branch.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Also, various concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The invention claimed is:

1. An apparatus, comprising:
   a handle including an actuation mechanism;
   a first shaft extending from the handle and defining a first lumen, the first shaft having a distal portion that is disposable within a gallbladder lumen;
   a second shaft disposable within the first lumen and defining a second lumen, the second shaft having a distal portion that is configured to extend out of the distal end of the first shaft and be disposed within the gallbladder lumen;
   an expandable body disposed on the distal portion of the first shaft, the expandable body configured to transition from an undeployed configuration to a deployed configuration in response to an actuation of the actuation mechanism, the expandable body formed of a plurality of elongate members that are configured to extend substantially parallel to the first shaft in the undeployed configuration and to bow radially outward from the first shaft in the deployed configuration;
   a plurality of nozzle openings formed on the distal portion of the first shaft between the ends of the expandable body, the plurality of nozzle openings being in communication with the first lumen such that the first lumen and the plurality of nozzle openings are configured to deliver a cryogenic ablation medium into the gallbladder lumen; and
   a temperature sensor disposed on the distal portion of the first shaft, the temperature sensor configured to measure a temperature within the gallbladder lumen, the temperature sensor being coupled to a wire that extends along the first shaft to the handle;
   a pressure sensing lumen disposed in the second shaft and configured to terminate in the gallbladder lumen; and
   a pressure sensor configured to be disposed outside of the gallbladder lumen, the pressure sensor being fluidically coupled to the pressure sensing lumen and configured to measure a pressure of the gallbladder lumen,
   the first shaft with the expandable body in the undeployed configuration configured to be extended through an access path and into the gallbladder lumen,
   the first shaft with the expandable body in the deployed configuration configured to position the plurality of nozzle openings at a minimum radial distance from a wall of the gallbladder such that the cryogenic ablation medium being delivered via the plurality of nozzle openings can distribute within the gallbladder lumen before contacting and ablating the wall of the gallbladder lumen.

2. The apparatus of claim 1, wherein the nozzle is movable relative to the expandable body.

3. The apparatus of claim 2, wherein the plurality of nozzle openings is rotatable relative to the expandable body.

4. The apparatus of claim 1, further comprising a sleeve disposed over a portion of the first shaft,
   each elongate member of the plurality of elongate members having a proximal end that is coupled to a distal end of the sleeve and a distal end that is coupled to a distal end of the first shaft, such that relative translation of the sleeve with respect to the first shaft causes the expandable body to transition into the deployed configuration.

5. The apparatus of claim 4, wherein the actuation mechanism is configured to slide distally to advance the sleeve relative to the first shaft to cause the expandable body to transition into the deployed configuration.

6. The apparatus of claim 1, wherein the plurality of nozzle openings includes at least three rows of nozzle openings disposed at different locations along a length of the distal portion of the first shaft.

7. The apparatus of claim 1, wherein the plurality of elongate members includes at least four elongate members distributed evenly around the distal portion of the first shaft.

8. The apparatus of claim 1, further comprising a heating element disposed along at least a portion of the first shaft, the heating element configured to heat at least a portion of an evacuation path for evacuating fluids from within the gallbladder lumen during delivery of the cryogenic ablation medium.

9. The apparatus of claim 8, wherein the heating element includes a wound, resistive wire.

10. The apparatus of claim 1, further comprising a controller configured to:
receive data indicative of the temperature within the gallbladder lumen from the temperature sensor; and
determine a status of the ablation of the wall of the gallbladder lumen based on the data.

11. The apparatus of claim 10, wherein the controller is further configured to control the delivery of the cryogenic ablation medium based on the status of the ablation.

12. An apparatus, comprising:
a first shaft having a proximal end and a distal end and defining a first lumen extending therebetween;
a second shaft disposable within the first lumen and defining a second lumen, the second shaft having a distal portion that is configured to extend out of the distal end of the first shaft and be disposed within a gallbladder lumen;
a first expandable body disposed at the distal end of the first shaft, the first expandable body configured to expand to retain the first shaft in the gallbladder lumen;
a second expandable body disposed around the distal portion of the second shaft, the second expandable body configured to transition from an undeployed configuration to a deployed configuration, the second expandable body formed of a plurality of elongate members that are configured to extend substantially parallel to the second shaft in the undeployed configuration and to bow radially outward from the second shaft in the deployed configuration; and
a plurality of nozzle openings formed on the distal portion of the second shaft between the ends of the second expandable body, the plurality of nozzle openings being in communication with the second lumen such that the second lumen and the plurality of nozzle openings are configured to deliver a cryogenic ablation medium into the gallbladder lumen,
the plurality of elongate members when bowed radially outward from the second shaft being configured to define a volume in the gallbladder lumen around the plurality of nozzle openings that allows the cryogenic ablation medium being delivered via the plurality of nozzle openings to distribute within the gallbladder lumen before contacting and ablating the wall of the gallbladder lumen;
a pressure sensing lumen disposed in the second shaft and configured to terminate in the gallbladder lumen; and
a pressure sensor configured to be disposed outside of the gallbladder lumen, the pressure sensor being fluidically coupled to the pressure sensing lumen and configured to measure a pressure of the gallbladder lumen.

13. The apparatus of claim 12, wherein the plurality of nozzle openings is movable relative to the second expandable body.

14. The apparatus of claim 12, further comprising a sleeve disposed over a portion of the second shaft,
each elongate member of the plurality of elongate members having a proximal end that is coupled to a distal end of the sleeve and a distal end that is coupled to a distal end of the second shaft, such that relative translation of the sleeve with respect to the second shaft causes the second expandable body to transition into the deployed configuration.

15. The apparatus of claim 12, wherein the plurality of nozzle openings includes at least three rows of nozzle openings disposed at different locations along a length of the distal portion of the shaft.

16. The apparatus of claim 12, wherein the plurality of elongate members includes at least four elongate members distributed evenly around the distal portion of the second shaft.

17. The apparatus of claim 12, further comprising a first actuation mechanism configured to be actuated to expand the first expandable body and a second actuation mechanism configured to be actuated to expand the second expandable body, the first and second actuation mechanisms disposed on separate housings coupled to the first and second shafts, respectively.

18. An apparatus, comprising:
a first shaft having a proximal end and a distal end and defining a first lumen extending therebetween;
a second shaft disposable within the first lumen and defining a second lumen, the second shaft having a distal portion that is configured to extend out of the distal end of the first shaft and be disposed within a gallbladder lumen;
an expandable body disposed around the distal portion of the second shaft, the expandable body configured to transition from an undeployed configuration to a deployed configuration, the expandable body formed of a plurality of elongate members that are configured to extend substantially parallel to the second shaft in the undeployed configuration and to bow radially outward from the second shaft in the deployed configuration;
a plurality of nozzle openings formed on the distal portion of the second shaft between the ends of the expandable body, the plurality of nozzle openings being in communication with the second lumen such that the second lumen and the plurality of nozzle openings are configured to deliver a cryogenic ablation medium into the gallbladder lumen;
an evacuation path defined at least in part by one or both of the first and second shafts, the evacuation path configured to evacuate fluids from the gallbladder lumen during the delivery of the cryogenic ablation medium;
a heating element disposed on or in the second shaft and configured to heat at least a portion of the evacuation path to reduce formation of ice within the evacuation path;
a pressure sensing lumen disposed in the second shaft configured to terminate in the gallbladder lumen; and
a pressure sensor configured to be disposed outside of the gallbladder lumen, the pressure sensor being fluidically coupled to the pressure sensing lumen and configured to measure a pressure of the gallbladder lumen.

19. The apparatus of claim 18, wherein the plurality of nozzle openings is movable relative to the expandable body.

20. The apparatus of claim 18, further comprising a sleeve disposed over a portion of the second shaft,
each elongate member of the plurality of elongate members having a proximal end that is coupled to a distal end of the sleeve and a distal end that is coupled to a distal end of the second shaft, such that relative translation of the sleeve with respect to the second shaft causes the expandable body to transition into the deployed configuration.

21. The apparatus of claim 18, wherein the plurality of nozzle openings includes at least three rows of nozzle openings disposed at different locations along a length of the distal portion of the shaft.

22. The apparatus of claim 18, wherein the plurality of elongate members includes at least four elongate members distributed evenly around the distal portion of the second shaft.

23. The apparatus of claim 18, wherein the heating element includes a wound, resistive wire.

24. The apparatus of claim 18, further comprising a controller operatively coupled to the pressure sensor, the controller configured to:
receive data indicative of the pressure of the gallbladder lumen from the pressure sensor; and
detect whether there is a blockage of the evacuation path based on the data.

25. The apparatus of claim 24, wherein the controller is further configured to activate the heating element to heat the evacuation path in response to detecting that there is a blockage of the evacuation path.

26. The apparatus of claim 25, wherein the controller is further configured to terminate delivery of the cryogenic ablation medium in response to the pressure of the gallbladder lumen being above a threshold pressure.

27. The apparatus of claim 18, further comprising a handle coupled to the second shaft, the pressure sensor being disposed within the handle.

28. The apparatus of claim 18, further comprising a housing coupled to the first shaft, the housing including a seal through which the second shaft can be disposed, the seal configured to seal around the second shaft to prevent leakage of fluids around the second shaft.

* * * * *